United States Patent
Katoh et al.

(10) Patent No.: US 8,575,337 B2
(45) Date of Patent: Nov. 5, 2013

(54) OXAZOLIDINONE DERIVATIVE HAVING FUSED RING

(75) Inventors: Issei Katoh, Osaka (JP); Toshiaki Aoki, Osaka (JP); Hideyuki Suzuki, Tokyo-to (JP); Iwao Utsunomiya, Yokohama (JP); Norikazu Kuroda, Osaka (JP); Tsutomu Iwaki, Osaka (JP)

(73) Assignee: Research Foundation Itsuu Laboratory, Tokyo (JP)

( * ) Notice: Subject to any disclaimer, the term of this patent is extended or adjusted under 35 U.S.C. 154(b) by 236 days.

(21) Appl. No.: 13/000,411

(22) PCT Filed: Jun. 23, 2009

(86) PCT No.: PCT/JP2009/061360
§ 371 (c)(1),
(2), (4) Date: Jan. 11, 2011

(87) PCT Pub. No.: WO2009/157423
PCT Pub. Date: Dec. 30, 2009

(65) Prior Publication Data
US 2011/0098471 A1   Apr. 28, 2011

(30) Foreign Application Priority Data
Jun. 24, 2008 (JP) .................. 2008-164255

(51) Int. Cl.
C07D 487/00 (2006.01)
C07D 491/00 (2006.01)
C07D 471/02 (2006.01)

(52) U.S. Cl.
USPC ............. 544/236; 544/350; 546/113

(58) Field of Classification Search
USPC .................. 544/236, 350; 546/113
See application file for complete search history.

(56) References Cited

U.S. PATENT DOCUMENTS

| | | |
|---|---|---|
| 2005/0148604 A1 | 7/2005 | Inoue et al. |
| 2006/0035898 A1 | 2/2006 | Arnold et al. |

FOREIGN PATENT DOCUMENTS

| | | |
|---|---|---|
| EP | 0 352 781 | 7/1989 |
| JP | 2-124877 | 5/1990 |
| JP | 7-500603 | 1/1995 |
| JP | 8-151578 | 6/1996 |
| JP | 2001-514178 | 9/2001 |
| JP | 2007-521282 | 8/2007 |
| WO | 93/09103 | 5/1993 |
| WO | 95/07271 | 3/1995 |
| WO | 99/10342 | 3/1999 |
| WO | 01/81350 | 11/2001 |
| WO | 02/064574 | 8/2002 |
| WO | 03/053975 | 7/2003 |
| WO | 2005/005399 | 1/2005 |
| WO | 2005/019214 | 3/2005 |
| WO | 2005/089763 | 9/2005 |
| WO | 2006/035283 | 4/2006 |
| WO | 2006/038116 | 4/2006 |
| WO | 2006/109156 | 10/2006 |
| WO | 2008/021781 | 2/2008 |

OTHER PUBLICATIONS

Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000).*
West, Solid State Chemistry and Its Applications, John Wiley & Sons, 1984.*
English translation of the International Preliminary Report on Patentability and Written Opinion dated Feb. 8, 2011.
Zhongguo Yaowu Huaxue Zazhi, Chinese Journal of Medicinal Chemistry, vol. 14, No. 5, pp. 263-266, Oct. 2004.
B. B Lohray et al., "Novel Tetrahydro-Thieno Pyridyl Oxazolidinone: An Antibacterial Agent", Bioorganic & Medicinal Chemistry, vol. 12, No. 17, pp. 4557-4564, 2004.
A. R. Renslo et al., "A Distal Methyl Substituent Attenuates Mitochondrial Protein Synthesis Inhibition in Oxazolidinone Antibacterials", Bioorganic & Medicinal Chemistry Letters, vol. 17, pp. 5036-5040, 2007.
F. Reck et al., "Novel Substituted (Pyridin-3-yl)phenyloxazolidinones: Antibacterial Agents with Reduced Activity Against Monoamine Oxidase A and Increased Solubility", J. Med. Chem., vol. 50, No. 20, pp. 4868-4881, 2007.
S. P. East et al., "DNA Gyrase (GyrB)/topoisomerase IV (ParE) Inhibitors: Synthesis and Antibacterial Activity", Bioorganic & Medicinal Chemistry Letters, vol. 19, pp. 894-899, 2009.
R. Griera et al., "New Potential Antibacterials: A Synthetic Route to N-Aryloxazolidinone/3-aryltetrahydroisoquinoline Hybrids", Bioorganic & Medicinal Chemistry Letters, vol. 16, pp. 529-531, 2006.

* cited by examiner

*Primary Examiner* — Nizal Chandrakumar
(74) *Attorney, Agent, or Firm* — Wenderoth, Lind & Ponack, L.L.P.

(57) ABSTRACT

The present invention provides a novel antimicrobial drug comprising an oxazolidinone derivative of the formula (I):

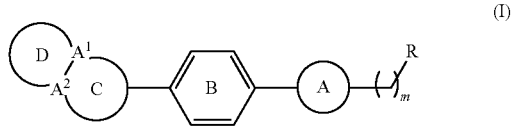

or a pharmaceutically acceptable salt or solvate thereof.

23 Claims, No Drawings

OXAZOLIDINONE DERIVATIVE HAVING FUSED RING

This application is a U.S. national stage of International Application No. PCT/JP2009/061360 filed Jun. 23, 2009.

TECHNICAL FIELD

The invention relates to oxazolidinone derivatives having a fused ring and pharmaceutical (e.g., antimicrobial) compositions comprising the same.

BACKGROUND ART

Various oxazolidinone derivatives having antimicrobial activity were known in the art. For example, it has been known that (S)-n-[[3-[3-fluoro-4-(4-morpholinyl)phenyl]-2-oxo-5-oxazolidinyl]methyl]acetamide ("linezolid") has potent antimicrobial activity on methicillin-resistant *Staphylococcus aureus* (MRSA) and vancomycin-resistant enterococci (VRE) (e.g., see Patent Document 1), and it has been approved and commercially available as anti-VRE infection drug.

Additionally, oxazolidinone type antimicrobial agents having a structure as represented by the following formulae, wherein a 5-6 fused ring is connected to the benzene moiety of linezolid, have been reported (Patent Documents 2 to 7 and Non-Patent Documents 1 and 2).

WO2006/035283 (Patent Document 2):

[Chemical Formula 1]

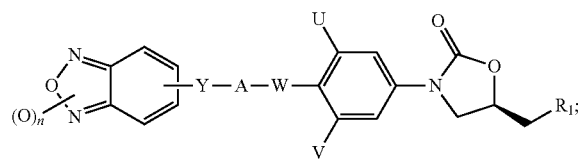

WO2005/019214 (Patent Document 3):

[Chemical Formula 2]

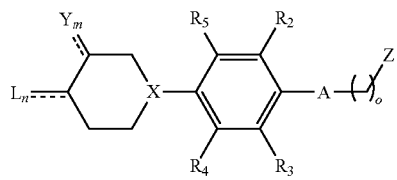

wherein X is N or C;

WO99/10342 (Patent Document 4):

[Chemical Formula 3]

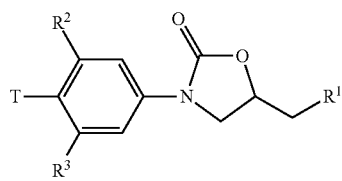

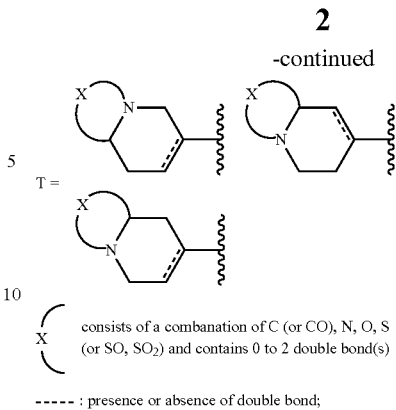

$X$ consists of a combanation of C (or CO), N, O, S (or SO, $SO_2$) and contains 0 to 2 double bond(s)

----- : presence or absence of double bond;

WO93/09103 (Patent Document 5):

[Chemical Formula 4]

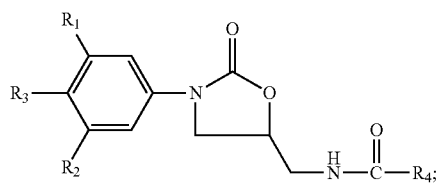

WO2002/064574 (Patent Document 6):

[Chemical Formula 5]

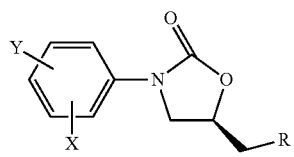

wherein Y is

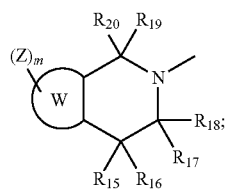

WO2006/109156 (Patent Document 7)

[Chemical Formula 6]

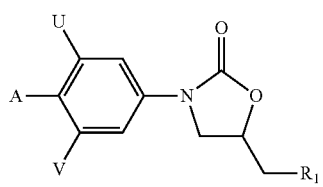

wherein A is selected from

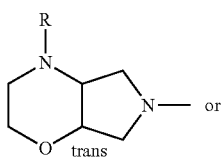

Formula A

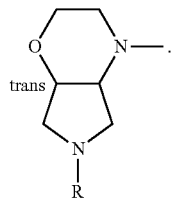

Formula B

WO2008/021781 (Patent Document 8, kinase inhibitor), U.S. Application Publication 2006/0035898 (Patent Document 9, kinase inhibitor), WO2003/053975 (Patent Document 10, PDE7 inhibitor), Japanese Patent Publication 08-151578 (Patent Document 11, compound for liquid-crystal) disclose oxazolidinone derivatives having a fused ring. However, they are not an antimicrobial agent.

Non-Patent Documents 3 and 4 disclose other oxazolidinone type antimicrobial agents.

Patent Document Nos. 12 and 13 and Non-Patent Document 5 disclose antimicrobial agents having a fused hetero ring moiety such as imidazopyridine.

Patent Document 14 discloses a compound having a triazolemethyl group at the 5-position of oxazolidinone ring as an antimicrobial agent.

[Patent Document 1] WO95/07271
[Patent Document 2] WO2006/035283
[Patent Document 3] WO2005/019214
[Patent Document 4] WO99/10342
[Patent Document 5] WO93/09103
[Patent Document 6] WO2002/064574
[Patent Document 7] WO2006/109156
[Patent Document 8] WO2008/021781
[Patent Document 9] U.S. Application Publication 2006/0035898
[Patent Document 10] WO2003/053975
[Patent Document 11] Japanese Patent Publication 08-151578
[Patent Document 12] WO2005/089763
[Patent Document 13] WO2006/038116
[Patent Document 14] WO2001/081350
[Non-Patent Document 1] Zhongguo Yaowu Huaxue Zazhi (2004), 14 (5), p. 263-266
[Non-Patent Document 2] Bioorganic & Medicinal Chemistry (2004), 12 (17), p. 4557-4564
[Non-Patent Document 3] Bioorganic & Medicinal Chemistry Letters 17 (2007) 5036-5040
[Non-Patent Document 4] Journal of Medicinal Chemistry, 2007, Vol. 50, No 20, 4868-4881
[Non-Patent Document 5] Bioorganic & Medicinal Chemistry Letters 19 (2009) 894-899

DISCLOSURE OF THE INVENTION

Problems to be Resolved by the Invention

There is still need for further developments of antimicrobial agent having a strong and broad spectrum of antimicrobial activity. Additionally, there is need for novel antimicrobial agents effective against conventional drug-resistant strains. The invention provides a novel oxazolidinone compound useful as an antimicrobial agent and an antimicrobial agent comprising such compound as an active ingredient. More preferably, the invention provides a compound having an advantage in solubility and in vivo pharmacokinetics, etc. Still more preferably, the invention provides a compound having a reduced side effect (e.g., myelosuppression), compared with conventional antimicrobial agents.

Means of Solving the Problems

The present inventions, as described below, have been accomplished based on the inventors' discovery of novel oxazolidinone derivatives having an antimicrobial activity.

[1] An antimicrobial agent comprising a compound of the formula (I):

[Chemical Formula 7]

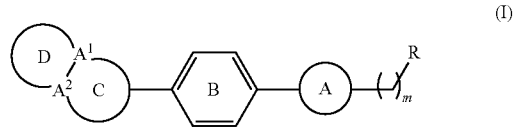

(I)

or a pharmaceutically acceptable salt or solvate thereof; wherein
ring A is any one of the groups:

[Chemical Formula 8]

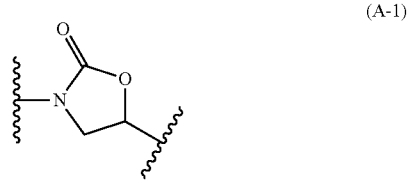

(A-1)

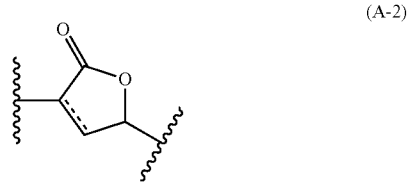

(A-2)

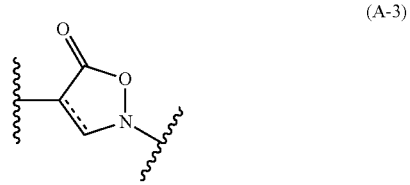

(A-3)

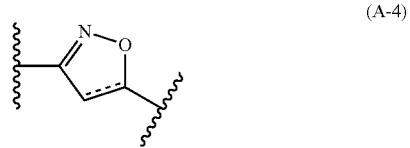

(A-4)

in which dashed line represents presence or absence of a bond;
m is 0 or 1;
R represents H, —NHC(=O)$R^4$, —NHC(=S)$R^4$, —NH-$het^1$, —O-$het^1$, —S-$het^1$, —S(=O)-$het^1$, —S(=O)$_2$-$het^1$, $het^2$, —CONH$R^4$, —OH, lower alkyl, lower alkoxy or lower alkenyl;

R$^4$ is hydrogen, lower alkyl, halogenated lower alkyl, amino, (lower alkyl)amino, lower alkenyl, heterocycle (lower)alkyl, (lower alkyl)carbonyl, (lower alkyl)carbonyl lower alkyl, lower alkoxy, cycloalkyl, cycloalkyl(lower)alkyl, arylcarbonyl, arylcarbonyl(lower)alkyl, heterocyclecarbonyl or heterocyclecarbonyl(lower)alkyl;

het$^1$ and het$^2$ are independently heterocyclic group;

ring B is a benzene ring optionally substituted;

A$^1$ and A$^2$ are independently nitrogen atom or optionally substituted carbon atom;

ring C is an optionally substituted six-membered heterocycle containing at least one nitrogen atom as a ring member and optionally containing one to three double bond(s) in the ring, in which the atom at the point of attachment to ring B is a carbon atom; and ring D is an optionally substituted and optionally fused five-membered ring optionally containing one or two double bond(s) in the ring;

with the proviso that the fused ring C-D is not:

[Chemical Formula 9]

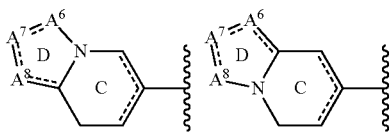

in which
dashed line represents presence or absence of a bond;
A$^6$ is CR$^6$, CR$^6$R$^{6\prime}$, N, NR$^{6\prime\prime}$, O or S;
A$^7$ is CR$^7$, CR$^7$R$^{7\prime}$, N, NR$^{7\prime\prime}$, O or S;
A$^8$ is CR$^8$, CR$^8$R$^{8\prime}$, N, NR$^{8\prime\prime}$, O or S; and
R$^6$, R$^{6\prime}$, R$^7$, R$^{7\prime}$, R$^8$ and R$^{8\prime}$ are independently selected from Substituent Group A consisting of hydrogen, optionally substituted lower alkyl, optionally substituted lower alkenyl, optionally substituted lower alkoxy, carboxy, optionally substituted carbamoyl, cyano, formyl, optionally substituted (lower alkyl)carbonyl, optionally substituted (lower alkoxy) carbonyl, optionally substituted heterocyclic group, optionally substituted heterocyclecarbonyl, optionally substituted amino, optionally substituted aminocarbonyl, optionally substituted aryl, optionally substituted arylcarbonyl, (lower alkyl)sulfonyl, (lower alkyl)sulfinyl and halogen; or R$^6$ and R$^{6\prime}$, R$^7$ and R$^{7\prime}$, and R$^8$ and R$^{8\prime}$ are respectively taken together to form oxo; and R$^{6\prime\prime}$, R$^{7\prime\prime}$ and R$^{8\prime\prime}$ are independently selected from Substituent Group B consisting of hydrogen, optionally substituted lower alkyl, optionally substituted (lower alkyl) carbonyl.

[2] The antimicrobial agent according to [1] wherein ring A is a group of the formula (A-1).

[3] The antimicrobial agent according to [1] wherein m is 1.

[4] The antimicrobial agent according to [1] wherein R is —NHC(=O)R$^4$ in which R$^4$ is lower alkyl.

[5] The antimicrobial agent according to [1] wherein R is a five- or six-membered heterocyclic group containing at least one nitrogen atom.

[6] The antimicrobial agent according to [1] wherein ring B is a benzene ring optionally substituted with same or different one to four substituent(s) selected from the group consisting of hydrogen, halogen, amino, hydroxy, and lower alkyl.

[7] The antimicrobial agent according to [1] wherein ring B is a benzene ring optionally substituted with one or two halogen(s).

[8] The antimicrobial agent according to [1] wherein ring C consists of carbon atoms and nitrogen atoms, in which the number of nitrogen atom is 1 or 2.

[9] The antimicrobial agent according to [1] wherein ring C consists of carbon atoms and nitrogen atoms, in which the number of nitrogen atom is 1 or 2, and any one of A$^1$ and A$^2$ is nitrogen atom and the other is carbon atom.

[10] The antimicrobial agent according to [1] wherein ring C consists of carbon atoms and nitrogen atoms, in which the number of nitrogen atom is 1 or 2, and A$^1$ and A$^2$ are both carbon atoms.

[11] The antimicrobial agent according to [1] wherein ring C consists of carbon atoms and nitrogen atoms, in which the number of nitrogen atom is 1 or 2, and contains two or three double bonds.

[12] The antimicrobial agent according to [1] wherein ring D consists of atoms selected from the group consisting of carbon atom, nitrogen atom, oxygen atom and sulfur atom.

[13] The antimicrobial agent according to [1] wherein ring D consists of atoms selected from the group consisting of carbon atom and nitrogen atom.

[14] The antimicrobial agent according to [1] wherein ring D consists of atoms selected from the group consisting of carbon atom and nitrogen atom, in which the number of nitrogen atom is 1 to 4.

[15] The antimicrobial agent according to [1] wherein ring D consists of atoms selected from the group consisting of carbon atom and nitrogen atom, in which the number of nitrogen atom is 1 or 2, and contains two double bonds.

[16] The antimicrobial agent according to [1] wherein
ring B is a benzene ring optionally substituted with same or different one to four substituent(s) selected from the group consisting of hydrogen, halogen, amino, hydroxy and lower alkyl;

ring C is an optionally substituted six-membered heterocycle consisting of carbon atoms and nitrogen atoms, in which the number of nitrogen atom is 1 or 2, and optionally containing one to three double bond(s) in the ring; and ring D is an optionally substituted five-membered ring consisting of atoms selected from the group consisting of carbon atom, nitrogen atom, oxygen atom and sulfur atom, and optionally containing one or two double bond(s) in the ring.

[17] The antimicrobial agent according to [1]
wherein
ring B is a benzene ring optionally substituted with one or two halogen(s);

ring C is an optionally substituted six-membered heterocycle consisting of carbon atoms and nitrogen atom(s), in which the number of nitrogen atom is 1 or 2, and containing one or two double bond(s) in the ring; and ring D is an optionally substituted five-membered ring consisting of atoms selected from the group consisting of carbon atom and nitrogen atom, in which the number of nitrogen atom is 1 to 4, optionally containing one or two double bond(s) in the ring.

[18] The antimicrobial agent according to [1]
wherein
ring A is a group of the formula (A-1);
m is 1;
R represents —NHC(=O)R$^4$, wherein R$^4$ is lower alkyl, or a five- or six-membered heterocyclic group containing at least one nitrogen atom:
ring B is a benzene ring optionally substituted with one or two halogen(s);
ring C is an optionally substituted six-membered heterocycle consisting of carbon atoms and nitrogen atom(s), in which the number of nitrogen atom is 1 or 2, and optionally containing one to three double bond(s) in the ring, and ring D is an optionally substituted five-membered ring consisting of atoms selected from the group consisting of carbon atom, nitrogen atom, oxygen atom and sulfur atom and optionally containing one or two double bond(s) in the ring.

[19] The antimicrobial agent according to [1] wherein ring A is a group of the formula (A-1);

m is 1;

R represents —NHC(=O)$R^A$, wherein $R^A$ is lower alkyl, or a five- or six-membered heterocyclic group containing at least one nitrogen atom;

ring B is a benzene ring optionally substituted with one or two halogen(s):

ring C is an optionally substituted six-membered heterocycle consisting of carbon atoms and nitrogen atoms, in which the number of nitrogen atom is 1 or 2, and containing two or three double bond(s) in the ring, and ring D is an optionally substituted five-membered ring consisting of atoms selected from the group consisting of carbon atom and nitrogen atom, in which the number of nitrogen atom is 1 to 4, and optionally containing one or two double bond(s) in the ring.

[20] The antimicrobial agent according to [1] wherein ring A is a group of the formula (A-1);

m is 1;

R represents —NHC(=O)$R^A$, wherein $R^A$ is lower alkyl, or a five- or six-membered heterocyclic group containing at least one nitrogen atom:

ring B is a benzene ring optionally substituted with one or two halogen(s):

ring C is an optionally substituted six-membered heterocycle consisting of carbon atoms and nitrogen atoms, in which the number of the nitrogen atom is 2 and any one of $A^1$ and $A^2$ is nitrogen atom and the other is carbon atom, and containing two or three double bond(s) in the ring; and ring D is an optionally substituted five-membered ring consisting of atoms selected from the group consisting of carbon atom and nitrogen atom(s), in which the number of nitrogen atom is 1 to 4, and optionally containing two double bond(s) in the ring.

[21] The antimicrobial agent according to [1] wherein ring A is a group of the formula (A-1);

m is 1;

R represents —NHC(=O)$R^A$, wherein $R^A$ is lower alkyl, or a five- or six-membered heterocyclic group containing at least one nitrogen atom;

ring B is a benzene ring optionally substituted with one or two halogen(s);

ring C is an optionally substituted six-membered heterocycle consisting of carbon atoms and nitrogen atoms, in which the number of the nitrogen atom is 1 and any one of $A^1$ and $A^2$ is nitrogen atom and the other is carbon atom, and containing two double bonds in the ring; and ring D is an optionally substituted five-membered ring consisting of atoms selected from the group consisting of carbon atom and nitrogen atom, in which the number of nitrogen atom is 3, and optionally containing two double bond(s) in the ring.

[22] A compound of the formula (I):

[Chemical Formula 10]

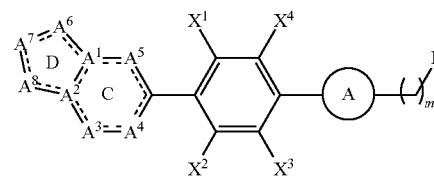

(II)

or a pharmaceutically acceptable salt or solvate thereof; wherein ring A is any one of the groups:

[Chemical Formula 11]

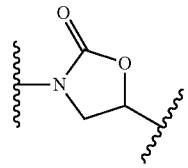

(A-1)

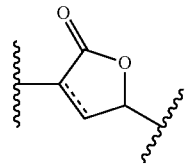

(A-2)

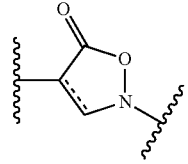

(A-3)

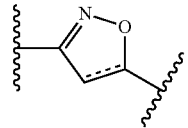

(A-4)

in which dashed line represents presence or absence of a bond;

m is 0 or 1;

R represents H, —NHC(=O)$R^A$, —NHC(=S)$R^A$, —NH-$het^1$, —O-$het^1$, —S-$het^1$, —S(=O)-$het^1$, —S(=O)$_2$-$het^1$, $het^2$, —CONH$R^A$, —OH, lower alkyl, lower alkoxy or lower alkenyl;

$R^A$ is hydrogen, lower alkyl, halogenated lower alkyl, amino, (lower alkyl)amino, lower alkenyl, heterocycle (lower)alkyl, (lower alkyl)carbonyl, (lower alkyl)carbonyl lower alkyl, lower alkoxy, cycloalkyl, cycloalkyl(lower)alkyl, arylcarbonyl, arylcarbonyl(lower)alkyl, heterocyclecarbonyl or heterocyclecarbonyl(lower)alkyl;

$het^1$ and $het^2$ are independently heterocyclic group;

$X^1$, $X^2$, $X^3$, and $X^4$ are independently hydrogen, halogen, amino, hydroxy or lower alkyl;

ring C is a heterocycle;

$A^1$ is C, $CR^1$ or N;

$A^2$ is C, $CR^2$ or N;

$A^3$ is $CR^3$, $CR^3R^{3\prime}$, N or $NR^{3\prime\prime}$;

$A^4$ is $CR^4$, $CR^4R^{4\prime}$, N or $NR^{4\prime\prime}$;
$A^5$ is $CR^5$, $CR^5R^{5\prime}$, N or $NR^{5\prime\prime}$;
$A^6$ is $CR^6$, $CR^6R^{6\prime}$, N, $NR^{6\prime\prime}$, O or S;
$A^7$ is $CR^7$, $CR^7R^{7\prime}$, N, $NR^{7\prime\prime}$, O or S;
$A^8$ is $CR^8$, $CR^8R^{8\prime}$, N, $NR^{8\prime\prime}$, O or S;
$R^1$, $R^2$, $R^3$, $R^{3\prime}$, $R^4$, $R^{4\prime}$, $R^5$, $R^{5\prime}$, $R^6$, $R^{6\prime}$, $R^7$, $R^{7\prime}$, $R^8$ and $R^{8\prime}$ are independently selected from Substituent Group A consisting of hydrogen, optionally substituted lower alkyl, optionally substituted lower alkenyl, optionally substituted lower alkoxy, carboxy, optionally substituted carbamoyl, cyano, formyl, optionally substituted (lower alkyl)carbonyl, optionally substituted (lower alkoxy)carbonyl, optionally substituted heterocyclic group, optionally substituted heterocyclecarbonyl, optionally substituted amino, optionally substituted aminocarbonyl, optionally substituted aryl, optionally substituted arylcarbonyl, (lower alkyl)sulfonyl, (lower alkyl)sulfinyl and halogen; or $R^6$ and $R^{6\prime}$, $R^7$ and $R^{7\prime}$, and $R^8$ and $R^{8\prime}$ are respectively taken together to form oxo;

$R^{6\prime\prime}$ and $R^{7\prime\prime}$ are optionally taken together with the adjacent nitrogen atoms to which they are respectively attached to form optionally substituted heterocycle;

$R^{7\prime\prime}$ and $R^{8\prime\prime}$ are optionally taken together with the adjacent nitrogen atoms to which they are respectively attached to form optionally substituted heterocycle;

$R^{3\prime\prime}$, $R^{4\prime\prime}$, $R^{5\prime\prime}$, $R^{6\prime\prime}$, $R^{7\prime\prime}$ and $R^{8\prime\prime}$ are independently selected from Substituent Group B consisting of hydrogen, optionally substituted lower alkyl, optionally substituted (lower alkyl)carbonyl; and dashed line represents presence or absence of a bond;
with the proviso that the fused ring C-D is not:

[Chemical Formula 12]

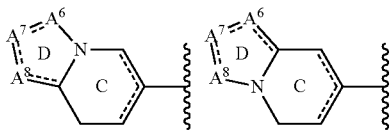

in which each variable is as defined above.

[23] The compound according to [22] wherein any one of $A^1$ and $A^2$ is N and ring C contains two double bonds in the ring, or a pharmaceutically acceptable salt or solvate thereof.

[24] The compound according to [22] represented by the formula

[Chemical Formula 13]

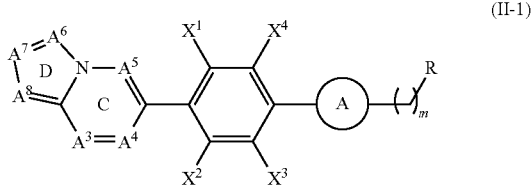

(II-1)

or a pharmaceutically acceptable salt or solvate thereof;
wherein
ring A, m, R, $X^1$, $X^2$, $X^3$ and $X^4$ are as defined in [21];
$A^3$ is $CR^3$ or N;
$A^4$ is $CR^4$ or N;
$A^5$ is $CR^5$ or N;
$A^6$ is $CR^6$ or N;
$A^7$ is $CR^7$ or N;
$A^8$ is $CR^8$ or N; and
$R^3$, $R^4$, $R^5$, $R^6$, $R^7$ and $R^8$ are independently selected from Substituent Group A.

[25] The compound according to [24] wherein $A^3$ is $CR^3$; $A^4$ is $CR^4$; $A^5$ is $CR^5$; $R^3$, $R^4$, and $R^5$ are independently selected from Substituent Group A, or a pharmaceutically acceptable salt or solvate thereof.

[26] The compound according to [24] wherein $A^3$ is CH; $A^4$ is CH; $A^5$ is CH, or any one or two of $R^3$, $R^4$ and $R^5$ is selected from Substituent Group A excluding hydrogen, or a pharmaceutically acceptable salt or solvate thereof.

[27] The compound according to [24] wherein any one of $A^3$, $A^4$ and $A^5$ is N, or a pharmaceutically acceptable salt or solvate thereof.

[28] The compound according to [24] wherein any one of $A^3$, $A^4$ and $A^5$ is N, and the others are CH, or a pharmaceutically acceptable salt or solvate thereof.

[29] The compound according to [24] wherein any one of $A^6$, $A^7$ and $A^8$ is N, or a pharmaceutically acceptable salt or solvate thereof.

[30] The compound according to [24] wherein $A^6$ and/or $A^8$ is N, $A^7$ is $CR^7$, or a pharmaceutically acceptable salt or solvate thereof.

[31] The compound according to [24] wherein any two of $A^6$, $A^7$ and $A^8$ are N, or a pharmaceutically acceptable salt or solvate thereof.

[32] The compound according to [24] wherein $A^7$ and/or $A^8$ is N, and $A^6$ is $CR^6$, or a pharmaceutically acceptable salt or solvate thereof.

[33] The compound according to [24] wherein $A^6$ and $A^8$ are N, $A^7$ is $CR^7$, or a pharmaceutically acceptable salt or solvate thereof.

[34] The compound according to [24] wherein $A^6$, $A^7$ and $A^8$ are N, or a pharmaceutically acceptable salt or solvate thereof.

[35] The compound according to [24] wherein the fused ring C-D is any one of the rings:

[Chemical Formula 14]

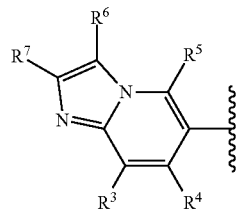

(II-1-1)

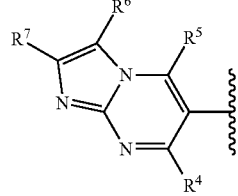

(II-1-2)

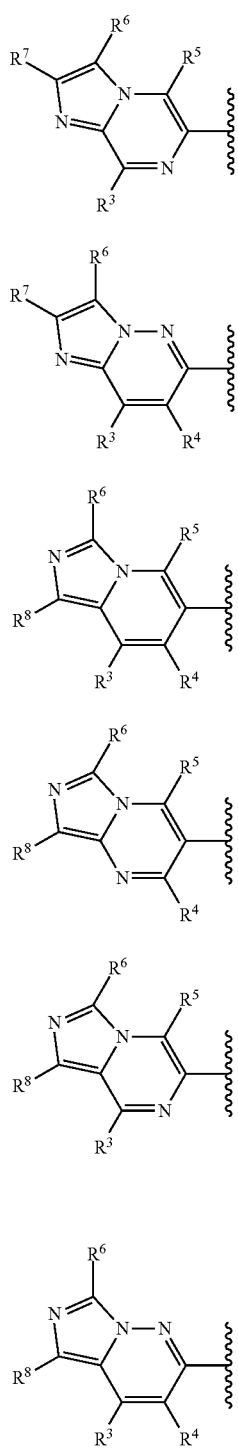
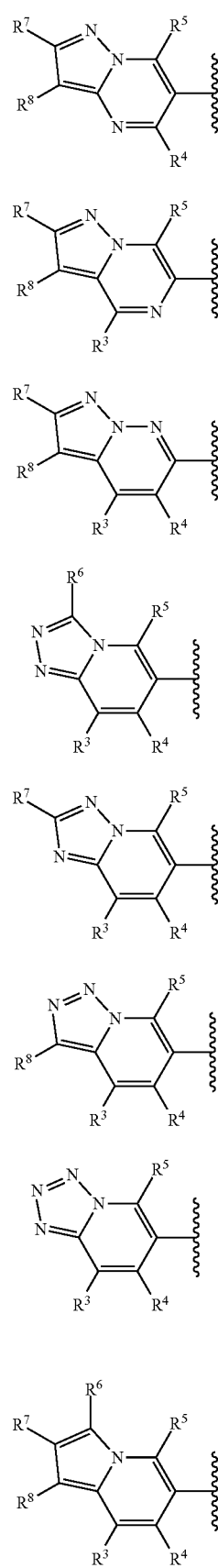

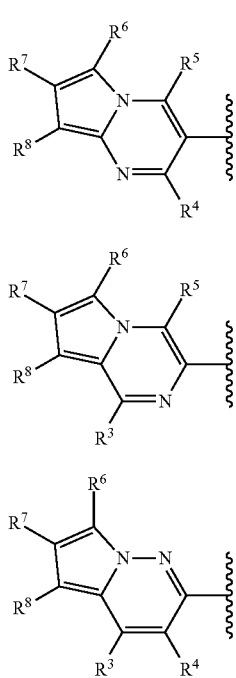

(II-1-18)

(II-1-19)

(II-1-20)

wherein each variable is as defined above,
or a pharmaceutically acceptable salt or solvate thereof.

[36] The compound according to [35] wherein the fused ring C-D in the formula (II-1) is

[Chemical Formula 15]

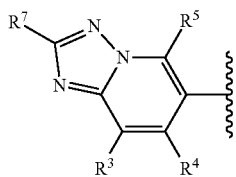

(II-1-14)

or a pharmaceutically acceptable salt or solvate thereof.

[37] The compound according to [36] wherein $R^3$, $R^4$ and $R^5$ are all hydrogen; $R^7$ is hydrogen, optionally substituted lower alkyl, optionally substituted amino, formyl, or optionally substituted (lower alkyl)carbonyl, or a pharmaceutically acceptable salt or solvate thereof.

[38] The compound according to [22] of the formula:

[Chemical Formula 16]

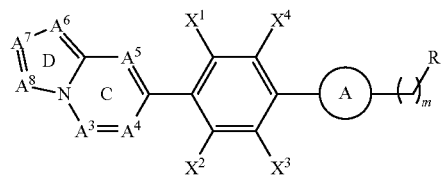

(II-2)

wherein
ring A, m, R, $X^1$, $X^2$, $X^3$ and $X^4$ are as defined in [22];
$A^3$ is $CR^3$ or N;
$A^4$ is $CR^4$ or N;
$A^5$ is $CR^5$ or N;
$A^6$ is $CR^6$ or N;
$A^7$ is $CR^7$ or N;
$A^8$ is $CR^8$ or N; and
$R^3$, $R^4$, $R^5$, $R^6$, $R^7$ and $R^8$ are independently selected from Substituent Group A,
or a pharmaceutically acceptable salt or solvate thereof.

[39] The compound according to [38] wherein $A^3$ is $CR^3$; $A^4$ is $CR^4$; $A^5$ is $CR^5$; $R^3$, $R^4$, and $R^5$ are independently selected from Substituent Group A, or a pharmaceutically acceptable salt or solvate thereof.

[40] The compound according to [38] wherein $A^3$ is CH; $A^4$ is CH; $A^5$ is CH, or any one or two of $R^3$, $R^4$, and $R^5$ is selected from Substituent Group A excluding hydrogen, or a pharmaceutically acceptable salt or solvate thereof.

[41] The compound according to [38] wherein any one of $A^3$, $A^4$ and $A^5$ is N, or a pharmaceutically acceptable salt or solvate thereof.

[42] The compound according to [38] wherein any one of $A^3$, $A^4$ and $A^5$ is N, and the others are CH, or a pharmaceutically acceptable salt or solvate thereof.

[43] The compound according to [38] wherein any one of $A^6$, $A^7$ and $A^8$ is N, or a pharmaceutically acceptable salt or solvate thereof.

[44] The compound according to [38] wherein $A^6$ and/or $A^6$ is N, and $A^7$ is $CR^7$, or a pharmaceutically acceptable salt or solvate thereof.

[45] The compound according to [38] wherein $A^6$ and $A^8$ is N, $A^7$ is $CR^7$, or a pharmaceutically acceptable salt or solvate thereof.

[46] The compound according to [38] wherein any two of $A^6$, $A^7$ and $A^8$ are N, or a pharmaceutically acceptable salt or solvate thereof.

[47] The compound according to [38] wherein $A^7$ and/or $A^8$ is N, $A^6$ is $CR^6$, or a pharmaceutically acceptable salt or solvate thereof.

[48] The compound according to [38] wherein $A^6$, $A^7$ and $A^8$ are N, or a pharmaceutically acceptable salt or solvate thereof.

[49] The compound according to [38] wherein the fused ring C-D in the formula (II-2) is selected from the group consisting of:

[Chemical Formula 17]

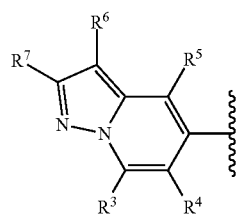

(II-2-1)

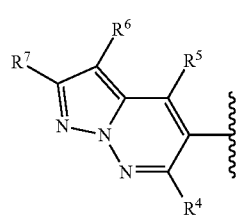

(II-2-2)

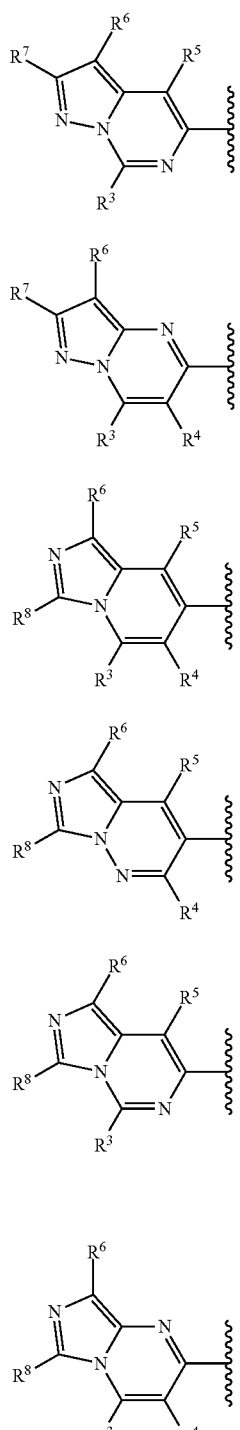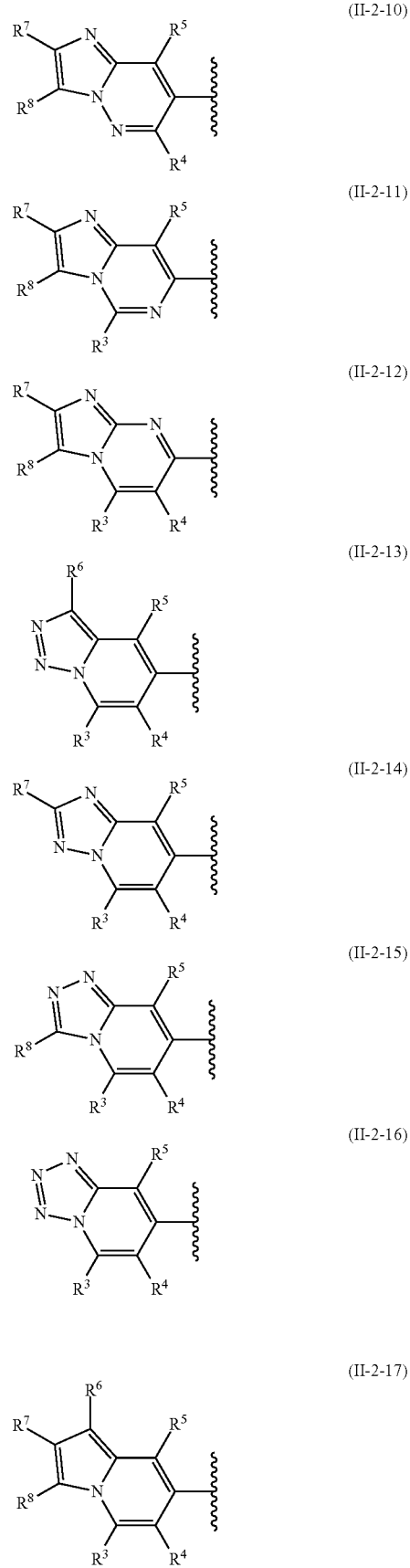

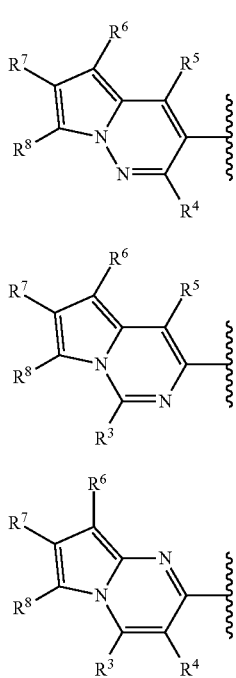

(II-2-18)

(II-2-19)

(II-2-20)

wherein each variable is as defined above or a pharmaceutically acceptable salt or solvate thereof.

[50] The compound according to [49] wherein the fused ring C-D in the formula (II-2) is

[Chemical Formula 18]

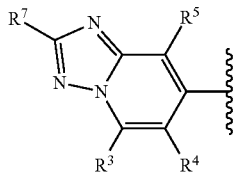

(II-2-14)

or a pharmaceutically acceptable salt or solvate thereof.

[51] The compound according to [50] wherein $R^3$, $R^4$ and $R^5$ are all hydrogen; $R^7$ is hydrogen, optionally substituted lower alkyl, optionally substituted amino, formyl, or optionally substituted (lower alkyl)carbonyl, or a pharmaceutically acceptable salt or solvate thereof.

[52] The compound according to [22] of the formula:

[Chemical Formula 19]

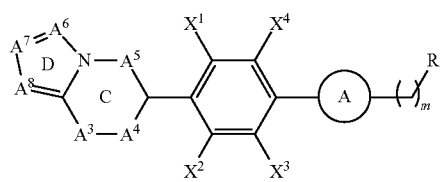

(II-3)

or a pharmaceutically acceptable salt or solvate thereof;

wherein
ring A, m, R, $X^1$, $X^2$, $X^3$ and $X^4$ are as defined in [22];
$A^3$ is $CR^3R^{3\prime}$ or $NR^{3\prime\prime}$;
$A^4$ is $CR^4R^{4\prime}$ or $NR^{4\prime\prime}$;
$A^5$ is $CR^5R^{5\prime}$ or $NR^{5\prime\prime}$;
with the proviso that at least one of $A^3$, $A^4$ and $A^5$ contains nitrogen atom;
$A^6$ is $CR^6$ or N;
$A^7$ is $CR^7$ or N;
$A^8$ is $CR^8$ or N;
$R^{3\prime}$, $R^{3\prime}$, $R^4$, $R^{4\prime}$, $R^5$, $R^{5\prime}$, $R^6$, $R^7$ and $R^8$ are independently selected from Substituent Group A;
$R^{3\prime\prime}$, $R^{4\prime\prime}$ and $R^{5\prime\prime}$ are independently selected from Substituent Group B.

[53] The compound according to [52] wherein any one of $A^3$, $A^4$ and $A^5$ contains nitrogen atom, and any one or two of $A^6$, $A^7$, and $A^8$ is N, or a pharmaceutically acceptable salt or solvate thereof.

[54] The compound according to [52] wherein the fused ring C-D in the formula (II-3) is selected from the group consisting of

[Chemical Formula 20]

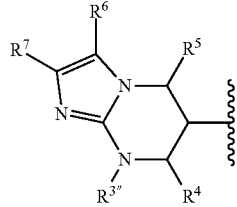

(II-3-1)

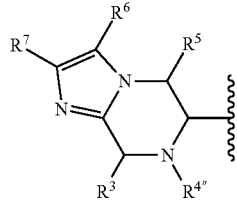

(II-3-2)

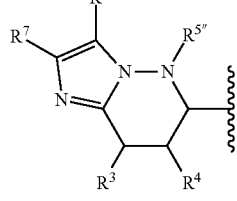

(II-3-3)

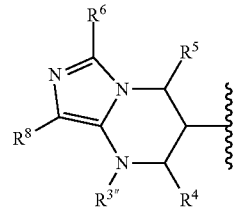

(II-3-4)

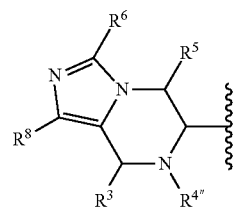

(II-3-5)

(II-3-6)
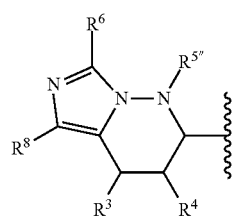
(II-3-7)
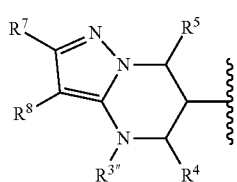
(II-3-8)
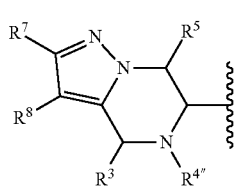
(II-3-9)
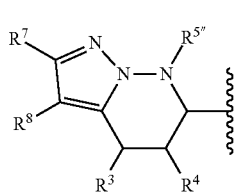
(II-3-10)
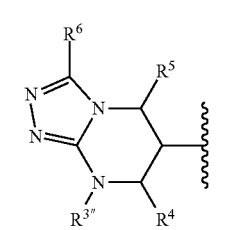
(II-3-11)
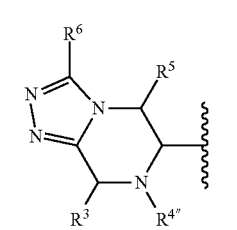
(II-3-12)
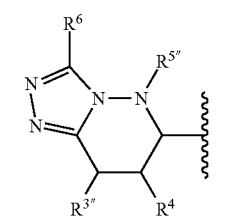
(II-3-13)
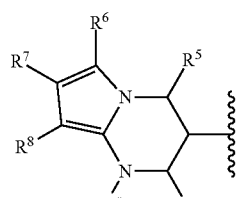
(II-3-14)
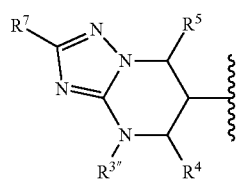
(II-3-15)
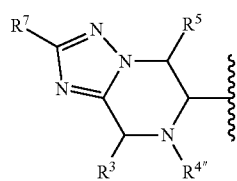
(II-3-16)
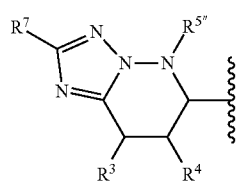
(II-3-17)
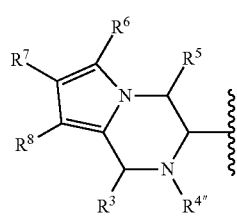
(II-3-18)
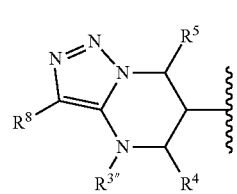
(II-3-19)
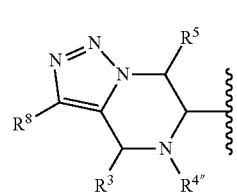
(II-3-20)
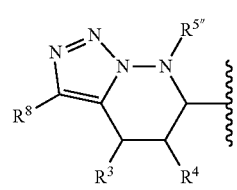

-continued (II-3-21)

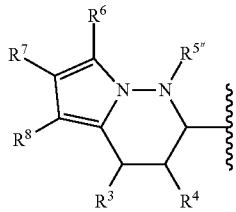

wherein each variable is as defined above,
or a pharmaceutically acceptable salt or solvate thereof.

[55] The compound according to [22] of the formula:

[Chemical Formula 21]

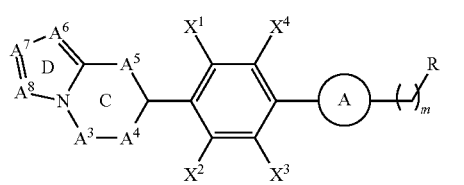

(II-4)

or a pharmaceutically acceptable salt or solvate thereof;
wherein
  ring A, m, R, $X^1$, $X^2$, $X^3$ and $X^4$ are as defined in [22];
  $A^3$ is $CR^3R^{3'}$ or $NR^{3''}$;
  $A^4$ is $CR^4R^{4'}$ or $NR^{4''}$;
  $A^5$ is $CR^5R^{5'}$ or $NR^{5''}$;
with the proviso that at least one of $A^3$, $A^4$ and $A^5$ contains nitrogen atom;
  $A^6$ is $CR^6$ or N;
  $A^7$ is $CR^7$ or N;
  $A^6$ is $CR^8$ or N;
  $R^3$, $R^{3'}$, $R^4$, $R^{4'}$, $R^5$, $R^{5'}$, $R^6$, $R^7$, and $R^8$ are independently selected from Substituent Group A; and
  $R^{3''}$, $R^{4''}$ and $R^{5''}$ are independently selected from Substituent Group B.

[56] The compound according to [55] wherein any one of $A^3$, $A^4$ and $A^5$ contains nitrogen atom, and any one or two of $A^6$, $A^7$, and $A^8$ is N, or a pharmaceutically acceptable salt or solvate thereof.

[57] The compound according to [55] wherein the fused ring C-D in the formula (II-4) is selected from the group consisting of

[Chemical Formula 22]

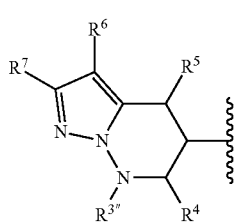

(II-4-1)

-continued

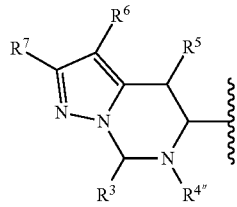

(II-4-2)

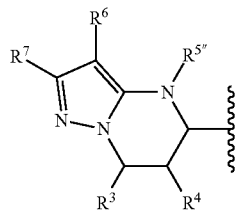

(II-4-3)

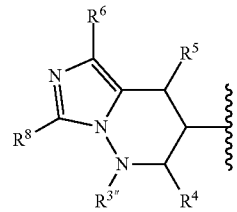

(II-4-4)

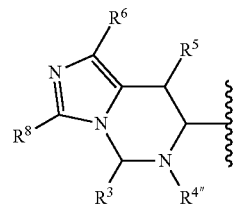

(II-4-5)

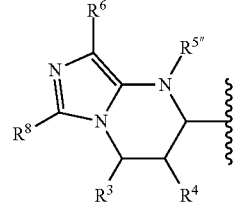

(II-4-6)

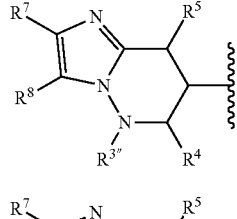

(II-4-7)

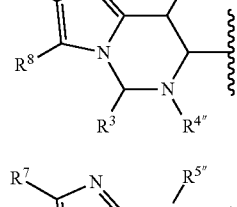

(II-4-8)

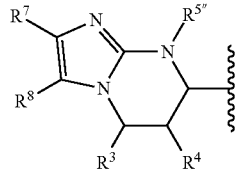

(II-4-9)

-continued

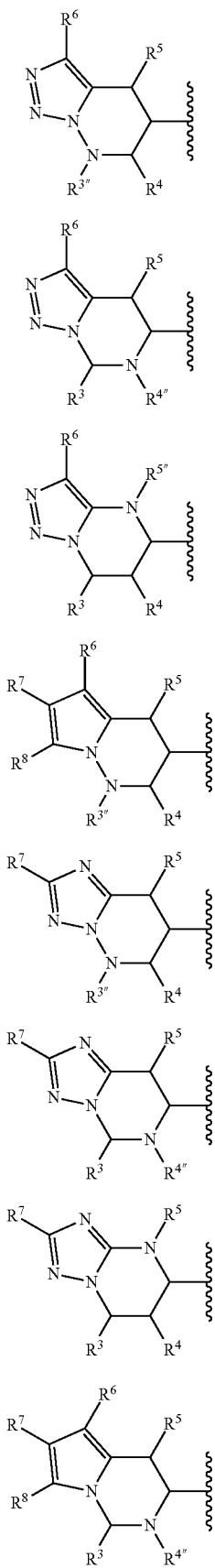

(II-4-10)
(II-4-11)
(II-4-12)
(II-4-13)
(II-4-14)
(II-4-15)
(II-4-16)
(II-4-17)

-continued

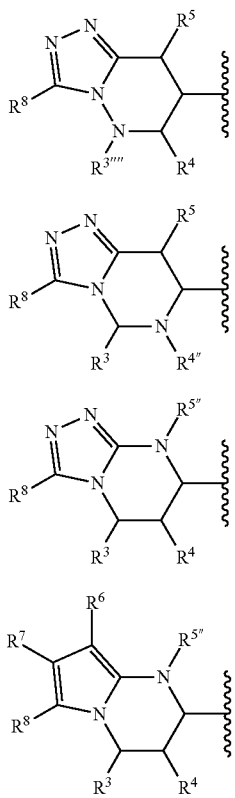

(II-4-18)
(II-4-19)
(II-4-20)
(II-4-21)

wherein each variable is as defined above,
or a pharmaceutically acceptable salt or solvate thereof.

[58] The compound according to [22] of the formula:

[Chemical Formula 23]

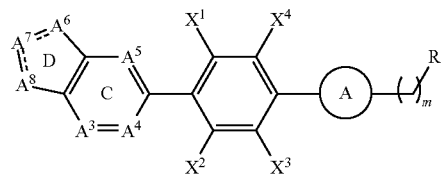

(II-5)

or a pharmaceutically acceptable salt or solvate thereof;
wherein
  ring A, m, R, $X^1$, $X^2$, $X^3$ and $X^4$ are as defined in [22];
  $A^3$ is $CR^3$ or N;
  $A^4$ is $CR^4$ or N;
  $A^5$ is $CR^5$ or N;
  with the proviso that at least one of $A^3$, $A^4$ and $A^5$ contains nitrogen atom;
  $A^6$ is $CR^6$, $CR^6R^{6\prime}$, N, $NR^{6\prime\prime}$, O or S;
  $A^7$ is $CR^7$, $CR^7R^{7\prime}$, N, $NR^{7\prime\prime}$, O or S;
  $A^8$ is $CR^8$, $CR^8R^{8\prime}$, N, $NR^{8\prime\prime}$, O or S;
  $R^3$, $R^4$, $R^5$, $R^6$, $R^{6\prime}$, $R^7$, $R^{7\prime}$, $R^8$ and $R^{8\prime}$ are independently selected from Substituent Group A; or
  $R^6$ and $R^{6\prime}$, $R^7$ and $R^{7\prime}$, and $R^8$ and $R^{8\prime}$ are respectively taken together to form oxo;
  $R^{6\prime\prime\prime}$, $R^{7\prime\prime\prime}$ and $R^{8\prime\prime\prime}$ are independently selected from Substituent Group B; and
  dashed line represents presence or absence of a bond.

[59] The compound according to [58] wherein any one or two of $A^3$, $A^4$ and $A^5$ is nitrogen atom, and any one of $A^6$, $A^7$ and $A^8$ contains nitrogen atom, or a pharmaceutically acceptable salt or solvate thereof.

[60] The compound according to [58] wherein the fused ring C-D in the formula (II-5) is selected from the group consisting of:

[Chemical Formula 24]

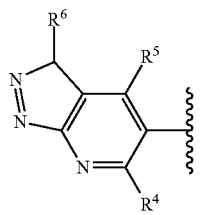
(II-5-1)

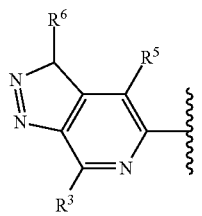
(II-5-2)

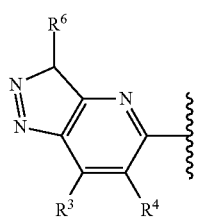
(II-5-3)

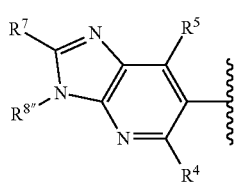
(II-5-4)

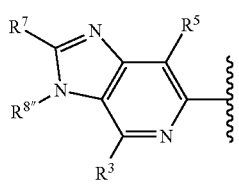
(II-5-5)

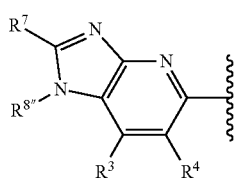
(II-5-6)

-continued

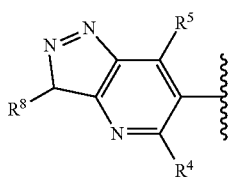
(II-5-7)

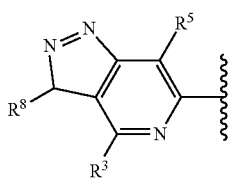
(II-5-8)

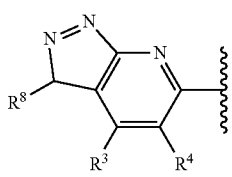
(II-5-9)

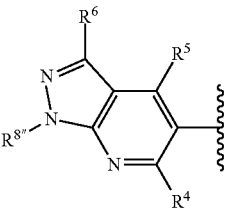
(II-5-10)

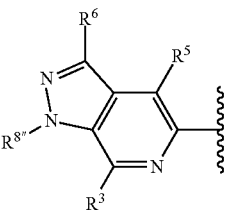
(II-5-11)

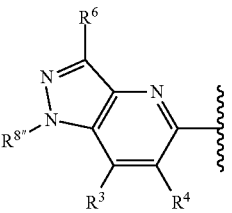
(II-5-12)

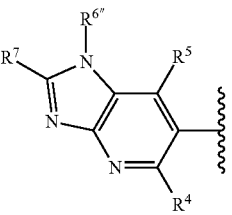
(II-5-13)

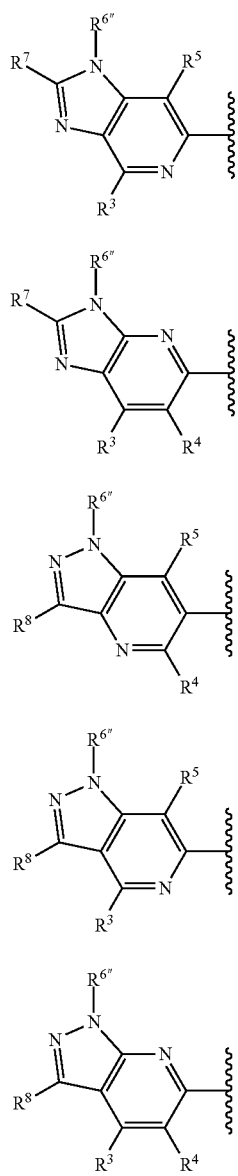
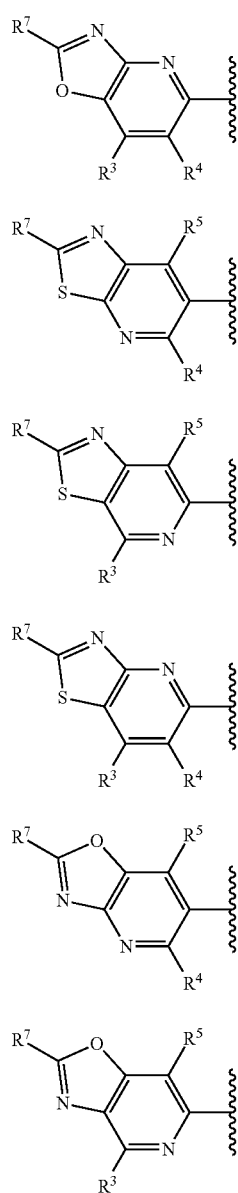

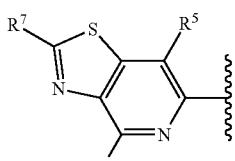 (II-5-29)
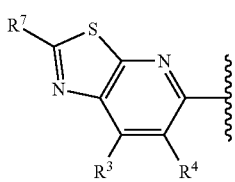 (II-5-30)
[Chemical Formula 26]
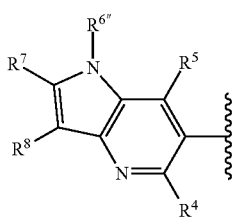 (II-5-31)
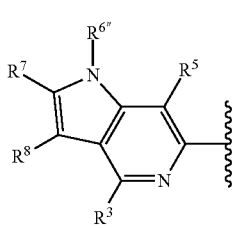 (II-5-32)
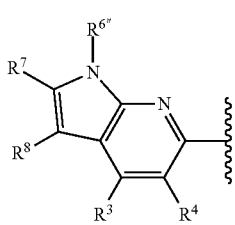 (II-5-33)
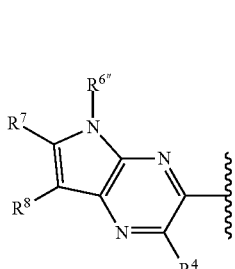 (II-5-34)
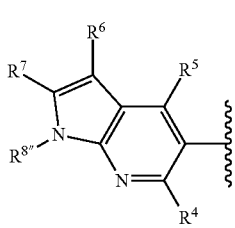 (II-5-35)
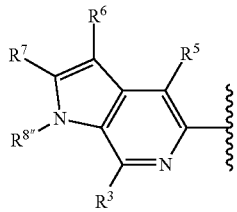 (II-5-36)
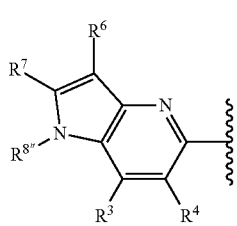 (II-5-37)
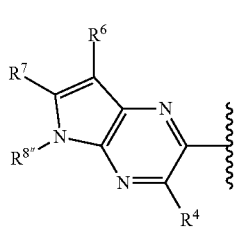 (II-5-38)
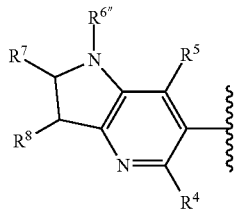 (II-5-39)
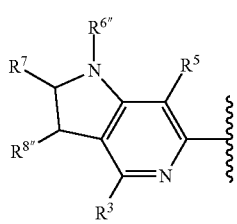 (II-5-40)
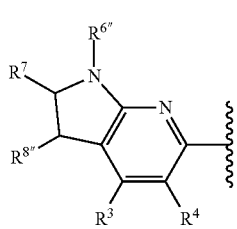 (II-5-41)
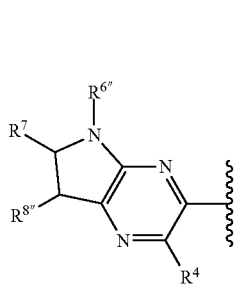 (II-5-42)

(II-5-43)
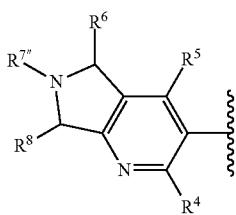

(II-5-44)
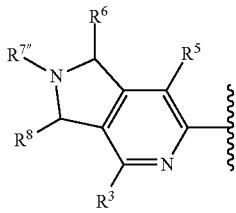

(II-5-45)
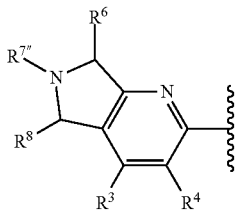

(II-5-46)
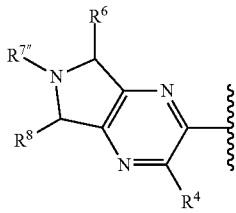

(II-5-47)
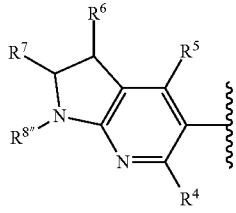

(II-5-48)
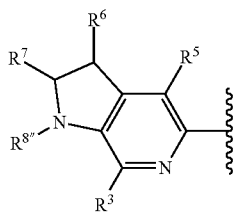

(II-5-49)
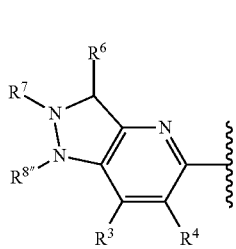

(II-5-50)
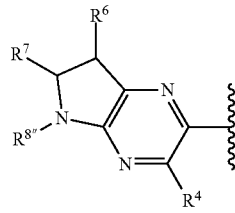

wherein each variable is as defined above,
or a pharmaceutically acceptable salt or solvate thereof.

[61] The compound according to [22] of the formula:

[Chemical Formula 27]

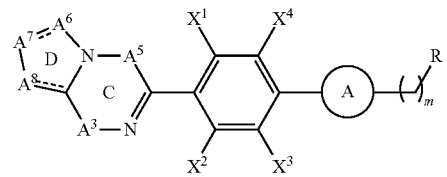

(II-6)

or a pharmaceutically acceptable salt or solvate thereof;
wherein
ring A, m, R, $X^1$, $X^2$, $X^3$ and $X^4$ are as defined in [22];
$A^3$ is $CR^3R^{3'}$ or $NR^{3''}$;
$A^5$ is $CR^5R^{5'}$ or $NR^{5''}$;
$A^6$ is $CR^6$, $CR^6R^{6'}$, N, $NR^{6''}$, O or S;
$A^7$ is $CR^7$, $CR^7R^{7'}$, N, $NR^{7''}$, O or S;
$A^8$ is $CR^8$, $CR^8R^{8'}$, N, $NR^{8''}$, O or S;
$R^3$, $R^{3'}$, $R^5$, $R^{5'}$, $R^6$, $R^{6'}$, $R^7$, $R^{7'}$, $R^8$ and $R^{8'}$ are independently selected from Substituent Group A; or
$R^6$ and $R^{6'}$, $R^7$ and $R^{7'}$, and $R^8$ and $R^{8'}$ are respectively taken together to form oxo;
$R^{3''}$, $R^{5''}$, $R^{6''}$, $R^{7''}$ and $R^{8''}$ are independently selected from Substituent Group B; and
dashed line represents presence or absence of a bond.

[62] The compound according to [61] wherein $A^3$ is $CHR^3$; $A^5$ is $CHR^5$; $A^6$ is $CR^6$; $A^7$ is N; $A^8$ is $CR^8$; and ring D contains two double bonds in the ring, or a pharmaceutically acceptable salt or solvate thereof.

[63] A compound of the formula:

[Chemical Formula 28]

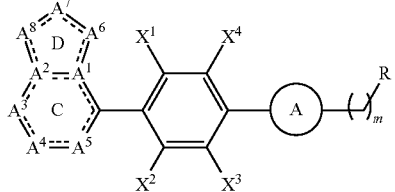

(III)

or a pharmaceutically acceptable salt or solvate thereof;
wherein
ring A, m, and R are as defined in [1];
$X^1$, $X^2$, $X^3$ and $X^4$ are independently hydrogen, halogen, amino, hydroxy or lower alkyl;
ring C is heterocycle;
$A^1$ is C, $CR^1$, or N;

$A^2$ is C, $CR^2$, or N;
$A^3$ is $CR^3$, $CR^3R^{3\prime}$, N or $NR^{3\prime\prime\prime}$;
$A^4$ is $CR^4$, $CR^4R^{4\prime}$, N or $NR^{4\prime\prime\prime}$;
$A^5$ is $CR^5$, $CR^5R^{5\prime}$, N or $NR^{5\prime\prime\prime}$;
$A^6$ is $CR^6$, $CR^6R^{6\prime}$, N, $NR^{6\prime\prime\prime}$, O or S;
$A^7$ is $CR^7$, $CR^7R^{7\prime}$, N, $NR^{7\prime\prime\prime}$, O or S;
$A^8$ is $CR^8$, $CR^8R^{8\prime}$, N, $NR^{8\prime\prime\prime}$, O or S;

$R^1$, $R^2$, $R^3$, $R^{3\prime}$, $R^5$, $R^{5\prime}$, $R^6$, $R^{6\prime}$, $R^7$, $R^{7\prime}$, $R^8$, and $R^{8\prime}$ are independently selected from Substituent Group A consisting of hydrogen, optionally substituted lower alkyl, optionally substituted lower alkenyl, optionally substituted lower alkoxy, carboxy, optionally substituted carbamoyl, cyano, formyl, optionally substituted (lower alkyl)carbonyl, optionally substituted (lower alkoxy)carbonyl, optionally substituted heterocyclic group, optionally substituted heterocyclecarbonyl, optionally substituted amino, optionally substituted aminocarbonyl, optionally substituted aryl, optionally substituted arylcarbonyl, (lower alkyl)sulfonyl, (lower alkyl)sulfinyl and halogen; or $R^6$ and $R^{6\prime}$, $R^7$ and $R^{7\prime}$, and $R^8$ and $R^{8\prime}$ are respectively taken together to form oxo;

$R^{3\prime\prime\prime}$, $R^{4\prime\prime\prime}$, $R^{5\prime\prime\prime}$, $R^{6\prime\prime\prime}$, $R^{7\prime\prime\prime}$ and $R^{8\prime\prime\prime}$ are independently selected from Substituent Group B consisting of hydrogen, optionally substituted lower alkyl and optionally substituted (lower alkyl)carbonyl; and dashed line represents presence or absence of a bond.

[64] The compound according to [63] wherein any one of $A^1$ and $A^2$ is N, or a pharmaceutically acceptable salt or solvate thereof.

[65] The compound according to [63] of the formula:

[Chemical Formula 29]

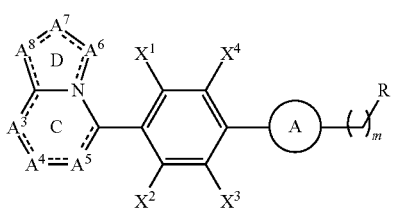

(III-1)

wherein each variable is as defined above,
or a pharmaceutically acceptable salt or solvate thereof.

[66] The compound according to [63] of the formula:

[Chemical Formula 30]

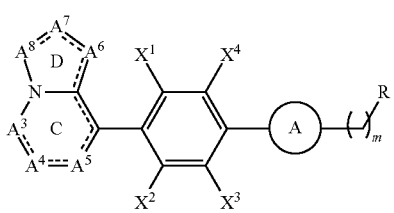

(III-2)

wherein each variable is as defined above,
or a pharmaceutically acceptable salt or solvate thereof.

[67] The compound according to any one of [22] to [66] wherein ring A is a group of the formula (A-1), or a pharmaceutically acceptable salt or solvate thereof.

[68] The compound according to any one of [22] to [66] wherein m is 1, or a pharmaceutically acceptable salt or solvate thereof.

[69] The compound according to any one of [22] to [66] wherein R is —NHC(=O)$R^A$ in which $R^A$ is lower alkyl, or a pharmaceutically acceptable salt or solvate thereof.

[70] The compound according to any one of [22] to [66] wherein R is a five- or six-membered heterocyclic group containing at least one nitrogen atom, or a pharmaceutically acceptable salt or solvate thereof.

[71] The compound according to any one of [22] to [66] wherein R is selected from the group consisting of

[Chemical Formula 31]

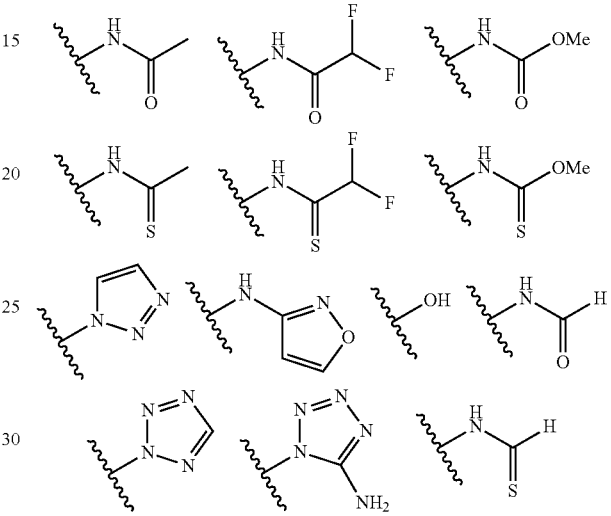

or a pharmaceutically acceptable salt or solvate thereof.

[72] The compound according to [71] wherein R is

[Chemical Formula 32]

or a pharmaceutically acceptable salt or solvate thereof.

[73] The compound according to [71] wherein R is

[Chemical Formula 33]

or a pharmaceutically acceptable salt or solvate thereof.

Effect of the Invention

The oxazolidinone derivative of the invention is useful as a drug (e.g., antimicrobials) or an intermediate for the synthesis of such drug. Also, the oxazolidinone derivative of the invention has a potent antimicrobial activity against gram-positive strains and gram-negative strains. Especially, the compound exhibits a broad spectrum of antimicrobial activity against drug-resistant gram-positive strains, including methicillin-resistant *Staphylococcus aureus* (MRSA), vancomycin-resistant enterococci (VRE), penicillin-resistant pneumococcus (PRSP). More preferably, the compound of the invention is effective against linezolid resistant (LZD-R) strains. More preferably, the compound of the invention shows good solubility or oral absorbability, which allows for administration by injection. Still more preferably, the compound of the invention reduces the side-effects concerned in conventional antimicrobial agents (e.g., linezolid), such as myelosuppression, monoamine oxidase (MAO) inhibiting activity, and neurotoxicity. Decreased MAO inhibition is preferred because side-effects, such as metabolism suppression of dopamine, serotonin, etc., blood pressure elevation, agitation, etc., are concerned by such inhibition. Additionally, preferred compound of the invention also shows good profiles in pharmacokinetics, such as CYP inhibition, PK profile, and plasma stability. Still more preferred compound of the invention has advantageous property such as short treatment period compared to conventional drugs, once-a-day dosing, low occurrence rate of resistant strain, etc.

BEST MODE FOR CARRYING OUT THE INVENTION

The terms as used herein are described below. Each term, alone or in combination with another term, has the following meaning unless otherwise specifically indicated.

The term "lower alkyl" refers to C1-C6 straight or branched monovalent hydrocarbon radical, such as methyl, ethyl, n-propyl, isopropyl, n-butyl, isobutyl, sec-butyl, tert-butyl, n-pentyl, isopentyl, neo-pentyl, n-hexyl, isohexyl and the like.

The term "lower alkenyl" refers to straight or branched chain group of 2 to 6 carbon atoms having one or more double bond(s) in the "lower alkyl" as defined above and includes, for example, vinyl, propenyl, butenyl and the like.

The term "lower alkylene" refers to straight or branched C1-C6 alkylene and includes methylene, ethylene, trimethylene, propylene, tetramethylene, ethylethylene, pentamethylene, hexamethylene and the like.

The term "lower alkenylene" refers to straight or branched chain group of 2 to 6 carbon atoms having one or more double bond(s) in the "lower alkylene" as defined above and includes, for example, vinylene, propenylene, butenylene and the like.

The terms "lower alkoxy" and "lower alkyloxy" refer to an oxy attached to the "lower alkyl" as defined above and include, for example, methoxy, ethoxy, n-propoxy, isopropoxy, n-butoxy, isobutoxy, sec-butoxy, tert-butoxy, n-pentoxy, isopentoxy, neopentoxy, tert-pentoxy, n-hexyloxy, isohexyloxy and the like.

The term "halogen" means fluorine, chlorine, bromine or iodine.

The term "carbocycle" refers to aryl, cycloalkyl or cycloalkenyl and includes cyclobutane, cyclopentane, cyclohexane, cycloheptane, benzene, naphthalene and the like. 5- to 7-membered ring is preferable, and 6-membered ring is especially preferable.

The term "aryl" refers to monocyclic or fused aromatic hydrocarbon and includes phenyl, 1-naphthyl, 2-naphthyl, anthryl and the like.

The term "cycloalkyl" includes cyclic saturated hydrocarbon of three to eight carbon atoms and includes cyclopropyl, cyclobutyl, cyclopentyl, cyclohexyl, cycloheptyl and cyclooctyl and the like.

The term "heterocycle" and "heterocyclic group" refer to a ring wherein a carbon atom in the above "carbocycle" is replaced with at least one hetero atom independently selected from nitrogen atom, oxygen atom or sulphur atom and include heteroaryl, non-aromatic heterocycle and the like. The term "heterocycle" also includes those having a fused ring.

The term "heteroaryl" refers to monocyclic aromatic heterocyclic group or fused aromatic heterocyclic group. The monocyclic aromatic heterocyclic group refers to a group derived from a 5- to 8-membered aromatic ring having a point of attachment at any substitutable position and containing one to four oxygen atom(s), sulfur atom and/or nitrogen atom in the ring. The fused aromatic heterocyclic group refers to a group having a point of attachment at any substitutable position wherein a 5- to 8-membered aromatic ring containing one to four oxygen atom(s), sulfur atom and/or nitrogen atom is fused with one to four 5- to 8-membered aromatic carbocycle(s) or other 5- to 8-membered aromatic heterocycle(s). Examples include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazole-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl (e.g., 2-benzoxazolyl, 4-benzoxazolyl, 5-benzoxazolyl, 6-benzoxazolyl, 7-benzoxazolyl, 8-benzoxazolyl), quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiazinyl (e.g., 1-phenothiazinyl, 2-phenothiazinyl, 3-phenothiazinyl, 4-phenothiazinyl), etc.

The term "non-aromatic heterocycle" refers to a non-aromatic heterocyclic group having a point of attachment at any substitutable position and at least one nitrogen atom, oxygen atom and/or sulfur atom in the ring. Examples include 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperadino, 2-piperazinyl, 2-morpholinyl, 3-morpholinyl, morpholino, tetrahydropyranyl, etc. The term "non-aromatic heterocyclic group" may be saturated or unsaturated as far as it is non-aromatic.

The terms "(lower alkyl)carbonyl", "(lower alkoxy)carbonyl", "arylcarbonyl" and "heterocyclecarbonyl" refer to carbonyl attached to the above "lower alkyl", "lower alkoxy", "aryl" and "heterocyclic group", respectively.

The term "halogenated lower alkyl" refers to "lower alkyl" as defined above which is substituted with at least one halogen as defined above.

The terms "heterocycle (lower)alkyl", "(lower alkyl)carbonyl lower alkyl", "cycloalkyl(lower)alkyl", "arylcarbonyl (lower)alkyl", "heterocyclecarbonyl(lower)alkyl" refer to "lower alkyl" as defined above attached to "heterocyclic group", "(lower alkyl)carbonyl", "cycloalkyl", "arylcarbonyl", "heterocyclecarbonyl", respectively.

The terms "(lower alkyl)amino", "(lower alkyl)sulfonyl", "(lower alkyl)sulfinyl" refer to "lower alkyl" as defined above attached to amino, sulphonyl, sulfinyl, respectively.

One embodiment of the invention provides a pharmaceutical composition having an antimicrobial effect comprising a compound of the formula:

[Chemical Formula 34]

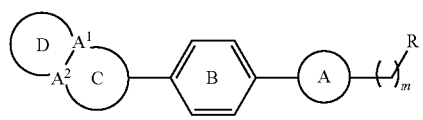

(I)

(compound (I)), or a pharmaceutically acceptable salt or solvate thereof.

Preferred embodiment of the compound of the formula (I) includes compound (II) and (III) of the formulae:

[Chemical Formula 35]

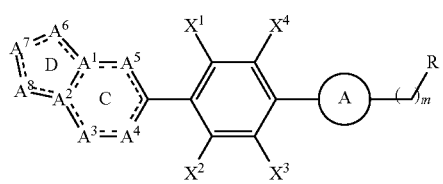

(II)

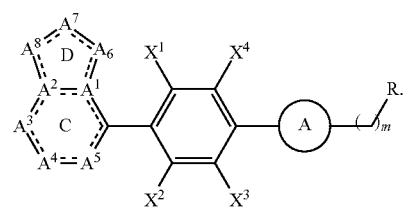

(III)

Preferred embodiment of compound (II) includes, for example, compound (II-1), compound (II-2), compound (II-3), compound (II-4), compound (II-5), compound (II-6) and the like. Compound (II-1) and compound (II-2) are more preferable.

[Chemical Formula 36]

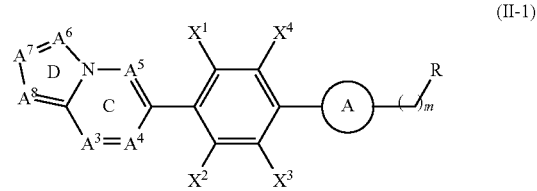

(II-1)

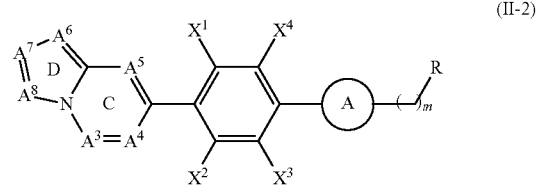

(II-2)

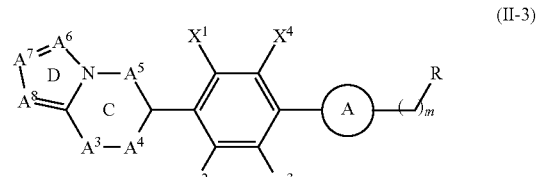

(II-3)

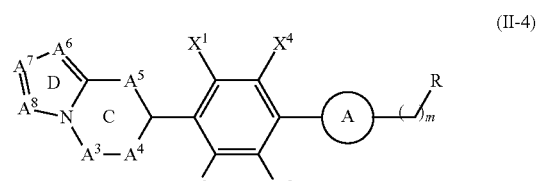

(II-4)

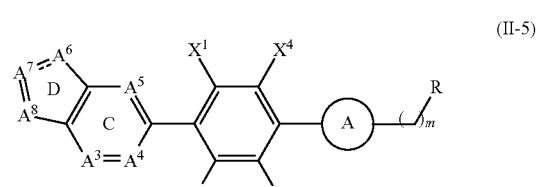

(II-5)

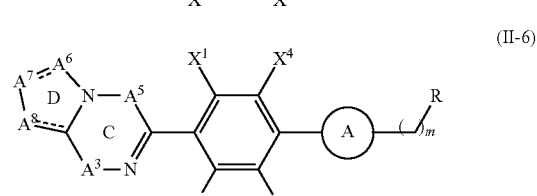

(II-6)

Preferred embodiment of compound (III) includes, for example, compound (III-1), compound (III-2), compound (III-3) and the like.

[Chemical Formula 37]

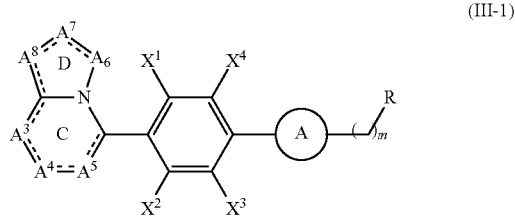

(III-1)

-continued

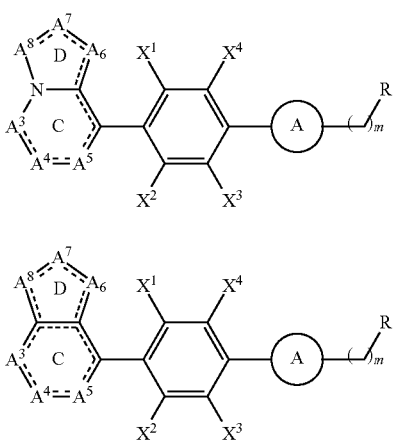

(III-2)

(III-3)

The compound of the formula (I) is further described below.

Ring A may be any group of the formula:

[Chemical Formula 38]

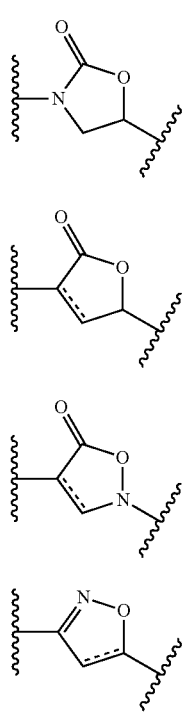

(A-1)

(A-2)

(A-3)

(A-4)

in which dashed line represents presence or absence of a bond, and preferably, represented by the formula (A-1).

In a broad sense, the group-(CH$_2$)mR attached to ring A is an organic residue which is able to bind to the 5-position of the oxazolidinone ring in oxazolidinone antimicrobial agents, and may be any organic group that can be attached to the 5-position of the oxazolidinone ring of an oxazolidinone antimicrobial compound, which was known as disclosed in a reference cited above or can be synthesized by a skilled person or will be found in the future.

Also, the term "oxazolidinone antimicrobial agent" broadly includes antimicrobial compounds having a five-membered ring of the formula (A-2), (A-3) or (A-4), instead of the formula (A-1).

m is 0 or 1, and preferably 1.

R represents, preferably, H, —NHC(=O)R$^A$, —NHC(=S)R$^A$, —NH-het$^1$, —O-het$^1$, —S-het$^1$, —S(=O)-het$^1$, —S(=O)$_2$-het$^1$, het$^2$, —CONHR$^A$, —OH, lower alkyl, lower alkoxy or lower alkenyl. Preferably, R is —NHC(=O)R$^A$, —NHC(=S)R$^A$, —NH-het$^1$, het$^2$, —CONHR$^A$ or —OH. More preferably, R is —NHC(=O)R$^A$ or het$^2$.

R$^A$ is hydrogen, lower alkyl, halogenated lower alkyl, amino, (lower alkyl)amino, lower alkenyl, heterocycle (lower)alkyl, (lower alkyl)carbonyl, (lower alkyl)carbonyl lower alkyl, lower alkoxy, cycloalkyl, cycloalkyl(lower)alkyl, arylcarbonyl, arylcarbonyl(lower)alkyl, heterocyclecarbonyl or heterocyclecarbonyl(lower)alkyl, and preferably, hydrogen, lower alkyl, halogenated lower alkyl, or lower alkoxy.

het$^1$ and het$^2$ are independently optionally substituted heterocyclic group, preferably five- or six-membered, more preferably five- or six-membered heterocyclic group containing at least nitrogen atom, and still more preferably aromatic heterocyclic group such as isoxazole, triazole, tetrazole. Example of substituents for such heterocycle includes lower alkyl, amino and the like.

More preferably, the group —(CH$_2$)mR is any one of the following groups:

[Chemical Formula 39]

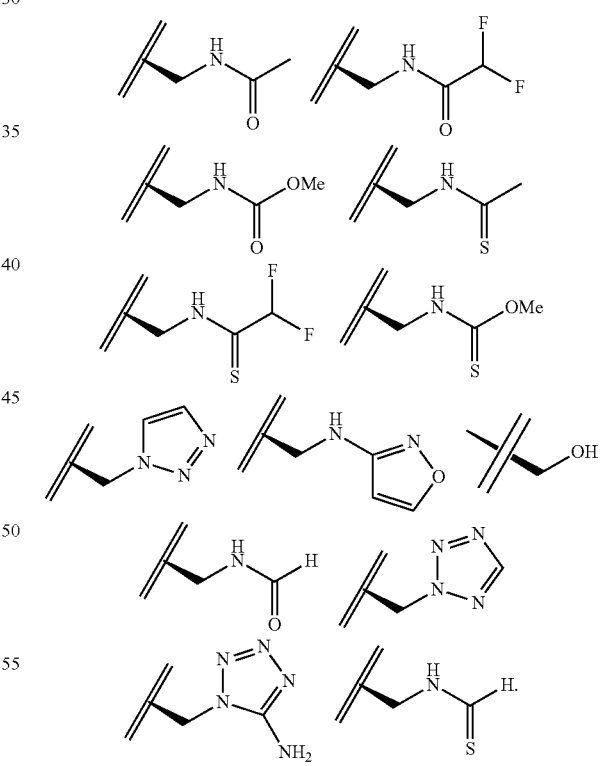

Ring B is a benzene ring optionally substituted. The substituents are exemplified by X$^1$, X$^2$, X$^3$ and X$^4$ as described below, and specifically, include same or different one to four substituent(s) selected from the group consisting of hydrogen, halogen, amino, hydroxy and lower alkyl. Preferably, ring B is a benzene ring optionally substituted with one or two halogen(s).

Ring C is a saturated, unsaturated or aromatic six-membered heterocycle containing at least one nitrogen atom as a ring member, wherein the atom at the point of attachment to ring B is a carbon atom, optionally containing one to three double bond(s) in the ring and optionally substituted. Also, ring C may contain oxygen atom or sulfur atom. When only one of $A^1$ and $A^2$ is nitrogen atom, ring C is an optionally substituted six-membered ring containing two double bonds in the ring.

Preferably, ring C contains carbon atoms and nitrogen atom(s) as a ring member, and the number of the nitrogen atom is 1 or 2. More preferably, any one of $A^1$ and $A^2$ is nitrogen atom and the other is carbon atom, or $A^1$ and $A^2$ are both carbon atoms. Preferably, ring C also contains two or three double bonds in the ring. Particular preferably, only one of $A^1$ and $A^2$ is nitrogen atom and the other ring members of ring C are all carbon atoms, and ring C contains two double bonds in the ring.

Ring D is a saturated, unsaturated or aromatic five-membered ring, preferably five-membered heterocycle, optionally containing one or two double bond(s) in the ring and optionally substituted. Also, ring D may form a fused ring. When ring D forms such fused ring, it is preferably a six- to eight-membered heterocycle, more preferably saturated heterocycle. Such six- to eight-membered heterocycle may be substituted with same or different one to three substituent(s) selected from Substituent Group A.

Ring D consists of atoms preferably selected from the group consisting of carbon atom, nitrogen atom, oxygen atom and sulfur atom, preferably, carbon atom and nitrogen atom. More preferably, the number of the nitrogen atom is one to four, and still more preferably one to three.
Also, ring D preferably contains two double bonds in the ring. In another embodiment, ring D preferably contains one nitrogen atom and oxygen atom(s) or sulfur atom(s) in the ring.

Substituents for ring C and ring D include, preferably, hydrogen, halogen, amino, cyano, hydroxy, lower alkyl or the substituents of Substituent Group A as described below.

Compound (II) is further described below.

[Chemical Formula 40]

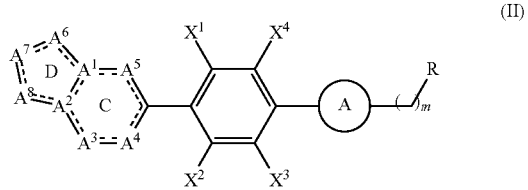

(II)

Ring A, m and R are as defined above.
$X^1$, $X^2$, $X^3$ and $X^4$ are independently hydrogen, halogen, amino, hydroxy or lower alkyl, preferably, hydrogen or halogen. More preferably, $X^1$ and/or $X^2$ is halogen (e.g., fluorine), and $X^3$ and $X^4$ are hydrogen.
$A^1$ is C, $CR^1$ or N;
$A^2$ is C, $CR^2$ or N;
$A^3$ is $CR^3$, $CR^3R^{3\prime}$, N or $NR^{3\prime\prime\prime}$;
$A^4$ is $CR^4$, $CR^4R^{4\prime}$, N or $NR^{4\prime\prime\prime}$;
$A^5$ is $CR^5$, $CR^5R^{5\prime}$, N or $NR^{5\prime\prime\prime}$.
$A^6$ is $CR^6$, $CR^6R^{6\prime}$, N, $NR^{6\prime\prime\prime}$, O or S;
$A^7$ is $CR^7$, $CR^7R^{7\prime}$, N, $NR^{7\prime\prime\prime}$, O or S;
$A^8$ is $CR^8$, $CR^8R^{8\prime}$, N, $NR^{8\prime\prime\prime}$, O or S.
$R^1$, $R^2$, $R^3$, $R^{3\prime}$, $R^4$, $R^{4\prime}$, $R^5$, $R^{5\prime}$, $R^6$, $R^{6\prime}$, $R^7$, $R^{7\prime}$, $R^8$ and $R^{8\prime}$ are independently selected from Substituent Group A as listed below.

Substituent Group A: hydrogen, optionally substituted lower alkyl, optionally substituted lower alkenyl, optionally substituted lower alkoxy, carboxy, optionally substituted carbamoyl, cyano, formyl, optionally substituted (lower alkyl)carbonyl, optionally substituted (lower alkoxy)carbonyl, optionally substituted heterocyclic group (preferably five- or six-membered), optionally substituted heterocyclecarbonyl (preferably five- or six-membered), optionally substituted amino, optionally substituted aminocarbonyl, optionally substituted aryl (preferably, phenyl), optionally substituted arylcarbonyl, (lower alkyl)sulfonyl, (lower alkyl)sulfinyl, halogen.

The substituent of Substituent Group A is preferably hydrogen, optionally substituted lower alkyl, formyl, optionally substituted amino, or optionally substituted aminocarbonyl.

Substituents for "optionally substituted lower alkyl", "optionally substituted lower alkenyl", "optionally substituted lower alkoxy", "optionally substituted (lower alkyl)carbonyl", "optionally substituted (lower alkoxy)carbonyl" in Substituent Group A are preferably halogen, hydroxy, optionally substituted amino or optionally substituted imino (example of substituents: lower alkyl, halogenated lower alkyl, (lower alkyl)thio lower alkyl, lower alkoxy lower alkyl, carbamoyl, (lower alkyl)carbamoyl, (lower alkyl)sulfonyl, (lower alkyl)sulfinyl, (lower alkyl)sulfonyl lower alkyl, (lower alkyl)sulfinyl lower alkyl, (lower alkyl)sulfonylamino, acyl (e.g., formyl, (lower alkyl)carbonyl), optionally substituted heterocyclic group (example of substituents: lower alkyl, aryl lower alkyl), optionally substituted heterocycle (lower)alkyl (example of substituents: lower alkyl, aryl lower alkyl), lower alkenyl, lower alkynyl, C(=NCN)$NHCH_3$, cyano, cyano lower alkyl, cyano (lower alkyl)carbonyl, hydroxy, lower alkoxy, (lower alkoxy)carbonyl, $NHCONH_2$, oxo, optionally substituted lower alkoxy (example of substituents: halogen, hydroxy, amino, (lower alkylamino, arylcarbonyl, heterocyclecarbonyl), halogenated lower alkoxy, hydroxy lower alkoxy, (lower alkyl)thio, hydroxy(lower alkyl)thio, carbamoyl, (lower alkyl)carbamoyl, (lower alkyl)sulfonyl, (lower alkyl)sulfinyl, hydroxy (lower alkyl)sulfonyl, hydroxy(lower alkyl)sulfinyl and cyano, and preferably, halogen, hydroxy, optionally substituted amino. For the heterocyclic group described above, five- or six-membered is preferable.

Substituents for "optionally substituted carbamoyl", "optionally substituted amino" in Substituent Group A preferably include lower alkyl, halogenated lower alkyl, hydroxy lower alkyl, carbamoyl, (lower alkyl)carbamoyl, arylcarbamoyl, heterocyclecarbonyl wherein the heterocycle is preferably five- or six-membered, (lower alkyl)sulfonyl, (lower alkyl)sulfinyl, acyl (e.g., (lower alkyl)carbonyl, hydroxy (lower alkyl)carbonyl), (lower alkoxy)carbonyl, aryl (lower alkoxy)carbonyl, heterocycle (lower alkoxy)carbonyl wherein the heterocycle is preferably five- or six-membered, aryl lower alkyl, heterocycle (lower)alkyl wherein the heterocycle is preferably five- or six-membered. Substituent is preferably lower alkyl or acyl.

Substituents for "optionally substituted heterocyclic group", "optionally substituted heterocyclecarbonyl", "optionally substituted aryl", "optionally substituted arylcarbonyl" in Substituent Group A preferably include lower alkyl, halogen, amino, (lower alkylamino, hydroxy, lower alkoxy, oxo, hydroxy lower alkyl, lower alkoxy lower alkyl, (lower alkylamino lower alkyl and the like, and preferably lower alkyl, halogen, amino, (lower alkylamino, hydroxy, lower alkoxy.

More preferably, the substituent of Substituent Group A is any one of the following substituents described in Example C and other Examples.
[Chemical Formula 41]
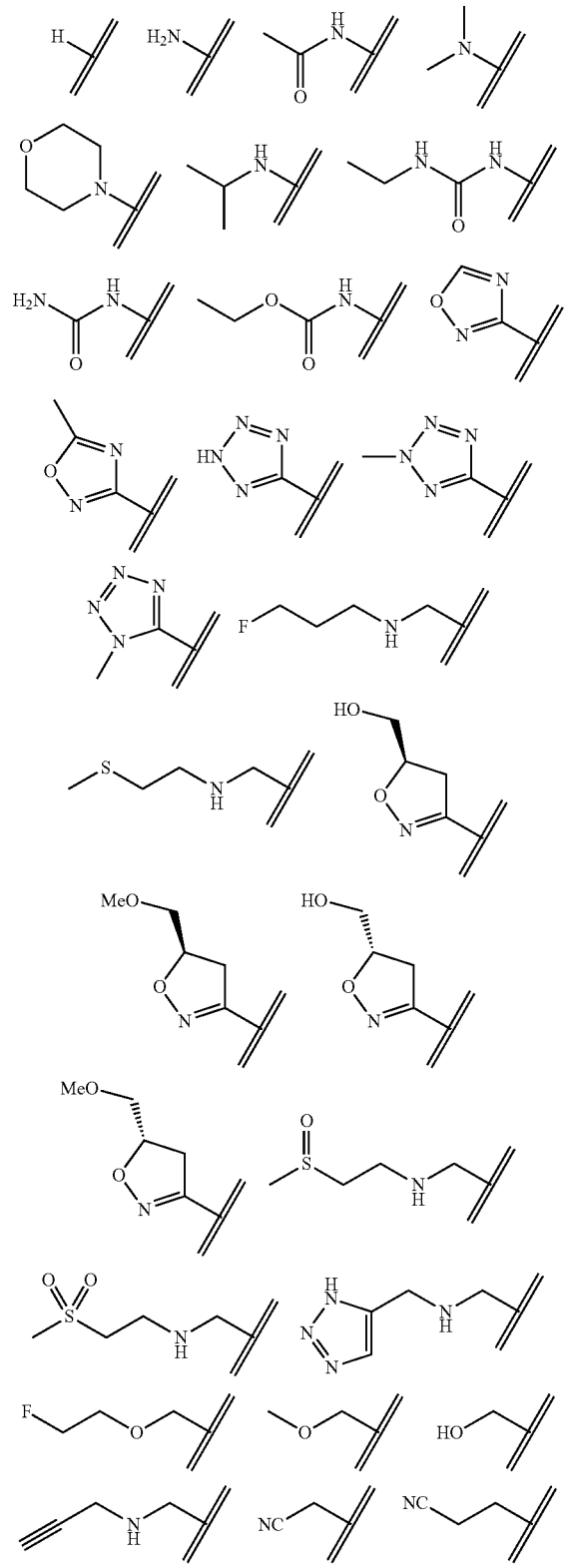
[Chemical Formula 42]
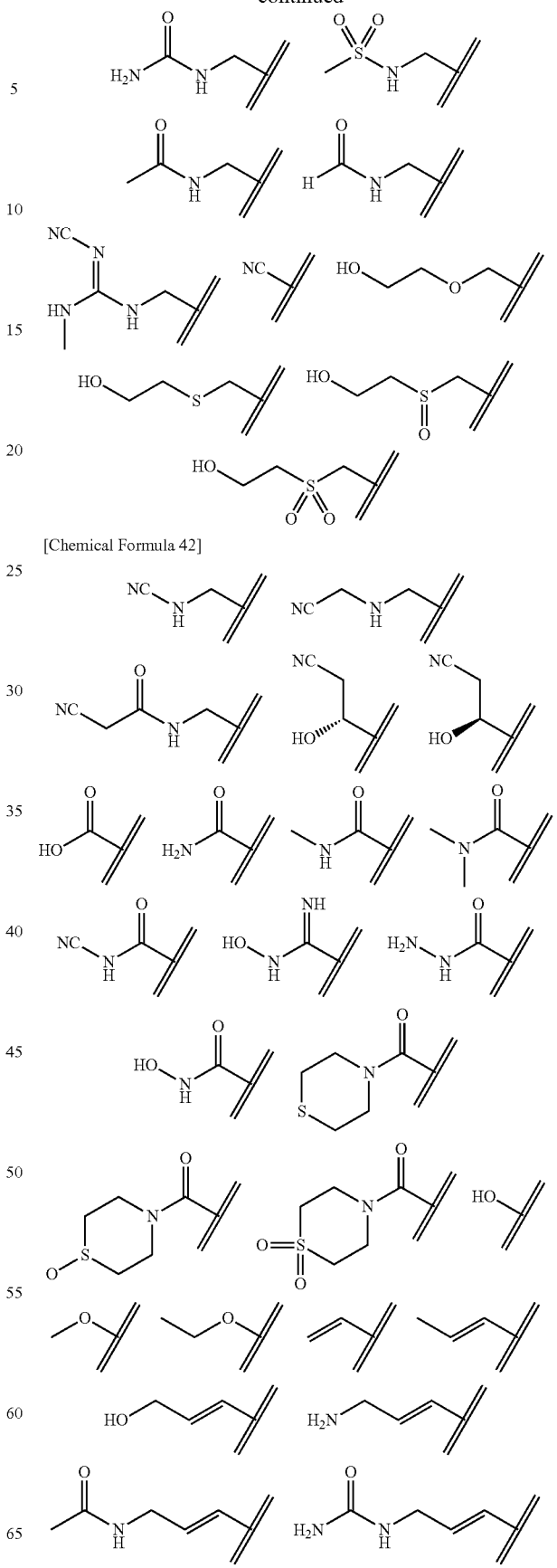

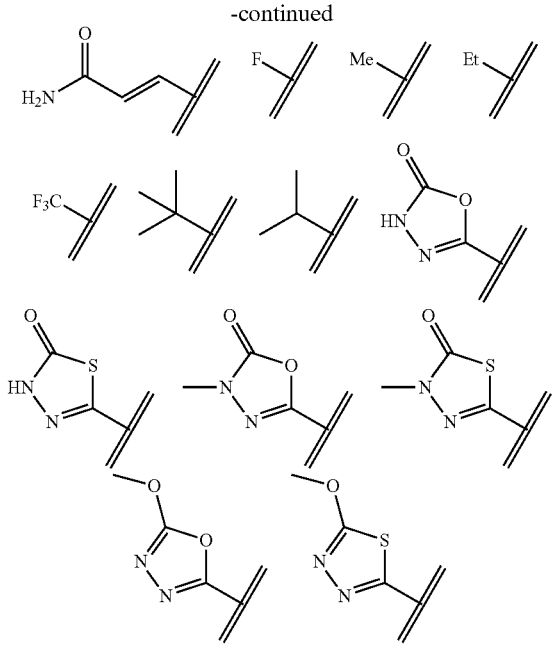

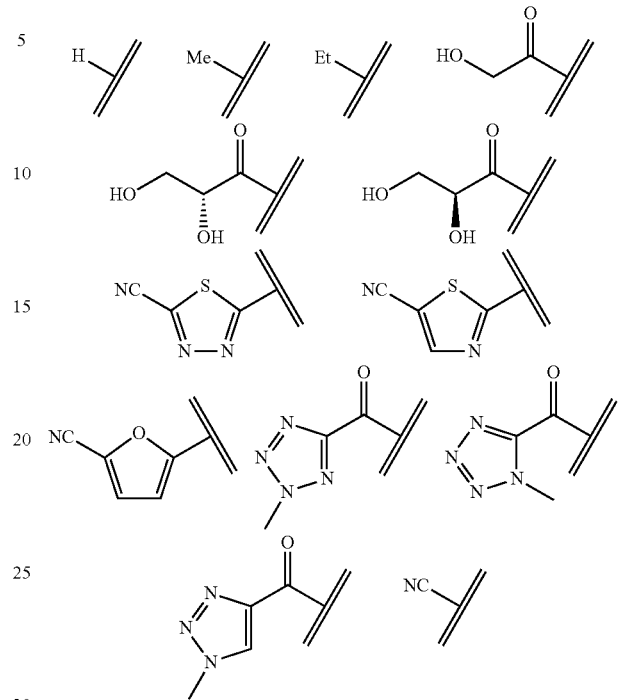

[Chemical Formula 43]

$R^{6''}, R^{7''}, R^{8''}$ =

$R^6$ and $R^{6'}$, $R^7$ and $R^{7'}$, and $R^8$ and $R^{8'}$ may be respectively taken together to form oxo;

$R^{6'''}$ and $R^{7'''}$ may be taken together with the respective adjacent N atom to form a heterocycle optionally substituted;

$R^{7'''}$ and $R^{8'''}$ may be taken together with the respective adjacent N atom to form a heterocycle optionally substituted;

The substituent for such heterocycle optionally substituted is selected from Substituent Group A.

$R^1$ and $R^2$ are preferably hydrogen.

$R^{3'}$, $R^{4'}$ and $R^{5'}$ are preferably hydrogen.

$R^{6'}$, $R^{7'}$ and $R^{8'}$ are preferably hydrogen.

$R^3$, $R^4$ and $R^5$ are preferably hydrogen or lower alkyl, more preferably hydrogen.

$R^6$, $R^7$ and $R^8$ are preferably, hydrogen, optionally substituted lower alkyl, carboxy, optionally substituted carbamoyl, cyano, formyl, optionally substituted heterocyclecarbonyl or optionally substituted amino as defined above for Substituent Group A, and more preferably, substituents as described below in Example C. Also, at least two of $R^6$, $R^7$ and $R^8$ are preferably hydrogen.

$R^6$ and $R^{6'}$, $R^7$ and $R^{7'}$, and $R^8$ and $R^{8'}$ may be respectively taken together to form oxo.

$R^{3'''}$, $R^{4'''}$, $R^{5'''}$, $R^{6'''}$, $R^{7'''}$ and $R^{8'''}$ are independently selected from Substituent Group B.

Substituent Group B: hydrogen, optionally substituted lower alkyl, optionally substituted (lower alkyl)carbonyl, formyl, cyano, amino.

Substituents for "optionally substituted lower alkyl", "optionally substituted (lower alkyl)carbonyl in Substituent Group B preferably include hydroxy, lower alkoxy, amino, (lower alkyl)amino, carbamoyl, (lower alkyl)carbamoyl, and hydroxy is preferable.

$R^{3'''}$, $R^{4'''}$ and $R^{5'''}$ are more preferably hydrogen or lower alkyl (e.g., methyl).

More preferably, $R^{6'''}$, $R^{7'''}$ and $R^{8'''}$ are the following substituents as described in Example E and other Examples. Also, at least one of $R^{6'''}$, $R^{7'''}$ and $R^{8'''}$ is preferably hydrogen. More preferably, $R^{7'''}$ is hydrogen or optionally substituted lower alkyl.

dashed line represents presence or absence of a bond.

The following preferred embodiments are provided.

(1) Only one of $A^1$ and $A^2$ is N. In this case, the dashed line between $A^1$ and $A^2$ represents absence of a bond. More preferably, the other of $A^1$ and $A^2$ is C. More preferably, ring C contains two double bonds in the ring.

(2) $A^1$ and $A^2$ are both carbon atoms, and the dashed line between $A^1$ and $A^2$ represents presence of a bond. In this case, more preferably, any one of $A^3$, $A^4$ and $A^5$ is nitrogen atom.

(3) dashed line between $A^3$ and $A^4$ represents presence of a bond.

(4) dashed line between $A^5$ and the adjacent carbon atom represents presence of a bond.

(5) Only one of $A^1$ and $A^2$ is N. In this case, the dashed line between $A^1$ and $A^2$ represents absence of a bond. Also, any one of $A^3$, $A^4$ and $A^5$ is optionally substituted N atom. More preferably, ring C is a saturated ring or it contains one double bond. Such double bond is preferably present between $A^4$ or $A^5$ and the carbon atom linked to ring B.

The following more preferred embodiments are provided.

(1) $A^3$ is $CR^3$; $A^4$ is $CR^4$; $A^5$ is $CR^5$; $R^3$, $R^4$ and $R^5$ are independently selected from Substituent Group A.

(2) $A^3$ is CH; $A^4$ is CH; $A^5$ is CH; or any one or two of $R^3$, $R^4$ and $R^5$ is selected from Substituent Group A excluding hydrogen.

(3) Any one of $A^3$, $A^4$ and $A^5$ is N.

(4) Any one of $A^3$, $A^4$ and $A^5$ is N; the others are CH optionally substituted with a substituent of Substituent Group A.

(5) Any one of $A^6$, $A^7$ and $A^8$ is N.

(6) $A^6$ and/or $A^8$ is N; $A^7$ is $CR^7$.

(7) Any two of $A^6$, $A^7$ and $A^8$ are N.

(8) $A^7$ and/or $A^8$ is N; $A^6$ is $CR^6$.

(9) $A^6$, $A^7$ and $A^8$ are N.

(10) Any two of $A^6$, $A^7$ and $A^8$ are N and O or N and S.

(11) $A^1$ and $A^2$ are both carbon atoms, any one of $A^3$, $A^4$ and $A^5$ is N, and the others are carbon atoms.

(12) Only one of $A^1$ and $A^2$ is N. In this case, the dashed line between $A^1$ and $A^2$ represents absence of a bond. Also, $A^3$, $A^4$ and $A^5$ are CH. Ring C contains two double bonds in the ring. $A^6$ and $A^8$ are N; $A^7$ is $CR^7$. $R^7$ is preferably hydrogen, optionally substituted lower alkyl, formyl, optionally substituted amino, optionally substituted aminocarbonyl as defined above for Substituent Group A, and more preferably, hydrogen or optionally substituted lower alkyl.

Each compound included in Compound (II) is described below. Substituents for compound (II) are typically as described above.

Compound (II-1) is further described below.

[Chemical Formula 44]

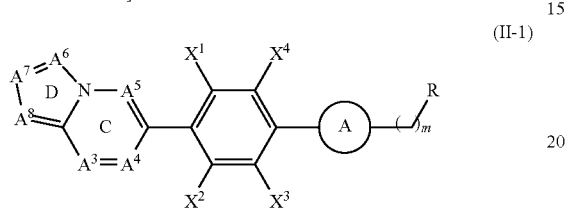

(II-1)

Ring A, m, R, $X^1$, $X^2$, $X^3$ and $X^4$ are as defined above.
$A^3$ is $CR^3$ or N;
$A^4$ is $CR^4$ or N;
$A^5$ is $CR^5$ or N;
$A^6$ is $CR^6$ or N;
$A^7$ is $CR^7$ or N;
$A^8$ is $CR^8$ or N.
$R^3$, $R^4$, $R^5$, $R^6$, $R^7$ and $R^8$ are independently selected from Substituent Group A.

The following preferred embodiments are provided.
(1) $A^3$ is $CR^3$; $A^4$ is $CR^4$; $A^5$ is $CR^5$; $R^3$, $R^4$ and $R^5$ are independently selected from Substituent Group A.
(2) $A^3$ is CH; $A^4$ is CH; $A^5$ is CH; or any one or two of $R^3$, $R^4$ and $R^5$ is selected from Substituent Group A excluding hydrogen.
(3) Any one of $A^3$, $A^4$ and $A^5$ is N.
(4) Any one of $A^3$, $A^4$ and $A^5$ is N; the others are CH optionally substituted with a substituent of Substituent Group A.
(5) Any one of $A^6$, $A^7$ and $A^8$ is N.
(6) $A^6$ and/or $A^8$ is N; $A^7$ is $CR^7$.
(7) Any two of $A^6$, $A^7$ and $A^8$ are N.
(8) $A^7$ and/or $A^8$ is N; $A^6$ is $CR^6$.
(9) $A^6$, $A^7$ and $A^8$ are N.
(10) $A^6$ and $A^8$ are N; $A^7$ is $CR^7$. $R^7$ is preferably hydrogen, optionally substituted lower alkyl, formyl, optionally substituted amino, optionally substituted aminocarbonyl as defined above for Substituent Group A, more preferably, hydrogen or optionally substituted lower alkyl. $A^3$ is CH; $A^4$ is CH; $A^5$ is CH.

The preferred fused ring consisting of ring C and ring D in compound (II-1) is any one of:

[Chemical Formula 45]

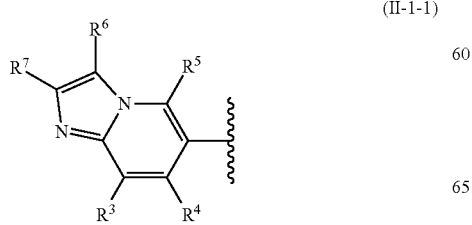

(II-1-1)

-continued

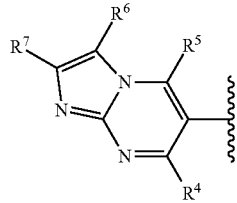

(II-1-2)

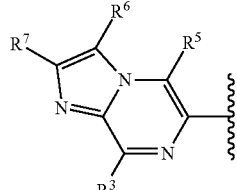

(II-1-3)

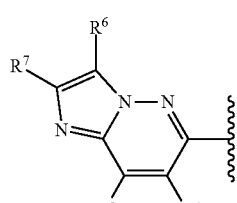

(II-1-4)

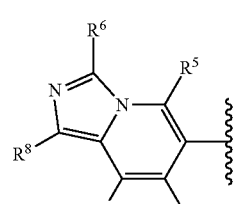

(II-1-5)

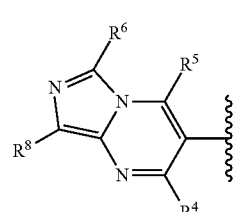

(II-1-6)

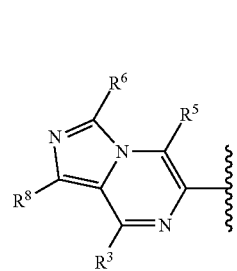

(II-1-7)

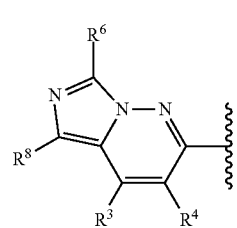

(II-1-8)

(II-1-9) 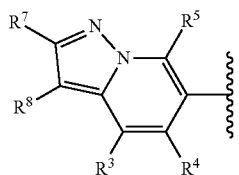

(II-1-10) 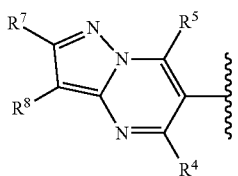

(II-1-11) 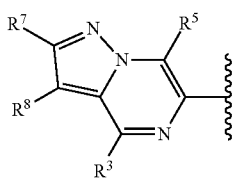

(II-1-12) 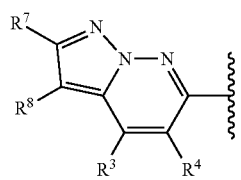

(II-1-13) 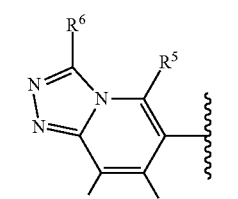

(II-1-14) 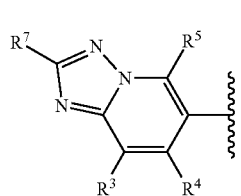

(II-1-15) 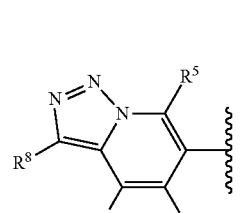

(II-1-16) 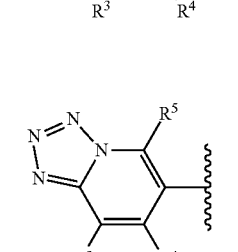

(II-1-17) 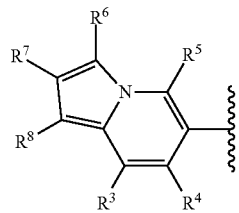

(II-1-18) 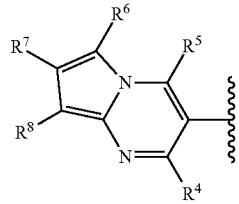

(II-1-19) 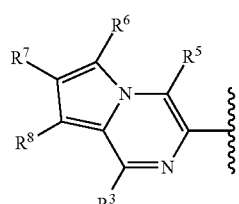

(II-1-20) 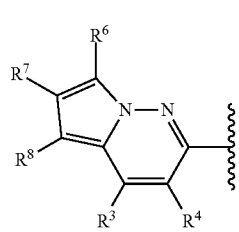

wherein each variable is as defined above.

Compound (II-2) is further described below.

[Chemical Formula 46]

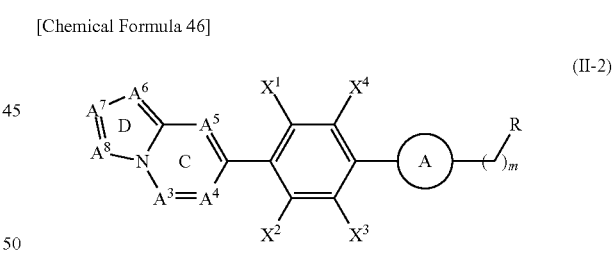

(II-2)

Ring A, m, R, $X^1$, $X^2$, $X^3$ and $X^4$ are as defined above.

$A^3$ is $CR^3$ or N;
$A^4$ is $CR^4$ or N;
$A^5$ is $CR^5$ or N;
$A^6$ is $CR^6$ or N;
$A^7$ is $CR^7$ or N;
$A^8$ is $CR^8$ or N.

$R^3$, $R^4$, $R^5$, $R^6$, $R^7$ and $R^8$ are independently selected from Substituent Group A.

The following preferred embodiments are provided.

(1) $A^3$ is $CR^3$; $A^4$ is $CR^4$; $A^5$ is $CR^5$; $R^3$, $R^4$ and $R^5$ are independently selected from Substituent Group A.

(2) $A^3$ is CH; $A^4$ is CH; $A^5$ is CH; or any one or two of $R^3$, $R^4$ and $R^5$ is selected from Substituent Group A excluding hydrogen.

(3) Any one of $A^3$, $A^4$ and $A^5$ is N.

(4) Any one of $A^3$, $A^4$ and $A^5$ is N; and the others are CH.
(5) Any one of $A^6$, $A^7$ and $A^8$ is N.
(6) $A^6$ and/or $A^8$ is N; $A^7$ is $CR^7$.
(7) Any two of $A^6$, $A^7$ and $A^8$ are N.
(8) $A^7$ and/or $A^8$ is N; and $A^6$ is $CR^6$.
(9) $A^6$, $A^7$ and $A^8$ are N.
(10) $A^6$ and $A^8$ are N; and $A^7$ is $CR^7$. $R^7$ is preferably hydrogen, optionally substituted lower alkyl, formyl, optionally substituted amino, optionally substituted aminocarbonyl as defined above for Substituent Group A, and more preferably, hydrogen or optionally substituted lower alkyl. $A^3$ is CH; $A^4$ is CH; and $A^5$ is CH.

In compound (II-2), preferred fused ring consisting of ring C and ring D is any one of:

[Chemical Formula 47]

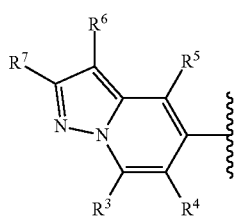
(II-2-1)

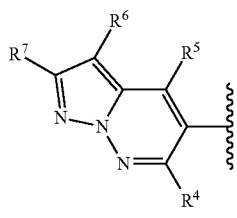
(II-2-2)

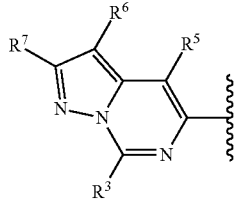
(II-2-3)

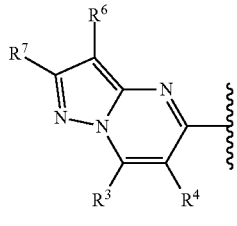
(II-2-4)

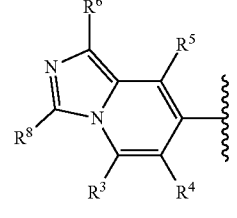
(II-2-5)

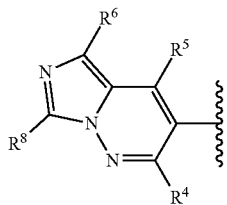
(II-2-6)

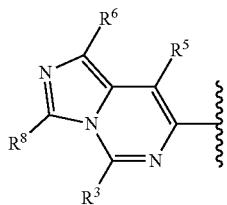
(II-2-7)

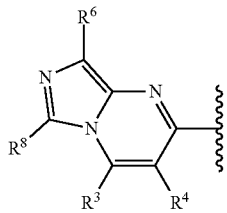
(II-2-8)

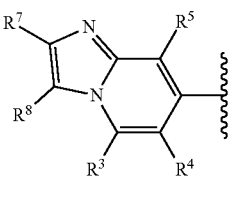
(II-2-9)

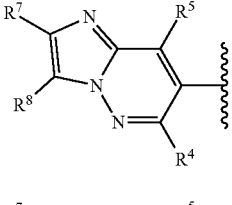
(II-2-10)

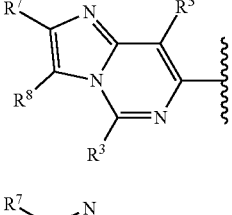
(II-2-11)

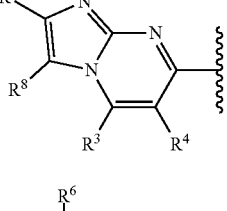
(II-2-12)

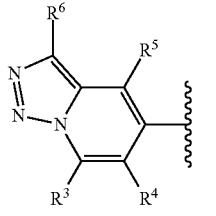
(II-2-13)

-continued (II-2-14)
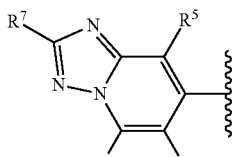

(II-2-15)
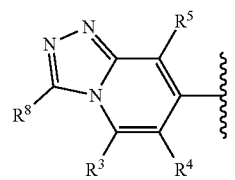

(II-2-16)
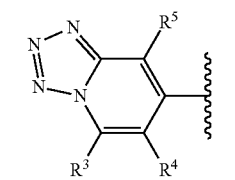

(II-2-17)
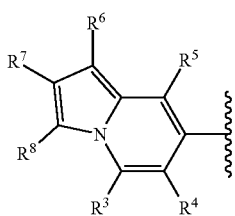

(II-2-18)
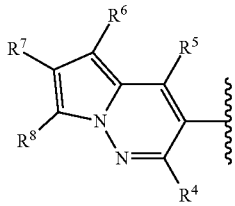

(II-2-19)
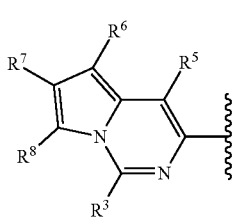

(II-2-20)
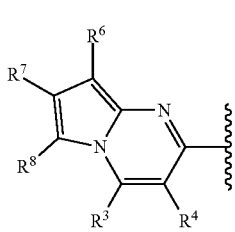

wherein each variable is as defined above.

Compound (II-3) is further described below.

[Chemical Formula 48]

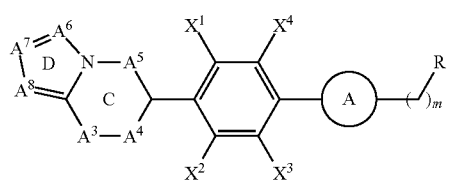
(II-3)

Ring A, m, R, $X^1$, $X^2$, $X^3$ and $X^4$ are as defined above.
$A^3$ is $CR^3R^{3'}$ or $NR^{3''}$;
$A^4$ is $CR^4R^{4'}$ or $NR^{4''}$;
$A^5$ is $CR^5R^{5'}$ or $NR^{5''}$.
Preferably, at least one of $A^3$, $A^4$ and $A^5$ contains nitrogen atom.
$A^6$ is $CR^6$ or N;
$A^7$ is $CR^7$ or N;
$A^8$ is $CR^8$ or N.
$R^3$, $R^{3'}$, $R^4$, $R^{4'}$, $R^5$, $R^{5'}$, $R^6$, $R^7$ and $R^8$ are independently selected from Substituent Group A.
$R^{3''}$, $R^{4''}$ and $R^{5''}$ are independently selected from Substituent Group B.

The following preferred embodiments are provided.
(1) Any one of $A^3$, $A^4$ and $A^5$ contains nitrogen atom, and any one or two of $A^6$, $A^7$ and $A^8$ is N.

In compound (II-3), preferred fused ring consisting of ring C and ring D is any one of:

[Chemical Formula 49]

(II-3-1)
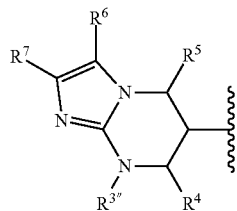

(II-3-2)
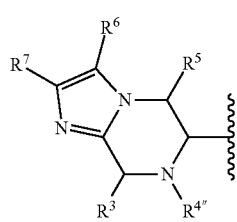

(II-3-3)
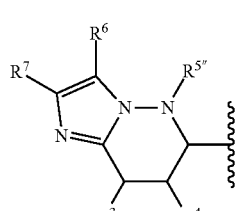

(II-3-4)
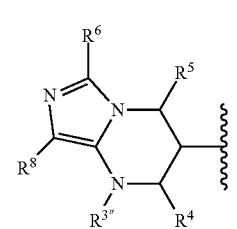

(II-3-5)
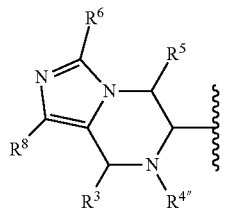
(II-3-6)
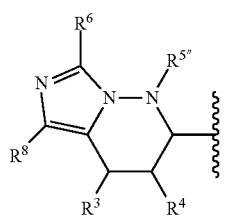
(II-3-7)
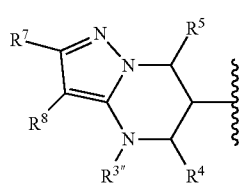
(II-3-8)
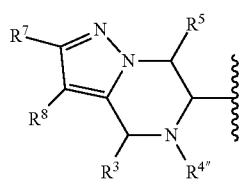
(II-3-9)
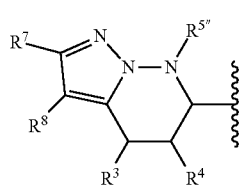
(II-3-10)
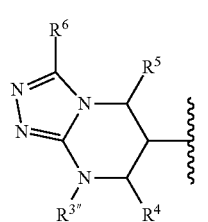
(II-3-11)
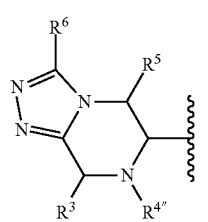
(II-3-12)
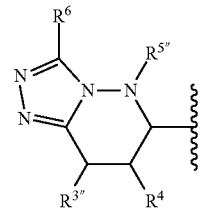
(II-3-13)
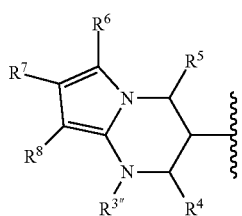
(II-3-14)
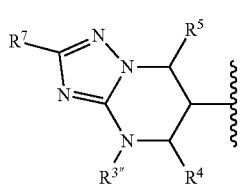
(II-3-15)
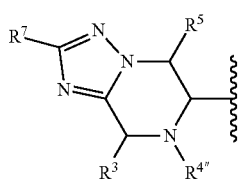
(II-3-16)
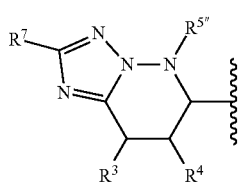
(II-3-17)
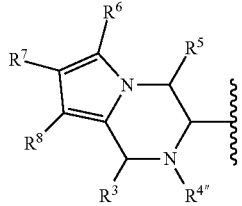
(II-3-18)
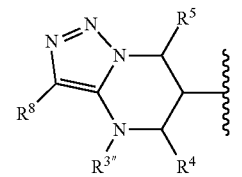
(II-3-19)
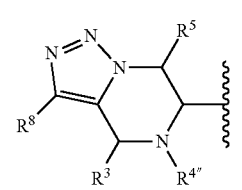

-continued (II-3-20)
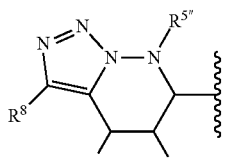

(II-3-21)
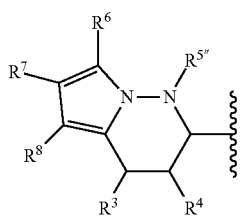

wherein each variable is as defined above.

Compound (II-4) is further described below.

[Chemical Formula 50]

(II-4)
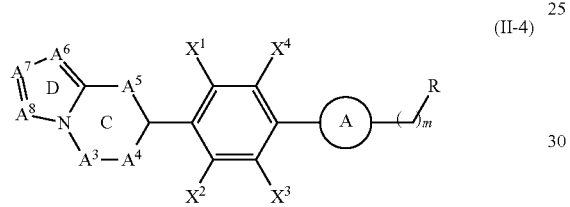

Ring A, m, R, $X^1$, $X^2$, $X^3$ and $X^4$ are as defined above.

$A^3$ is $CR^3R^{3\prime}$ or $NR^{3\prime\prime}$;

$A^4$ is $CR^4R^{4\prime}$ or $NR^{4\prime\prime}$;

$A^5$ is $CR^5R^{5\prime}$ or $NR^{5\prime\prime}$.

Preferably, at least one of $A^3$, $A^4$ and $A^5$ contains nitrogen atom.

$A^6$ is $CR^6$ or N;

$A^7$ is $CR^7$ or N;

$A^8$ is $CR^8$ or N.

$R^3$, $R^4$, $R^5$, $R^6$, $R^7$ and $R^8$ are independently selected from Substituent Group A.

Preferred embodiments are provided below.

(1) Any one of $A^3$, $A^4$ and $A^5$ contains nitrogen atom, and any one or two of $A^6$, $A^7$ and $A^8$ is N.

In compound (II-4), preferred fused ring consisting of ring C and ring D is any one of:

[Chemical Formula 51]

(II-4-1)
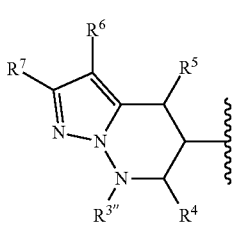

(II-4-2)
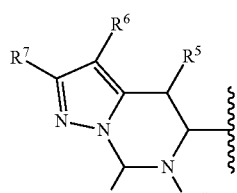

(II-4-3)
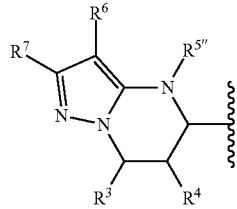

(II-4-4)
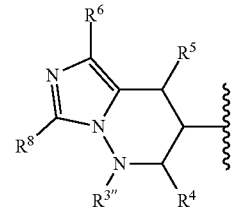

(II-4-5)
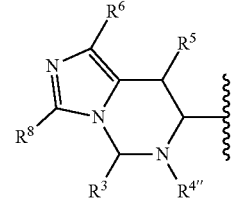

(II-4-6)
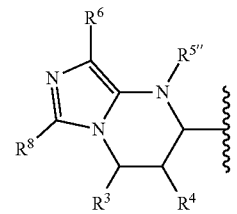

(II-4-7)
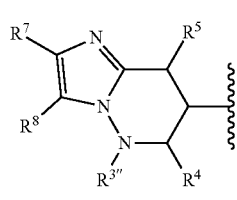

(II-4-8)
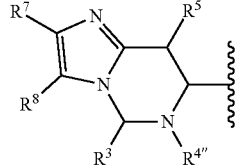

(II-4-9) 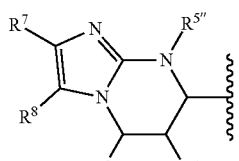

(II-4-10) 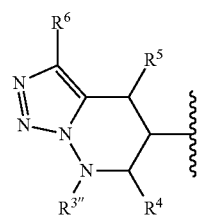

(II-4-11) 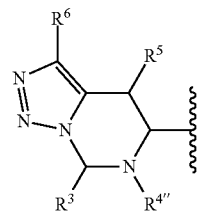

(II-4-12) 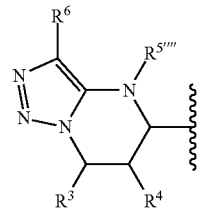

(II-4-13) 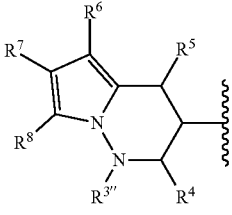

(II-4-14) 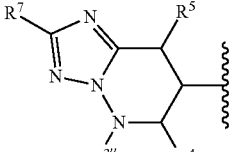

(II-4-15) 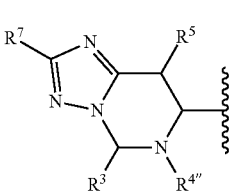

(II-4-16) 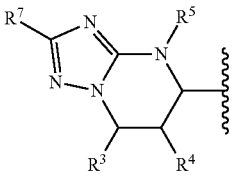

(II-4-17) 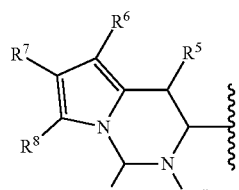

(II-4-18) 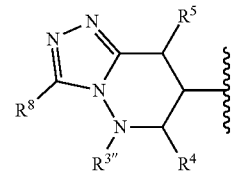

(II-4-19) 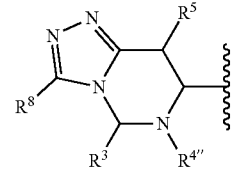

(II-4-20) 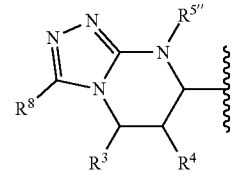

(II-4-21) 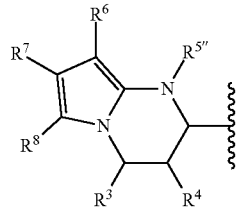

wherein each variable is as defined above.
Compound (II-5) is further described below.

[Chemical Formula 52]

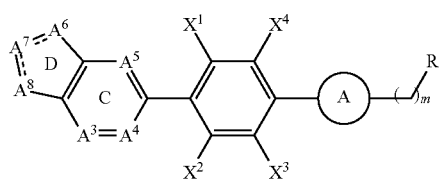

(II-5)

Ring A, m, R, $X^1$, $X^2$, $X^3$ and $X^4$ are as defined above.
$A^3$ is $CR^3$ or N;
$A^4$ is $CR^4$ or N;
$A^5$ is $CR^5$ or N.
Preferably, at least one of $A^3$, $A^4$ and $A^5$ contains nitrogen atom.
$A^6$ is $CR^6$, $CR^6R^{6\prime}$, N, $NR^{6\prime\prime}$, O or S;
$A^7$ is $CR^7$, $CR^7R^{7\prime}$, N, $NR^{7\prime\prime}$, O or S;
$A^8$ is $CR^8$, $CR^8R^{8\prime}$, N, $NR^{8\prime\prime}$, O or S.
$R^3$, $R^4$, $R^5$, $R^6$, $R^{6\prime}$, $R^7$, $R^{7\prime}$, $R^8$ and $R^{8\prime}$ are independently selected from Substituent Group A.

$R^6$ and $R^{6'}$, $R^7$ and $R^{7'}$, and $R^8$ and $R^{8'}$ may be respectively taken together to form oxo.

$R^{6''}$, $R^{7''}$ and $R^{8''}$ are independently selected from Substituent Group B.

dashed line represents presence or absence of a bond.

The following preferred embodiments are provided.

(1) Any one or two of $A^3$, $A^4$ and $A^5$ is nitrogen atom, and any one of $A^6$, $A^7$ and $A^8$ contains nitrogen atom.

(2) Any two of $A^6$, $A^7$ and $A^8$ are nitrogen atom and oxygen atom, or nitrogen atom and sulfur atom. Each nitrogen atom is optionally substituted.

(3) Either dashed line between $A^6$ and $A^7$ or $A^7$ and $A^8$ represents presence of a bond.

In compound (II-5), preferred fused ring consisting of ring C and ring D is any one of:

[Chemical Formula 53]

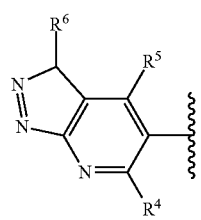
(II-5-1)

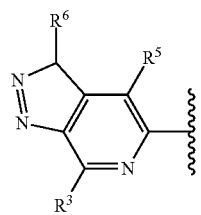
(II-5-2)

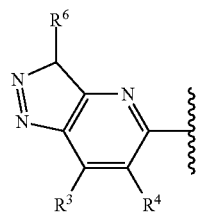
(II-5-3)

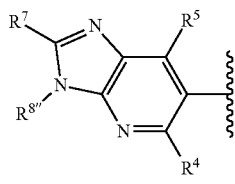
(II-5-4)

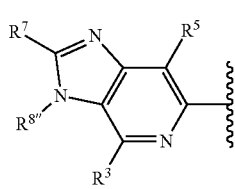
(II-5-5)

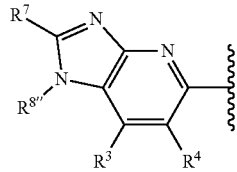
(II-5-6)

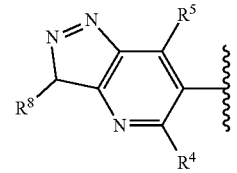
(II-5-7)

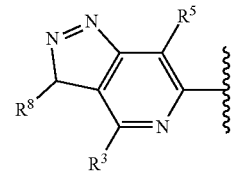
(II-5-8)

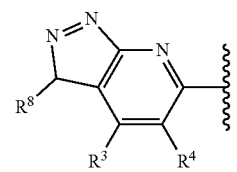
(II-5-9)

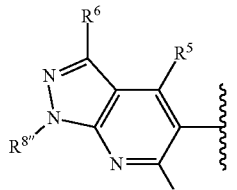
(II-5-10)

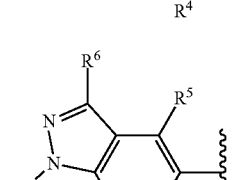
(II-5-11)

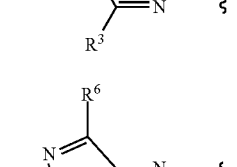
(II-5-12)

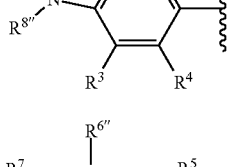
(II-5-13)

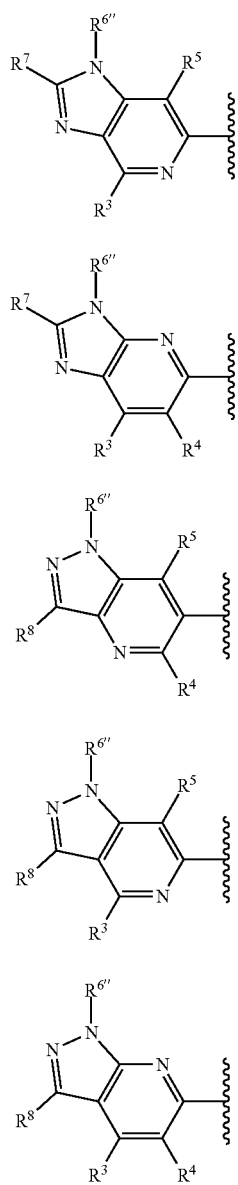
(II-5-14)
(II-5-15)
(II-5-16)
(II-5-17)
(II-5-18)
[Chemical Formula 54]
(II-5-19)
(II-5-20)
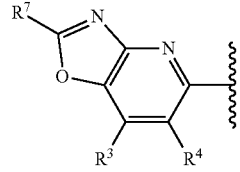 (II-5-21)
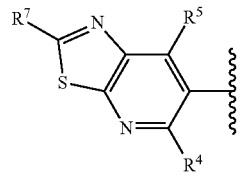 (II-5-22)
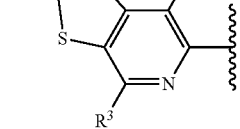 (II-5-23)
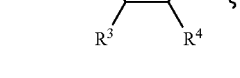 (II-5-24)
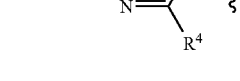 (II-5-25)
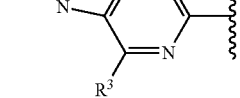 (II-5-26)
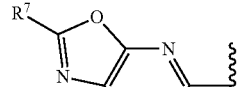 (II-5-27)
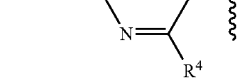 (II-5-28)

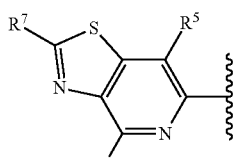 (II-5-29)
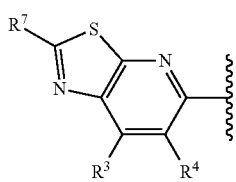 (II-5-30)
[Chemical Formula 55]
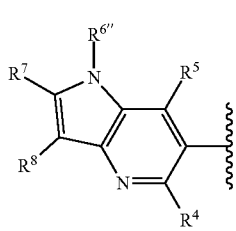 (II-5-31)
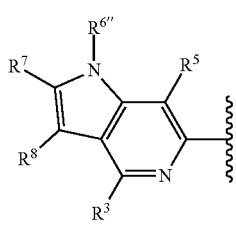 (II-5-32)
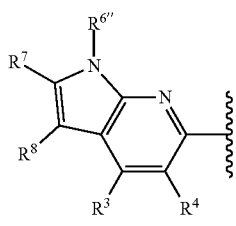 (II-5-33)
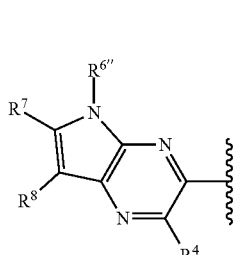 (II-5-34)
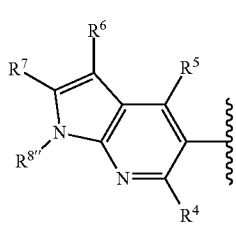 (II-5-35)
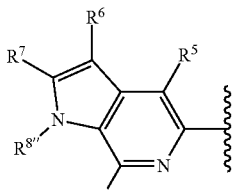 (II-5-36)
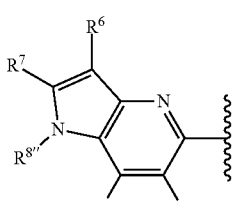 (II-5-37)
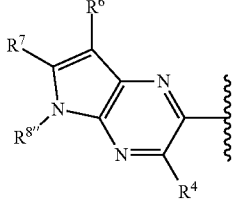 (II-5-38)
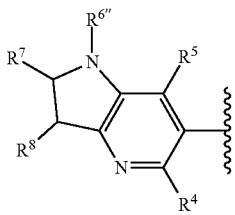 (II-5-39)
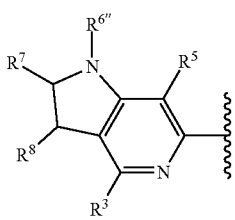 (II-5-40)
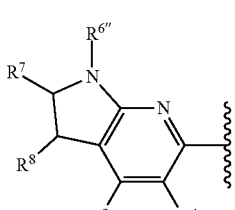 (II-5-41)
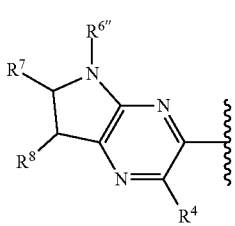 (II-5-42)

-continued

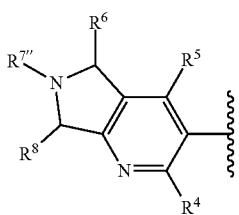 (II-5-43)

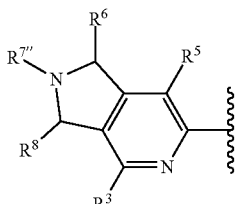 (II-5-44)

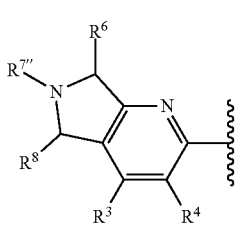 (II-5-45)

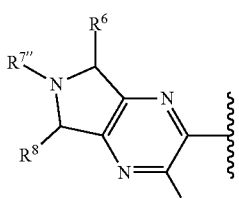 (II-5-46)

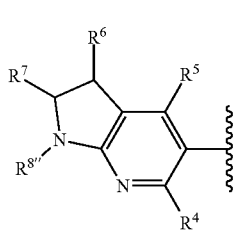 (II-5-47)

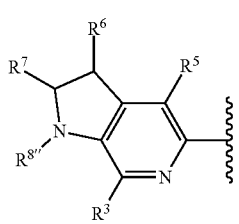 (II-5-48)

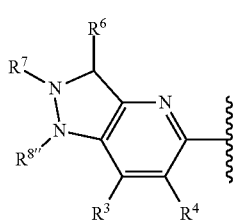 (II-5-49)

-continued

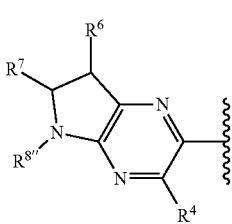 (II-5-50)

wherein each variable is as defined above.
Compound (II-6) is further described below.

[Chemical Formula 56]

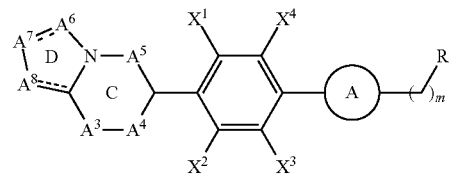 (II-6)

wherein
ring A, m, R, $X^1$, $X^2$, $X^3$ and $X^4$ are as defined above;
$A^3$ is $CR^3R^{3'}$ or $NR^{3''}$;
$A^5$ is $CR^5R^{5'}$ or $NR^{5''}$;
$A^6$ is $CR^6$, $CR^6R^{6'}$, N, $NR^{6''}$, O or S;
$A^7$ is $CR^7$, $CR^7R^{7'}$, N, $NR^{7''}$, O or S;
$A^8$ is $CR^8$, $CR^8R^{8'}$, N, $NR^{8''}$, O or S;
$R^3$, $R^{3'}$, $R^5$, $R^{5'}$, $R^6$, $R^{6'}$, $R^7$, $R^{7'}$, $R^8$ and $R^{8'}$ are independently selected from Substituent Group A; or
$R^6$ and $R^{6'}$, $R^7$ and $R^{7'}$, and $R^8$ and $R^{8'}$ are respectively taken together to form oxo;
$R^{3''}$, $R^{5''}$, $R^{6''}$, $R^{7''}$ and $R^{8''}$ are independently selected from Substituent Group B;
dashed line represents presence or absence of a bond.
Preferably, $A^3$ is $CHR^3$; $A^5$ is $CHR^5$; $A^6$ is $CR^6$; $A^7$ is N; $A^8$ is $CR^8$; and ring D contains two double bonds in the ring.

Compound (III) is further described below. The substituents for compound (III) is typically as described above for compound (II).

[Chemical Formula 57]

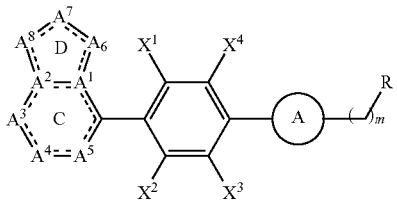 (III)

Ring A, m, R, $X^1$, $X^2$, $X^3$ and $X^4$ are as defined above.
$A^1$ is C, $CR^1$ or N;
$A^2$ is C, $CR^2$ or N;
$A^3$ is $CR^3$, $CR^3R^{3'}$, N or $NR^{3''}$;
$A^4$ is $CR^4$, $CR^4R^{4'}$, N or $NR^{4''}$;
$A^5$ is $CR^5$, $CR^5R^{5'}$, N or $NR^{5''}$.
$A^6$ is $CR^6$, $CR^6R^{6'}$, N, $NR^{6''}$, O or S;
$A^7$ is $CR^7$, $CR^7R^{7'}$, N, $NR^{7''}$, O or S;
$A^8$ is $CR^8$, $CR^8R^{8'}$, N, $NR^{8''}$, O or S.

$R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$ and $R^{8'}$ are independently selected from Substituent Group A.

Substituent Group A: hydrogen, optionally substituted lower alkyl, optionally substituted lower alkenyl, optionally substituted lower alkoxy, carboxy, optionally substituted carbamoyl, cyano, formyl, optionally substituted (lower alkyl)carbonyl, optionally substituted (lower alkoxy)carbonyl, optionally substituted heterocyclic group, optionally substituted heterocyclecarbonyl, optionally substituted amino, optionally substituted aminocarbonyl, optionally substituted aryl, optionally substituted arylcarbonyl, (lower alkyl)sulfonyl, (lower alkyl)sulfinyl, halogen.

Substituent for "optionally substituted lower alkyl", "optionally substituted lower alkenyl", "optionally substituted lower alkoxy", "optionally substituted (lower alkyl) carbonyl", "optionally substituted (lower alkoxy)carbonyl" in Substituent Group A includes preferably halogen, hydroxy, optionally substituted amino or optionally substituted imino (example of substituents: lower alkyl, halogenated lower alkyl, (lower alkyl)thio lower alkyl, lower alkoxy lower alkyl, carbamoyl, (lower alkyl)carbamoyl, (lower alkyl)sulfonyl, (lower alkyl)sulfinyl, (lower alkyl)sulfonyl lower alkyl, (lower alkyl)sulfinyl lower alkyl, acyl (e.g., formyl, (lower alkyl)carbonyl), heterocycle (lower)alkyl, lower alkenyl, lower alkynyl, $C(=NCN)NHCH_3$, cyano, cyano lower alkyl, cyano (lower alkyl)carbonyl, hydroxy), oxo, lower alkoxy, halogenated lower alkoxy, hydroxy lower alkoxy, (lower alkyl)thio, hydroxy(lower alkyl)thio, carbamoyl, (lower alkyl)carbamoyl, (lower alkyl)sulfonyl, (lower alkyl)sulfinyl, hydroxy(lower alkyl)sulfonyl, hydroxy(lower alkyl)sulfinyl, cyano.

Substituent for "optionally substituted carbamoyl", "optionally substituted amino" in Substituent Group A includes preferably lower alkyl, halogenated lower alkyl, carbamoyl, (lower alkyl)carbamoyl, (lower alkyl)sulfonyl, (lower alkyl)sulfinyl, acyl (e.g., (lower alkyl)carbonyl), (lower alkoxy)carbonyl. Also, substituent on carbamoyl may be taken together with the nitrogen atom of carbamoyl to form optionally substituted heterocycle (e.g., five- to seven-membered).

Substituent for "optionally substituted heterocyclic group", "optionally substituted heterocyclecarbonyl", "optionally substituted aryl", "optionally substituted arylcarbonyl" in Substituent Group A includes preferably lower alkyl, halogen, amino, (lower alkyl)amino, hydroxy, lower alkoxy, oxo, hydroxy lower alkyl, lower alkoxy lower alkyl, (lower alkyl)amino lower alkyl and the like.

$R^1$ and $R^2$ are preferably hydrogen.
$R^{3'}$, $R^{4'}$ and $R^{5'}$ are preferably hydrogen.
$R^{6'}$, $R^{7'}$ and $R^{8'}$ are preferably hydrogen.
$R^3$, $R^4$ and $R^5$ are preferably hydrogen or lower alkyl.
$R^6$, $R^7$ and $R^8$ are preferably hydrogen, optionally substituted lower alkyl, carboxy, optionally substituted carbamoyl, cyano, formyl, optionally substituted heterocyclecarbonyl or optionally substituted amino as defined above for Substituent Group A.

$R^6$ and $R^{6'}$, $R^7$ and $R^{7'}$, and $R^8$ and $R^{8'}$ may be respectively taken together to form oxo.

$R^{3''}$, $R^{4''}$, $R^{5''}$, $R^{6''}$, $R^{7''}$ and $R^{8''}$ are independently selected from Substituent Group B.

Substituent Group B: hydrogen, optionally substituted lower alkyl, optionally substituted (lower alkyl)carbonyl.

Substituent for "optionally substituted lower alkyl", "optionally substituted (lower alkyl)carbonyl" in Substituent Group B includes hydroxy, lower alkoxy, amino, (lower alkyl)amino, carbamoyl, (lower alkyl)carbamoyl.

dashed line represents presence or absence of a bond

The following preferred embodiments are provided.
(1) Only one of $A^1$ and $A^2$ is N. In this case, the dashed line between $A^1$ and $A^2$ represents absence of a bond. More preferably, the other of $A^1$ and $A^2$ is C. More preferably, ring C contains two double bonds in the ring.
(2) $A^1$ and $A^2$ are both carbon atoms, and the dashed line between $A^1$ and $A^2$ represents presence of a bond. In this case, more preferably, any one of $A^3$, $A^4$ and $A^5$ is nitrogen atom.
(3) dashed line between $A^3$ and $A^4$ represents presence of a bond.
(4) dashed line between $A^5$ and the adjacent carbon atom represents presence of a bond.

The following more preferred embodiments are provided.
(1) $A^3$ is $CR^3$; $A^4$ is $CR^4$; $A^5$ is $CR^5$; $R^3$, $R^4$ and $R^5$ are independently selected from Substituent Group A.
(2) $A^3$ is CH; $A^4$ is CH; $A^5$ is CH; or any one or two of $R^3$, $R^4$ and $R^5$ is selected from Substituent Group A excluding hydrogen.
(3) Any one of $A^3$, $A^4$ and $A^5$ is N.
(4) Any one of $A^3$, $A^4$ and $A^5$ is N; the others are CH optionally substituted with a group selected from Substituent Group A.
(5) Any one of $A^6$, $A^7$ and $A^8$ is N.
(6) $A^6$ and/or $A^8$ is N; $A^7$ is $CR^7$.
(7) Any two of $A^6$, $A^7$ and $A^8$ are N.
(8) $A^7$ and/or $A^8$ is N; $A^6$ is $CR^6$.
(9) $A^6$, $A^7$ and $A^8$ are N.
(10) Any two of $A^6$, $A^7$ and $A^8$ are N and O, or N and S.
(11) $A^1$ and $A^2$ are both carbon atoms, and any one of $A^3$, $A^4$ and $A^5$ is N.

Compound (III-1) is further described below.

[Chemical Formula 58]

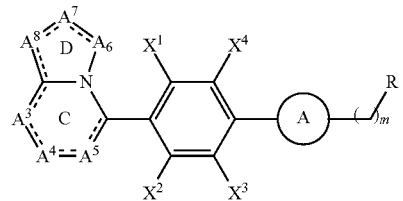

(III-1)

Ring A, m, R, $X^1$, $X^2$, $X^3$ and $X^4$ are as defined above.
$A^3$ is $CR^3$, $CR^3R^{3'}$, N or $NR^{3''}$;
$A^4$ is $CR^4$, $CR^4R^{4'}$, N or $NR^{4''}$;
$A^5$ is $CR^5$, $CR^5R^{5'}$, N or $NR^{5''}$.
$A^6$ is $CR^6$, $CR^6R^{6'}$, N, $NR^{6''}$, O or S;
$A^7$ is $CR^7$, $CR^7R^{7'}$, N, $NR^{7''}$, O or S;
$A^8$ is $CR^8$, $CR^8R^{8'}$, N, $NR^{8''}$, O or S.
$R^3$, $R^{3'}$, $R^4$, $R^{4'}$, $R^5$, $R^{5'}$, $R^6$, $R^{6'}$, $R^7$, $R^{7'}$, $R^8$ and $R^{8'}$ are independently selected from Substituent Group A.
$R^6$ and $R^{6'}$, $R^7$ and $R^{7'}$, and $R^8$ and $R^{8'}$ may be respectively taken together to form oxo.
$R^{3''}$, $R^{4''}$, $R^{5''}$, $R^{6''}$, $R^{7''}$ and $R^{8''}$ are independently selected from Substituent Group B.
dashed line represents presence or absence of a bond.

The following preferred embodiments are provided.
(1) $A^3$ is $CR^3$; $A^4$ is $CR^4$; $A^5$ is $CR^5$, $R^3$, $R^4$ and $R^5$ are preferably hydrogen or lower alkyl.
(2) Any one of $R^6$, $R^7$ and $R^8$ is preferably N.
(3) Ring C preferably contains two double bonds.
(4) Ring D preferably contains two double bonds.

Compound (III-1) is preferably represented by the formulae:
[Chemical Formula 59]
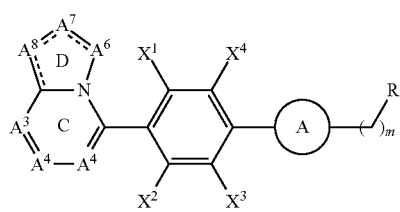
(III-1')
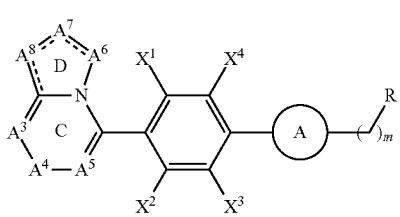
(III-1″)
wherein each variable is as defined above.
In compound (III-1), preferred fused ring consisting of ring C and ring D is any one of:
[Chemical Formula 60]
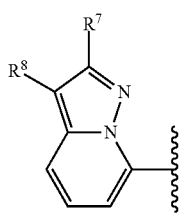
(III-1-1)
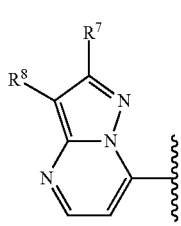
(III-1-2)
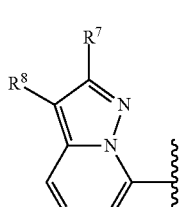
(III-1-3)
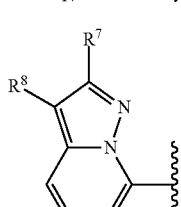
(III-1-4)
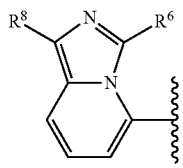
(III-1-5)
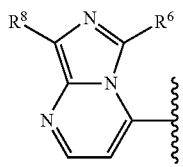
(III-1-6)
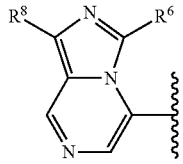
(III-1-7)
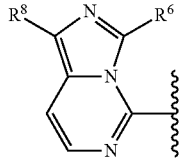
(III-1-8)
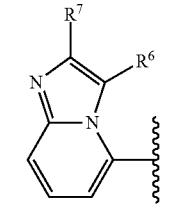
(III-1-9)
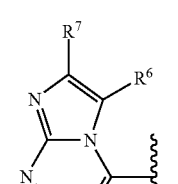
(III-1-10)
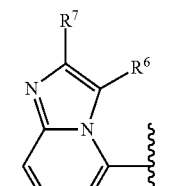
(III-1-11)
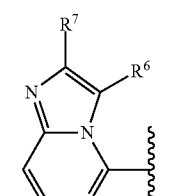
(III-1-12)

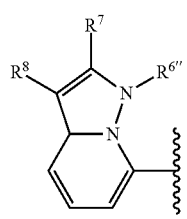 (III-1-13)
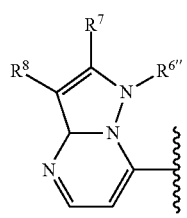 (III-1-14)
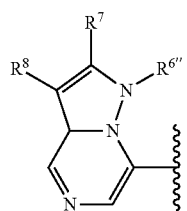 (III-1-15)
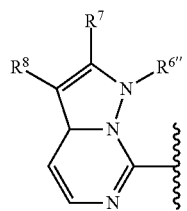 (III-1-16)
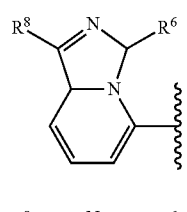 (III-1-17)
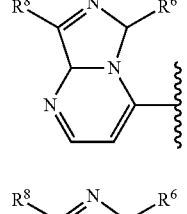 (III-1-18)
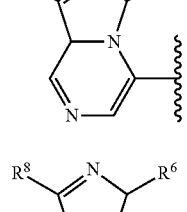 (III-1-19)
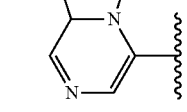 (III-1-20)
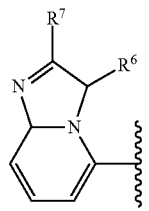 (III-1-21)
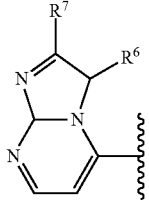 (III-1-22)
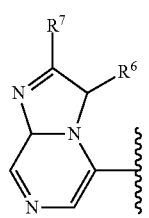 (III-1-23)
(III-1-24)
[Chemical Formula 61]
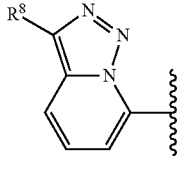 (III-1-25)
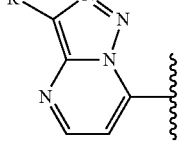 (III-1-26)
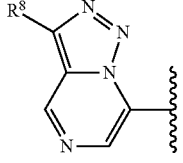 (III-1-27)
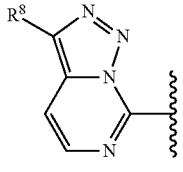 (III-1-28)

(III-1-29) 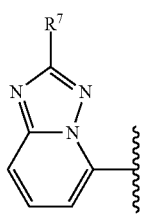
(III-1-30) 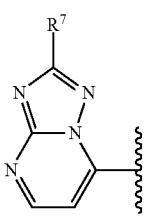
(III-1-31) 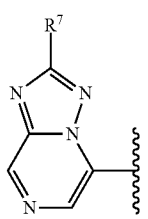
(III-1-32) 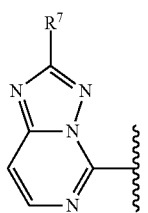
(III-1-33) 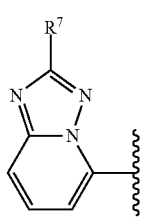
(III-1-34) 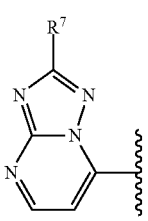
(III-1-35) 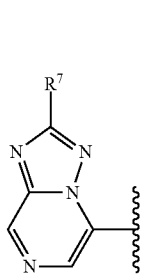
(III-1-36) 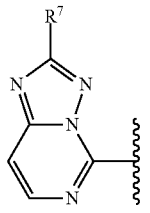
(III-1-37) 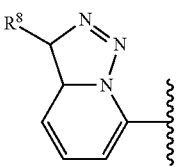
(III-1-38) 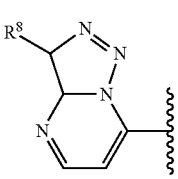
(III-1-39) 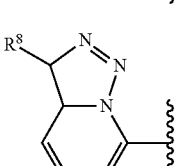
(III-1-40) 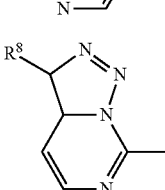
(III-1-41) 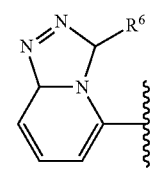
(III-1-42) 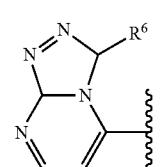
(III-1-43) 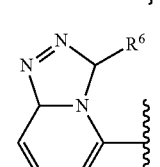
(III-1-44) 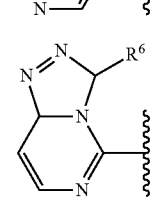
wherein each variable is as defined above.

Compound (III-2) is further described below.

[Chemical Formula 62]

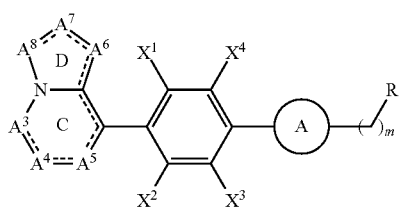
(III-2)

Ring A, m, R, $X^1$, $X^2$, $X^3$ and $X^4$ are as defined above.

$A^3$ is $CR^3$, $CR^3R^{3'}$, N or $NR^{3''}$;

$A^4$ is $CR^4$, $CR^4R^{4'}$, N or $NR^{4''}$;

$A^5$ is $CR^5$, $CR^5R^{5'}$, N or $NR^{5''}$.

$A^6$ is $CR^6$, $CR^6R^{6'}$, N, $NR^{6''}$, O or S;

$A^7$ is $CR^7$, $CR^7R^{7'}$, N, $NR^{7''}$, O or S;

$A^8$ is $CR^8$, $CR^8R^{8'}$, N, $NR^{8''}$, O or S.

$R^3$, $R^{3'}$, $R^4$, $R^{4'}$, $R^5$, $R^{5'}$, $R^6$, $R^{6'}$, $R^7$, $R^{7'}$, $R^8$ and $R^{8'}$ are independently selected from Substituent Group A.

$R^6$ and $R^{6'}$, $R^7$ and $R^{7'}$, and $R^8$ and $R^{8'}$ may be respectively taken together to form oxo.

$R^{3''}$, $R^{4''}$, $R^{5''}$, $R^{6''}$, $R^{7''}$ and $R^{8''}$ are independently selected from Substituent Group B.

dashed line represents presence or absence of a bond

Preferred embodiments are provided below.

(1) $A^3$ is $CR^3$; $A^4$ is $CR^4$; $A^5$ is $CR^5$, $R^3$, $R^4$ and $R^5$ are preferably hydrogen or lower alkyl.

(2) Any one of $R^6$, $R^7$ and $R^8$ is preferably N.

(3) Ring C preferably contains two double bonds.

(4) Ring D preferably contains two double bonds.

Compound (III-2) is preferably represented by the formulae:

[Chemical Formula 63]

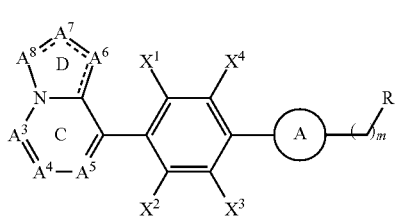
(III-2')

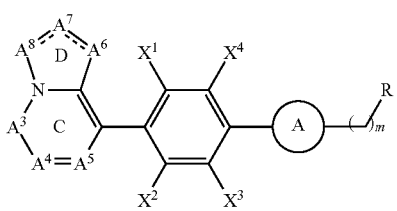
(III-2'')

wherein each variable is as defined above.

In compound (III-2), preferred fused ring consisting of ring C and ring D is any one of:

[Chemical Formula 64]

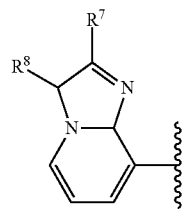
(III-2-1)

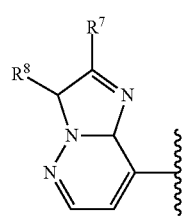
(III-2-2)

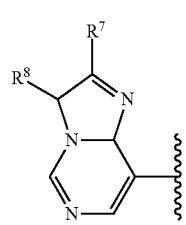
(III-2-3)

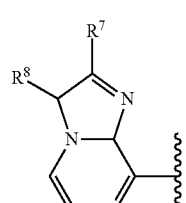
(III-2-4)

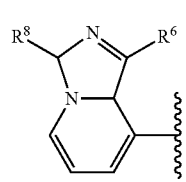
(III-2-5)

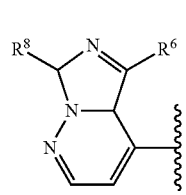
(III-2-6)

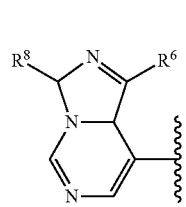
(III-2-7)

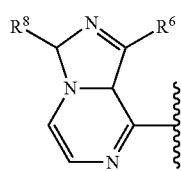 (III-2-8)
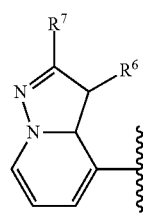 (III-2-9)
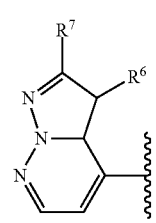 (III-2-10)
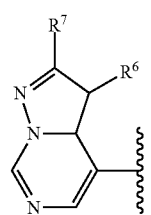 (III-2-11)
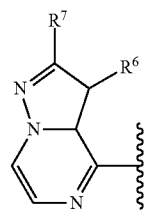 (III-2-12)
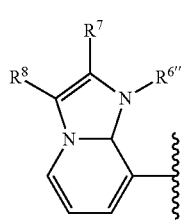 (III-2-13)
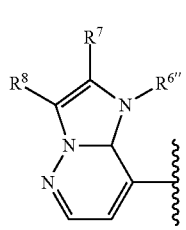 (III-2-14)
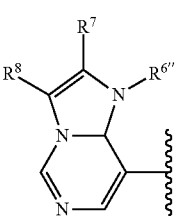 (III-2-15)
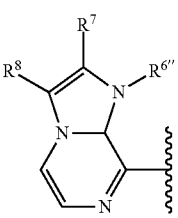 (III-2-16)
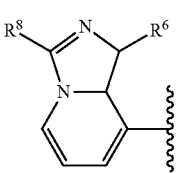 (III-2-17)
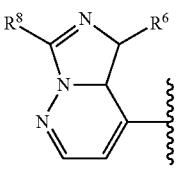 (III-2-18)
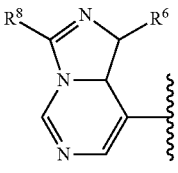 (III-2-19)
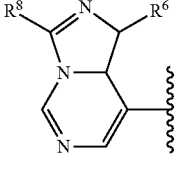 (III-2-20)
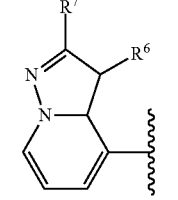 (III-2-21)
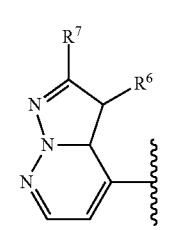 (III-2-22)

(III-2-23) 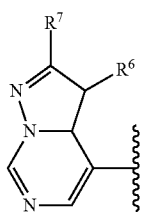
(III-2-24) 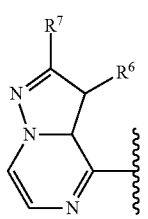
[Chemical Formula 65]
(III-2-25)
(III-2-26)
(III-2-27)
(III-2-28)
(III-2-29)
(III-2-30)
(III-2-31) 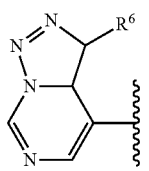
(III-2-32) 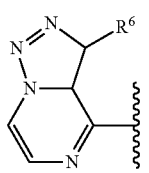
(III-2-33) 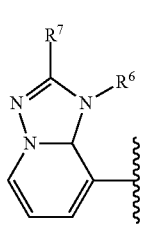
(III-2-34) 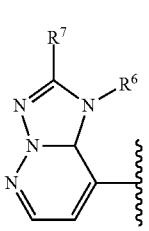
(III-2-35) 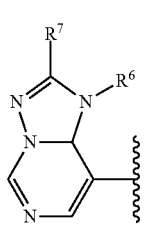
(III-2-36) 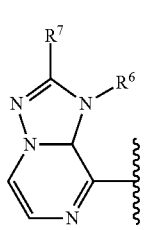
(III-2-37) 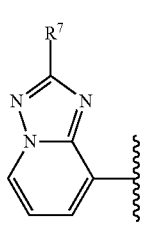

-continued (III-2-38) 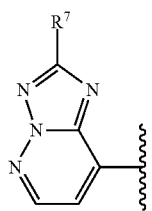

(III-2-39) 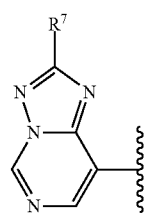

(III-2-40) 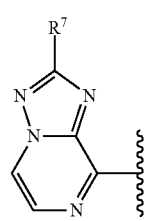

(III-2-41) 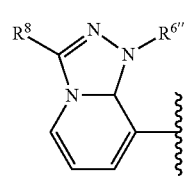

(III-2-42) 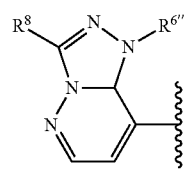

(III-2-43) 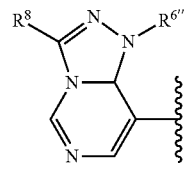

(III-2-44) 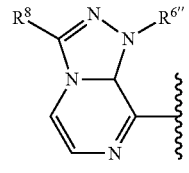

(III-2-45) 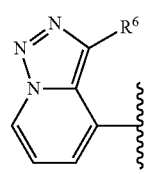

-continued (III-2-46) 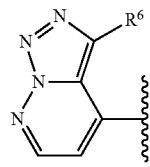

(III-2-47) 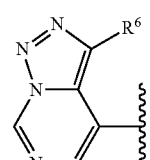

(III-2-48) 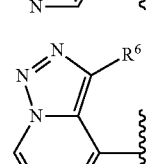

wherein each variable is as defined above.

Compound (III-3) is further described below.

[Chemical Formula 66]

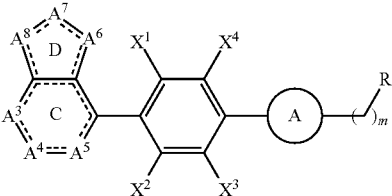
(III-3)

Ring A, m, R, $X^1$, $X^2$, $X^3$ and $X^4$ are as defined above.

$A^3$ is $CR^3$, $CR^3R^{3'}$, N or $NR^{3''}$;

$A^4$ is $CR^4$, $CR^4R^{4'}$, N or $NR^{4''}$;

$A^5$ is $CR^5$, $CR^5R^{5'}$, N or $NR^{5''}$.

Preferably, at least one of $A^3$, $A^4$ and $A^5$ is N.

$A^6$ is $CR^6$, $CR^6R^{6'}$, N, $NR^{6''}$, O or S;

$A^7$ is $CR^7$, $CR^7R^{7'}$, N, $NR^{7''}$, O or S;

$A^8$ is $CR^8$, $CR^8R^{8'}$, N, $NR^{8''}$, O or S.

$R^3$, $R^{3'}$, $R^4$, $R^{4'}$, $R^5$, $R^{5'}$, $R^6$, $R^{6'}$, $R^7$, $R^{7'}$, $R^8$ and $R^{8'}$ are independently selected from Substituent Group A.

$R^6$ and $R^{6'}$, $R^7$ and $R^{7'}$, and $R^8$ and $R^{8'}$ may be respectively taken together to form oxo.

$R^{3''}$, $R^{4''}$, $R^{5''}$, $R^{6''}$, $R^{7''}$ and $R^{8''}$ are independently selected from Substituent Group B.

dashed line represents presence or absence of a bond.

The following preferred embodiments are provided.

(1) $A^3$ is $CR^3$; $A^4$ is $CR^4$; $A^5$ is $CR^5$, $R^3$, $R^4$ and $R^5$ are preferably hydrogen or lower alkyl.

(2) Any one of $R^6$, $R^7$ and $R^8$ is N.

(3) Ring C preferably contains three double bonds.

(4) Ring D preferably contains two double bonds.

(5) Any one of $R^3$, $R^4$ and $R^5$ is N.

(6) Any two of $A^6$, $A^7$ and $A^8$ are nitrogen atom and oxygen atom or nitrogen atom and sulfur atom. Each nitrogen atom is optionally substituted.

(7) Either dashed line between $A^6$ and $A^7$ or $A^7$ and $A^8$ represents presence of a bond.

Compound (III-3) is preferably represented by the formulae:
[Chemical Formula 67]
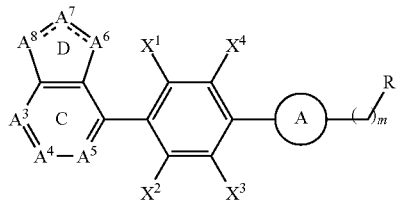
(III-3')
wherein each variable is as defined above.
In compound (III-3), preferred fused ring consisting of ring C and ring D is any one of:
[Chemical Formula 68]
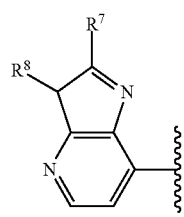
(III-3-2)
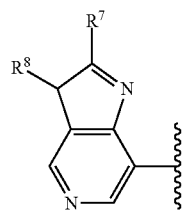
(III-3-3)
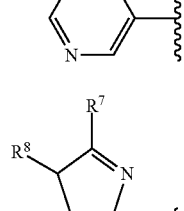
(III-3-4)
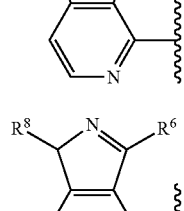
(III-3-6)
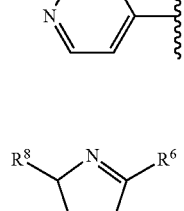
(III-3-7)
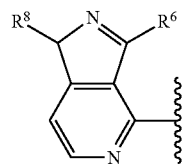
(III-3-8)
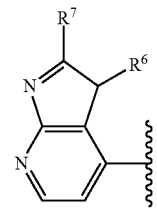
(III-3-10)
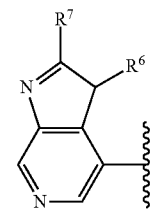
(III-3-11)
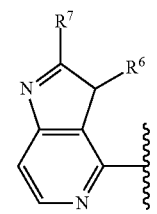
(III-3-12)
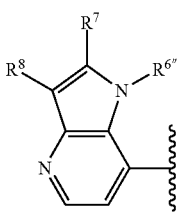
(III-3-14)
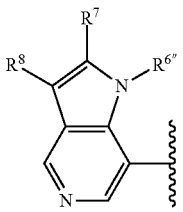
(III-3-15)
(III-3-16)

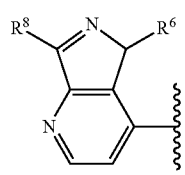
(III-3-18)
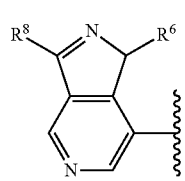
(III-3-19)
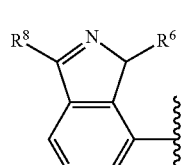
(III-3-20)
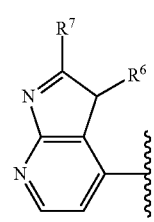
(III-3-22)
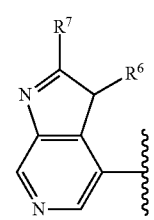
(III-3-23)
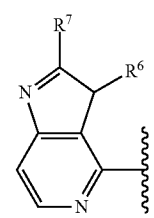
(III-3-24)
[Chemical Formula 69]
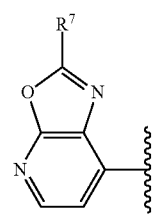
(III-3-25)
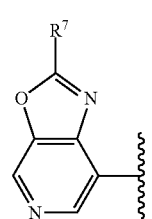
(III-3-26)
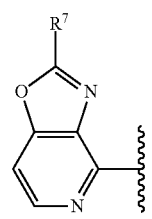
(III-3-27)
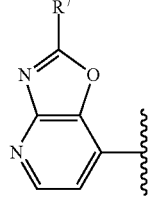
(III-3-28)
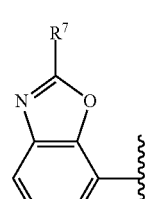
(III-3-29)
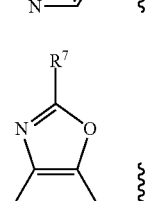
(III-3-30)
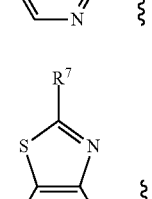
(III-3-31)
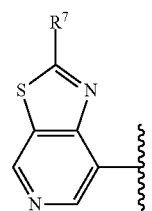
(III-3-32)

-continued

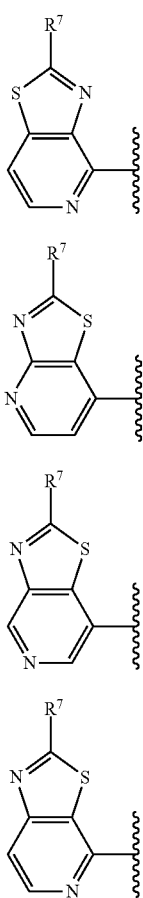

(III-3-33)

(III-3-34)

(III-3-35)

(III-3-36)

wherein each variable is as defined above.

Particularly, the most distinctive feature of the compound of the formula (I) is the C-D ring moiety, which can contribute to improvement of antimicrobial activity, water solubility, in vivo pharmacokinetics and safety, etc.

Main features of the compound of the invention are as follows.
(1) The C-D ring moiety is a 6-5 fused ring.
(2) Ring C is heterocycle.
(3) Ring C contains at least one nitrogen atom as a ring member.
(4) The atom of ring C at the point of attachment to ring B is carbon atom.

More preferably,
(5) When only $A^1$ or $A^2$ is nitrogen atom in ring C, ring C contains two double bonds in the ring.
(6) The antimicrobial activity is improved by the presence of a hetero atom in the C-D ring moiety.
(7) A substituent may be present on the C-D ring moiety.
(8) The structure described above provides improvement of antimicrobial activity, and more preferably, as well as water solubility, oral absorbability, in vivo pharmacokinetics, safety, etc.

Typical procedures for the synthesis of the compound of the invention are described below.
(Method 1)

The compound of the invention can be prepared according to the procedures as described below. The reagents and conditions used in the reactions can be selected appropriately by a skilled person in the art, for example, as described in WO2007/114326.

[Chemical Formula 70]

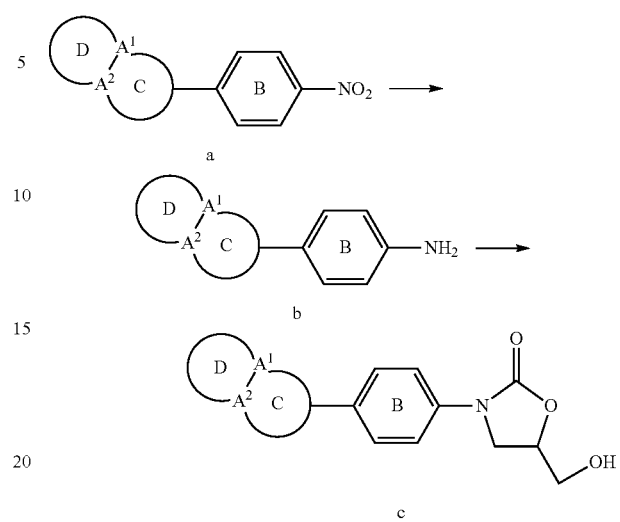

wherein each variable is as defined above.

(1) The nitro group of compound (a) is reduced to afford compound (b) according to any method for reduction, e.g., by hydrogenation with a catalyst such as platinum oxide, Raney nickel, palladium on carbon or the like, or by a reaction using iron powder and hydrochloric acid, acetic acid or the like. Compound (a) is commercially available or can be prepared easily from a reagent commercially available.

(2) Compound (b) is urethanated using di-tert-butyl dicarbonate in an appropriate organic solvent, such as methanol, THF, etc., or urethanated using benzyloxycarbonyl chloride in water or an organic solvent, such as acetone, methanol, THF or a mixture thereof, in the presence of a base, such as triethylamine, potassium carbonate, sodium carbonate, sodium bicarbonate, etc. The resulting compound is then treated with a base, such as n-butyllithium, in an appropriate aprotic organic solvent, such as THF, N,N-dimethylformamide, etc., at a temperature from −78° C. to the reflux temperature of the solvent, and followed by reaction with glycidyl butyrate to afford compound (c).

(3) Compound (c) may be further converted to compound (g) as shown in the following scheme:

[Chemical Formula 71]

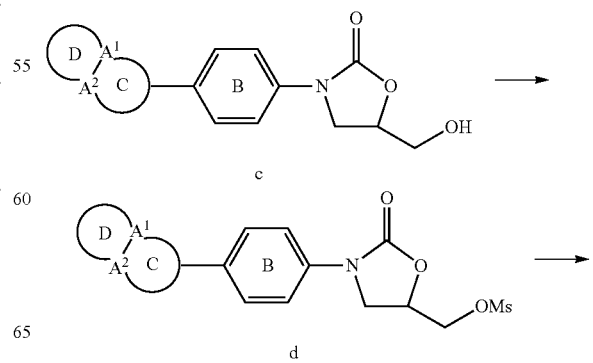

-continued

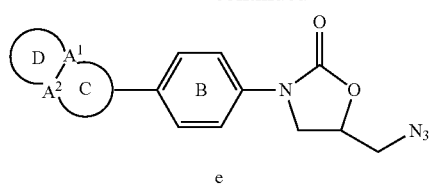

e

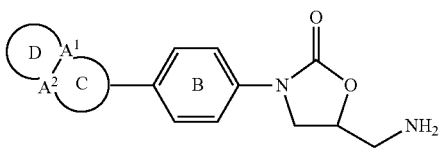

f

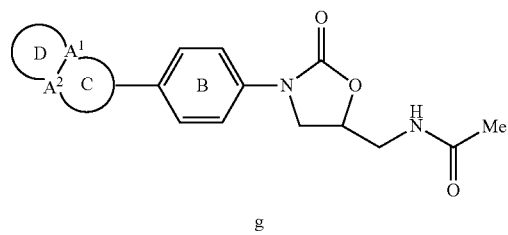

g wherein each variable is as defined above.

(4) Compound (c) is reacted with methanesulfonyl chloride in the presence of a base, such as triethylamine, in an organic solvent, such as dichloromethane, THF, etc., at a temperature from ice-cooling to the reflux temperature of the solvent to afford compound (d).

(5) Compound (d) is reacted with sodium azide in an organic solvent, such as THF, N,N-dimethylformamide, etc., at a temperature from ice-cooling to the reflux temperature of the solvent to afford compound (e).

(6) The azide group of compound (e) is reduced to afford compound (f) by any appropriate method for reduction, e.g., by hydrogenation reduction with a catalyst, such as platinum oxide, palladium on carbon or the like, or by using triphenylphosphine and water.

(7) Compound (f) is acylated with an appropriate acid anhydride, such as acetic anhydride, in a basic solvent, such as pyridine, to afford compound (g).

(Method 2)

[Chemical Formula 72]

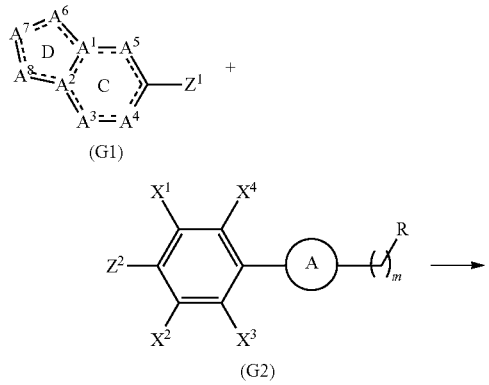

-continued (II)

wherein each variable is as defined above, with the proviso that compound (G1) contains a double bond between the carbon atom connected to $Z^1$ and $A^4$ or $A^5$.

Compound (II) may be preferably obtained by reacting compound (G1) with compound (G2) in the presence of a palladium catalyst under basic condition.

In the above scheme, $Z^1$ and $Z^2$ may be suitable group to be removed during the palladium-catalyzed coupling reaction. For example, halo (Cl, Br, I), trifluoromethylsulfonyloxy, trimethylstannyl, triallkoxysilyl, boronic acid residue (e.g., alkylboronic acids, cyclic boronic acids).

The coupling reaction can be conducted according to the method, for example, as described in S. P. Stanforth, Catalytic Cross-Coupling Reactions in Biary Synthesis, Tetrahedron, 54, 1998, 263-303; J. K. Stille, Angew Chem, Int, Ed, Eng., 1986, 25, 509-524; N. Miyaura and A Suzuki, Chem. Rev., 1995, 95, 2457-2483; D. Baranano, G, Mann, and J. F. Hartwing, Current Org. Chem., 1997, 1, 287-305.

More preferably, $Z^1$ is halogen and $Z^2$ is boronic acid residue, but they are interchangeable.

Generally, the reaction may be conducted at a temperature from room temperature to 100° C., preferably 20° C. to 80° C.

In the reaction, solvents such as water, organic solvents (e.g., dioxane, dimethylformamide, 1,2-dimethoxyethane) or mixed solvent thereof may be used.

Bases such as $Na_2CO_3$, $NaHCO_3$, $Ba(OH)_2$, $K_3PO_4$, $Cs_2CO_3$, $K_2CO_3$, NaOH, etc., can be used. Silver oxide may be used in stead of such base.

For palladium catalyst, palladium[0]catalysts, such as for example, palladium acetate, $Pd(PPh_3)_4$, $Pd(dba)_2$, $PdCl_2(PPh_3)_2$, $PdCl_2(MeCN)_2$, $PPdCl(Bn)(PPh_3)_2$, etc., may be used (Ph: phenyl, Me: methyl, Bn: benzyl, dba: PhCH=CHC(O)CH=CHPh).

The reaction may be conducted for from several minutes to tens of hours, preferably about 1 hour to about 10 hours.

When $Z^1$ or $Z^2$ is a group such as trimethylstannyl, a metal catalyst, such as manganese, nickel, copper, stannum or the like, can be used in stead of Pd catalysts.

(Method 3)

[Chemical Formula 73]

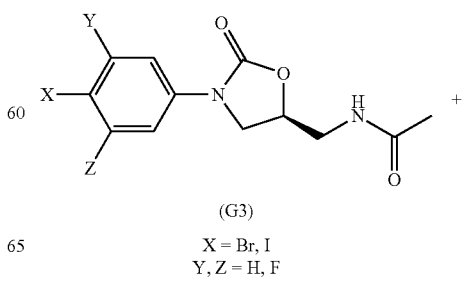

X = Br, I
Y, Z = H, F

-continued

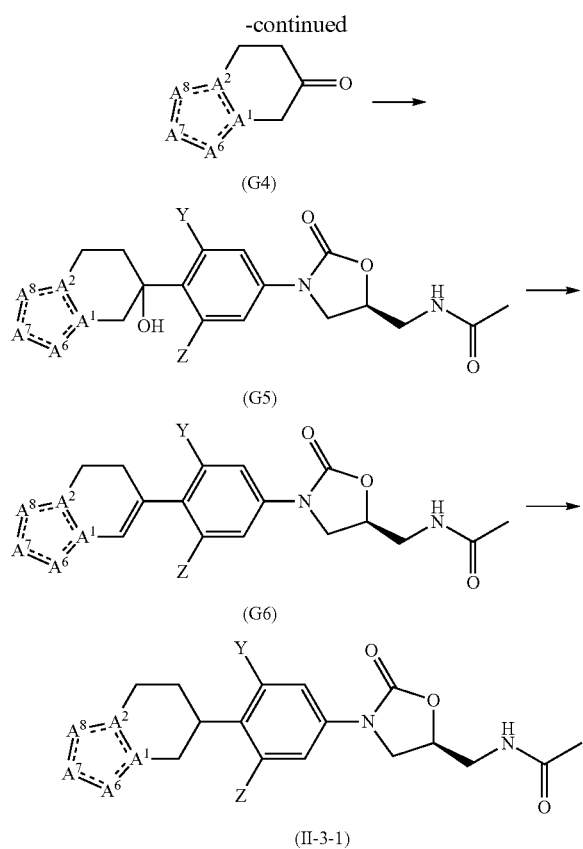

wherein each variable is as defined above.

Compound (G5) can be prepared by metal-halogen exchange of compound (G3) using an alkyl metal, such as n-BuLi, in an aprotic solvent, such as THF, at low temperature (e.g., −30° C.) to form the lithium salt, and followed by addition of compound (G4) to react at this temperature.

Compound (G6) can be prepared by heating compound (G5) in a solvent (e.g., toluene) in the presence of an acid, such as p-toluene sulfonic acid, and followed by azeotropic dehydration.

Also, compound (G6) may be prepared by heating compound (G5) in alcohol (R—OH) in the presence of an acid, such as p-toluene sulfonic acid.

[Chemical Formula 74]

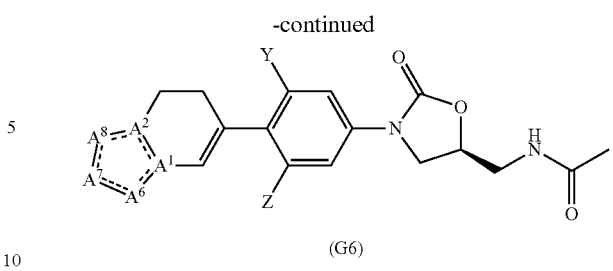

wherein each variable is as defined above.

Alternatively, compound (G6) may be prepared according to the following procedure. compound (G3) is subjected to metal-halogen exchange using an alkyl metal, such as n-BuLi, in an aprotic solvent, such as THF, at low temperature (e.g., −78° C.) to form the lithium salt, and followed by reaction with trialkoxy borane, such as tri(isopropoxy)borane, to afford boronic acid (G8). Separately, compound (G4) is treated with trifluoromethanesulfonic anhydride and diisopropylethyl amine in dichloromethane to afford triflate (G9). The boronic acid (G8) and the triflate (G9) are heated with stirring in an aprotic solvent, such as dimethoxyethane, in the presence of palladium catalyst, such as tetrakis(triphenylphosphine)palladium, and a base, such as sodium carbonate, to afford compound (G6).

[Chemical Formula 75]

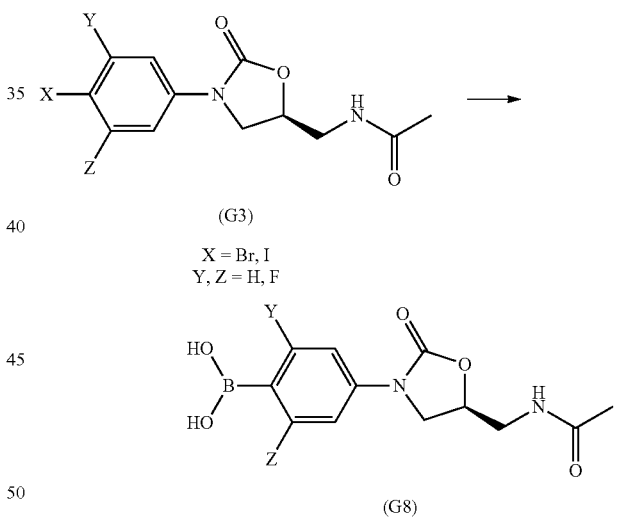

X = Br, I
Y, Z = H, F

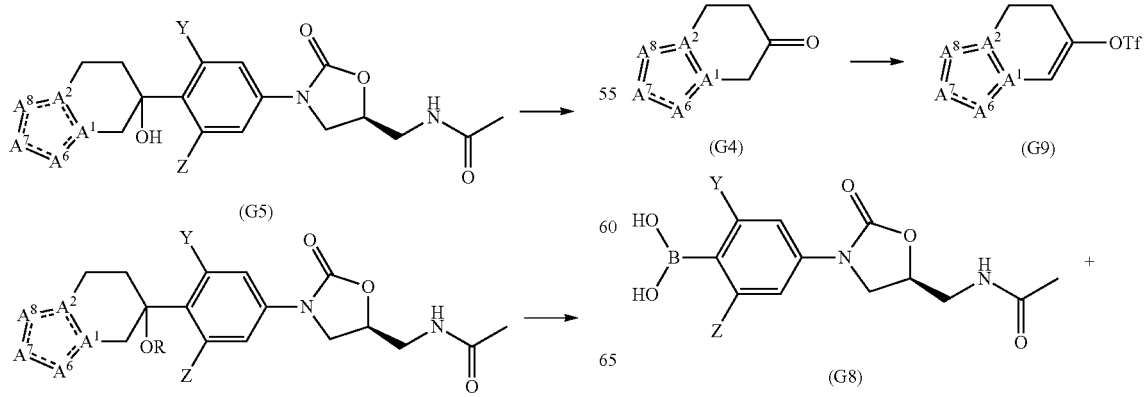

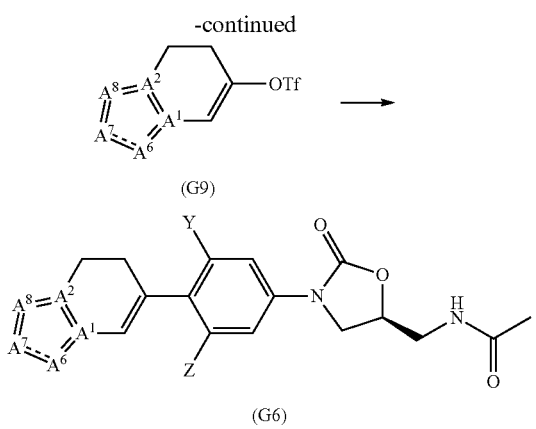

(G9)

(G6)

wherein each variable is as defined above.

Compound (II-3-1) can be prepared by hydrogenation of compound (G6) at room temperature in the presence of palladium on carbon under hydrogen atmosphere.

(Method 4)

[Chemical Formula 76]

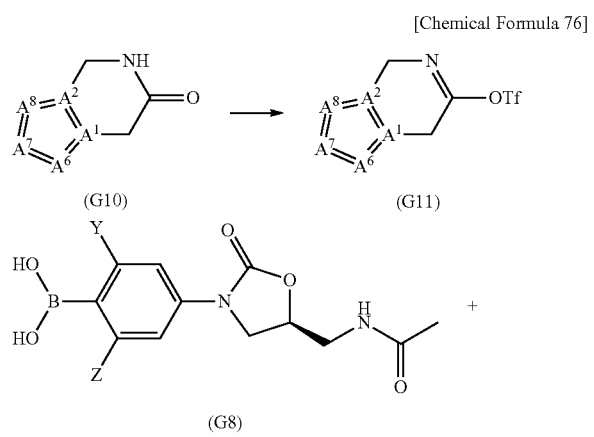

(G10)        (G11)

(G8)

Y, Z = H, F (G11)

(II-3-2)

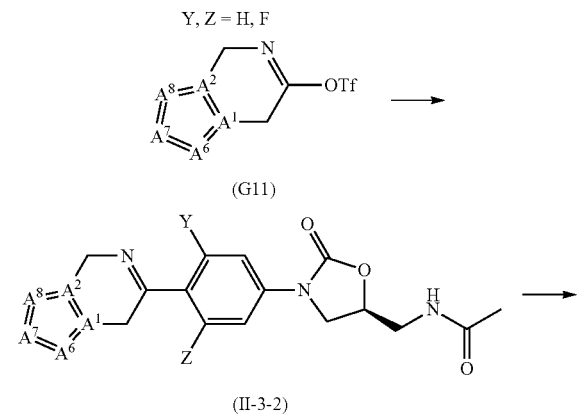

(II-3-3)

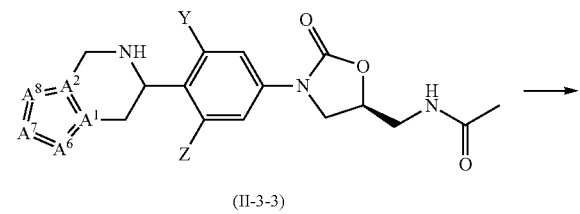

(II-3-4)

wherein each variable is as defined above.

Compound (G10) may be treated with trifluoromethanesulfonic anhydride in a solvent (e.g., pyridine) in the presence of a base (e.g., dimethylaminopyridine) to afford iminotriflate (G11). Then, a mixture of boronic acid (G8) and the iminotriflate (G11) in an aprotic solvent, such as dimethoxyethane, may be stirred under heating in the presence of a palladium catalyst, such as tetrakis(triphenylphosphine)palladium, and a base, such as sodium carbonate, to afford compound (II-3-2).

Compound (II-3-3) can be prepared by hydrogenation of compound (II-3-2) at room temperature in the presence of palladium on carbon under hydrogen atmosphere or by reduction with a reductant such as sodium borohydride.

Compound (II-3-4) can be prepared by the reaction of compound (II-3-3) with an aldehyde (e.g., formaldehyde when R is methyl) to form an imine and followed by reduction in the presence of a palladium on carbon under hydrogen atmosphere or by reduction with a reductant such as sodium cyanoborohydride or sodium triacetoxyborohydride. Alternatively, when R is methyl, compound (II-3-4) may be prepared by heating compound (II-3-3) with stirring in the presence of formic acid and formaldehyde.

(Method 5)

[Chemical Formula 77]

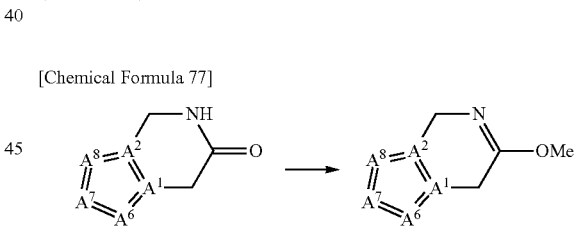

(G10)        (G12)

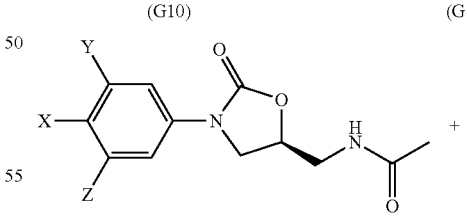

(G3)

X = Br, I
Y, Z = H, F

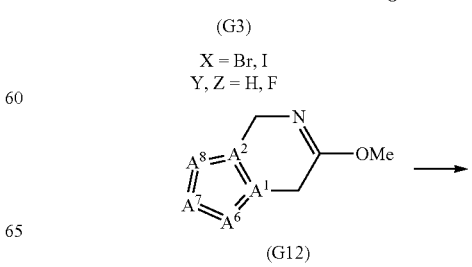

(G12)

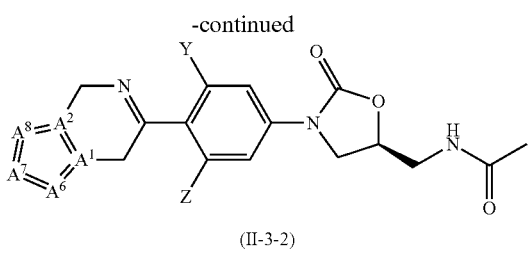

(II-3-2)

wherein each variable is as defined above.

Alternatively, compound (II-3-2) can be prepared by metal-halogen exchange of compound (G3) using an alkyl metal, such as n-BuLi, in an aprotic solvent, such as THF, at low temperature (e.g., −78° C.) to form salt, such as lithium salt, and followed by the reaction with cyclic imidate (G12) at room temperature.

The cyclic imidate (G12) can be prepared by the reaction under heating of compound (G10) with dimethyl sulfate in a solvent (e.g., toluene).

The 5-position of the oxazolidinone ring of the compounds as obtained above can be modified further with a substituent to afford various oxazolidinone derivatives. Also, ring B, ring C and ring D may be further modified. Such modification is within level of ordinary skill in the art and can be readily practiced by a skilled person in the art.

Any functional group (e.g., —OH, —NH$_2$, —COON) in an intermediate may be preliminarily protected during the synthesis. For example, it may be protected with an appropriate protecting group, such as t-butoxycarbonyl group, benzyloxycarbonyl group, etc., and readily removed at an appropriate time during the synthesis, as described in Greene, T. W.; Wuts, P. G. M., "Protective Groups in Organic Synthesis", 2nd ed; John Wiley & Sons: New York (1991).

Typically, the starting compound (G4) includes the following compounds.

[Chemical Formula 78]

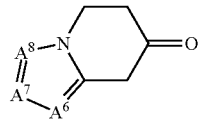

(G4-a)

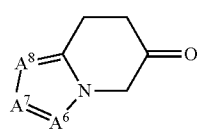

(G4-b)

wherein each variable is as defined above.

Typically, the starting compound (G10) includes the following compounds.

[Chemical Formula 79]

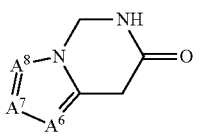

(G10-a)

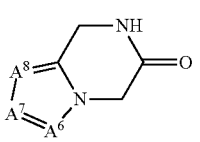

(G10-b)

wherein each variable is as defined above.

The preparation procedures of these starting compounds are described below.

(Method 6)

[Chemical Formula 80]

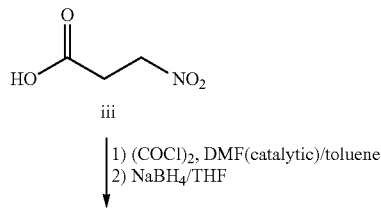

iii 1) (COCl)$_2$, DMF(catalytic)/toluene
2) NaBH$_4$/THF

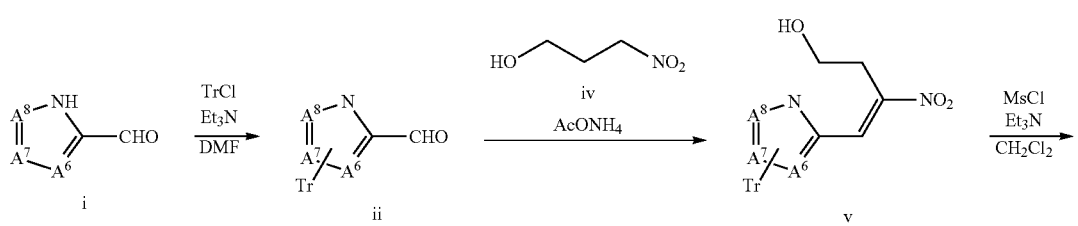

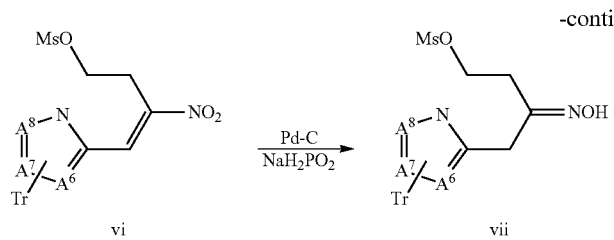 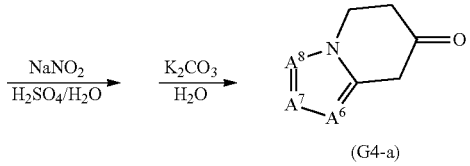

wherein each variable is as defined above.

(1) Compound (i) is dissolved in DMF, triethylamine and then trityl chloride are added. After stirring at room temperature to confirm disappearance of compound (i), the reaction mixture is poured into ice water and filtered to afford a solid precipitated, which is then washed with water and dissolved in ethyl acetate. The solution is washed with brine, dried over anhydrous sodium sulfate, filtered and concentrated. The solid residue is slurried in an organic solvent (e.g., mixture of n-hexanes/ethyl acetate) and filtered, and dried under reduced pressure to afford compound (ii).

(2) To a mixture of compound (iii), oxalyl chloride and toluene, catalytic amount of DMF is added, and the reaction is stirred at room temperature. The reaction mixture is then concentrated to dryness, and the residue is dissolved in THF. Sodium borohydride is added under ice-cooling, and the solution is stirred at room temperature. The reaction is quenched with diluted hydrochloric acid, and it is diluted with ethyl acetate. The solution is washed with minimum quantity of brine, dried over anhydrous sodium sulfate, filtered and concentrated to afford compound (iv).

(3) A mixture of compound (ii), compound (iv), ammonium acetate and toluene is heated with stirring under azeotropic dehydration condition. The reaction mixture is then cooled to room temperature, diluted with ethyl acetate, and washed with brine. After dryness over anhydrous sodium sulfate, filtration and concentration, the residue is purified by column chromatography to afford compound (v).

(4) Compound (v) is dissolved in dichloromethane, and triethylamine and methanesulfonyl chloride are added under ice-cooling and the solution is stirred. The reaction mixture is then diluted with ethyl acetate and washed sequentially with diluted hydrochloric acid, aqueous 5% sodium bicarbonate and brine, and dried over anhydrous sodium sulfate, filtered and concentrated. The residue is purified by column chromatography to afford compound (vi).

(5) To a mixture of compound (vi) and palladium on carbon in THF, aqueous sodium phosphinate is added dropwise under nitrogen stream. Then, palladium on carbon is filtered off, and the solution is diluted with ethyl acetate. The organic layer is separated and washed sequentially with saturated aqueous potassium carbonate and brine, and dried over anhydrous sodium sulfate, filtered and concentrated. The residue is purified by column chromatography to afford compound (vii).

(6) Compound (vii) is dissolved in 20% sulfuric acid, and sodium nitrite is added under ice-cooling and the solution is stirred. Aqueous 20% potassium carbonate is added to adjust to basic pH, and the solution is stirred at room temperature. The solution is extracted with ethyl acetate, dried over anhydrous sodium sulfate, filtered, and concentrated. The residue is purified by column chromatography to afford compound (G4-a).

(Method 7)

[Chemical Formula 81]

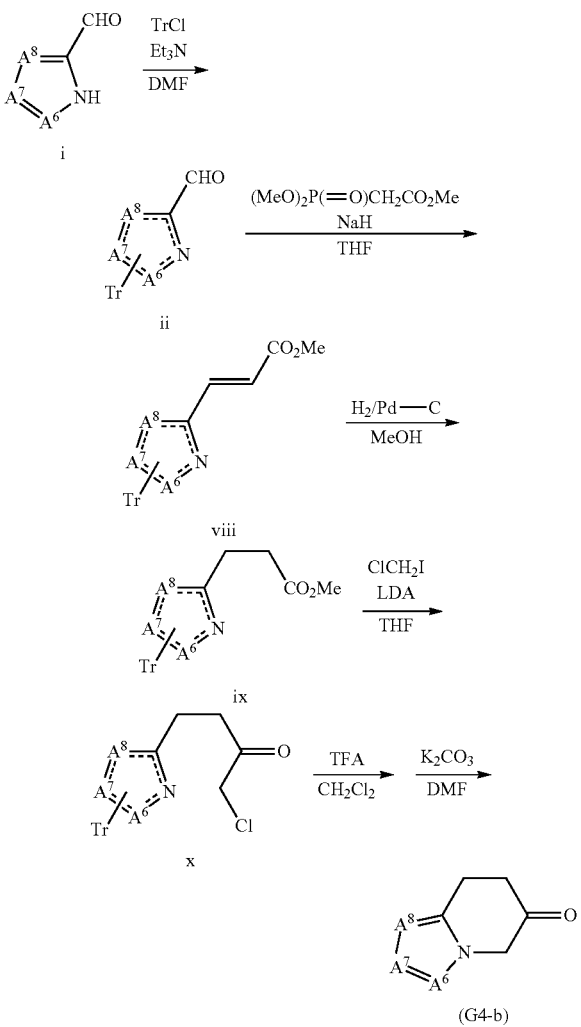

wherein each variable is as defined above.

(1) To a suspension of sodium hydride in THF, methyl (dimethoxyphosphoryl)acetate is added under ice-cooling, and the suspension is stirred. To the resulting slurry, compound (ii) is added and stirred at room temperature. Acetic acid is then added to neutralize, and the reaction mixture is diluted with ethyl acetate. The organic layer is washed sequentially with saturated aqueous sodium bicarbonate and brine, dried over anhydrous sodium sulfate, filtered, and concentrated. The solid residue is slurried in an organic solvent (e.g., n-hexanes/ethyl acetate (9:1)), and the slurry is filtered and dried under reduced pressure to afford compound (viii).

(2) Compound (viii) is dissolved in methanol, palladium on carbon is added and the solution is stirred under hydrogen atmosphere at room temperature. Then, palladium on carbon is filtered off, and the solution is concentrated to dryness. The residue is purified by column chromatography to afford compound (ix).

(3) Compound (ix) and chloroiodomethane are dissolved in THF and cooled to −78° C., and Lithium bis(trimethylsilyl) amide in THF is added and the solution is stirred at this temperature. After 30 minutes to 1 hour, acetic acid in THF is added, and stirring is continued. After 15 to 30 minutes, brine is added and the mixture is extracted with ethyl acetate. The organic layer is washed sequentially with saturated aqueous sodium bicarbonate, aqueous 5% sodium hydrogen sulfite and brine, dried over anhydrous sodium sulfate, filtered and concentrated. The residue is purified by column chromatography to afford compound (x).

(4) Compound (x) is dissolved in dichloromethane, and trifluoroacetic acid is added and the solution is stirred at room temperature. The reaction mixture is then concentrated to dryness, and the residue is dissolved in DMF. Potassium carbonate is added, and the solution is stirred at room temperature. Then, the reaction mixture is diluted with ethyl acetate, and washed several times with brine. The resulting aqueous layers are re-extracted with ethyl acetate, and respective organic layers are combined and dried over anhydrous sodium sulfate, filtered and concentrated. The residue is purified by column chromatography to afford compound (G4-b).

(Method 8)

[Chemical Formula 82]

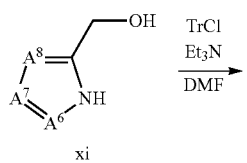

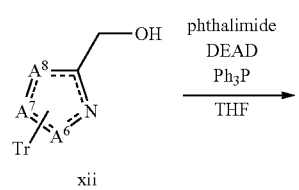

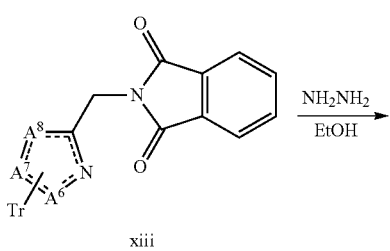

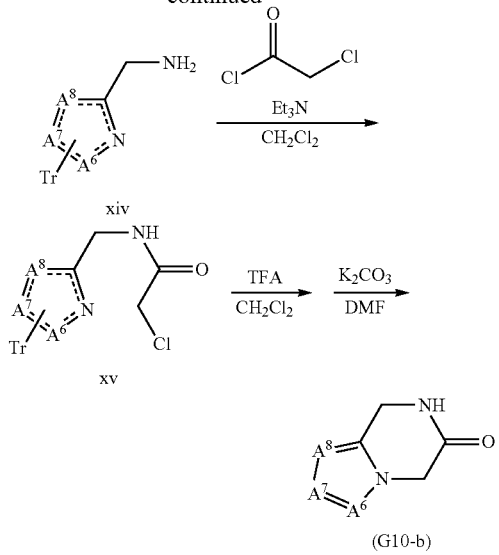

wherein each variable is as defined above.

(1) Compound (xi) is dissolved in DMF, and triethylamine and then trityl chloride are added. After stirring at room temperature to confirm disappearance of compound (xi), the reaction mixture is poured into ice water, and stirring is continued. The resulting solid precipitate is filtered and washed with ice water. The filtered solid is stirred in cold dioxane, stirred, filtered and dried under reduced pressure to afford compound (xii).

(2) To a mixture of compound (xii), phthalimido and triphenylphosphine in THF, DEAD in toluene is added under ice-cooling. After stirring overnight at room temperature, the reaction mixture is concentrated. The residue is purified by column chromatography to afford compound (xiii).

(3) Compound (xiii) is suspended in ethanol, and hydrazine hydrate is added and the suspension is heated at reflux for 3 hours. After cooling to 40° C., hydrochloric acid is added, and stirring is continued for additional 1 hour. The reaction mixture is concentrated to dryness, and the residue is added with water and filtered. The filtrate is added with aqueous 10% sodium hydroxide to become alkaline, and extracted with diethyl ether. The extract is dried over anhydrous sodium sulfate, filtered, and concentrated to afford compound (xiv).

(4) Compound (xiv) is dissolved in dichloromethane, and triethylamine is added. Under ice-cooling, chloroacetyl chloride is added and the solution is stirred at room temperature. The reaction mixture is then diluted with ethyl acetate, and washed sequentially with diluted hydrochloric acid, aqueous 5% sodium bicarbonate and brine. After dryness over anhydrous sodium sulfate, filtration, and concentration, the residue is purified by column chromatography to afford compound (xv).

(5) Compound (xv) is dissolved in dichloromethane, and trifluoroacetic acid is added and the solution is stirred at room temperature. Then, the reaction mixture is concentrated to dryness, and the residue is dissolved in DMF. Potassium carbonate is added, and the solution is stirred at room temperature. The reaction mixture is then diluted with ethyl acetate and washed several times with brine. The resulting aqueous layers are re-extracted with ethyl acetate, and respective organic layers are combined and dried over anhydrous sodium sulfate, filtered and concentrated. The residue is purified by column chromatography to afford compound (G10-b).

According to the synthesis of compound (G10-b), compound (G10-a) can be synthesized using a compound of the formula Xi':

[Chemical Formula 83]

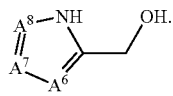

Xi'

(Method 9)
Formation of triazolopyridine ring

[Chemical Formula 84]

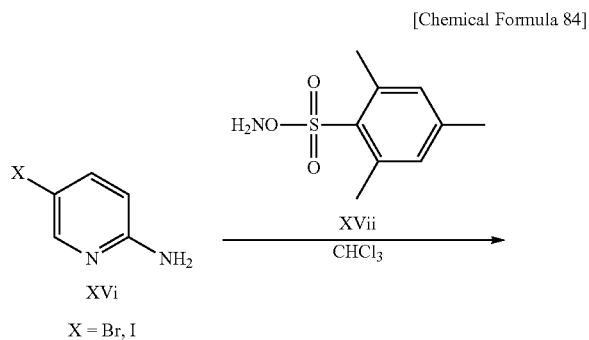

(1) Compound (xvi) is dissolved in chloroform, and compound (xvii) is added and the solution is stirred at room temperature. The resulting precipitate is filtered to afford N-amino compound (xviii).

(2) The resulting compound (xviii) is dissolved in acetic anhydride, and concentrated hydrochloric acid is added, and the solution is heated at reflux. Then the reaction mixture is neutralized and extracted with methanol-chloroform. After washing with water and drying, the solvent is evaporated to afford compound (G13).

(Method 10)
Formation of boronic acid ester

[Chemical Formula 85]

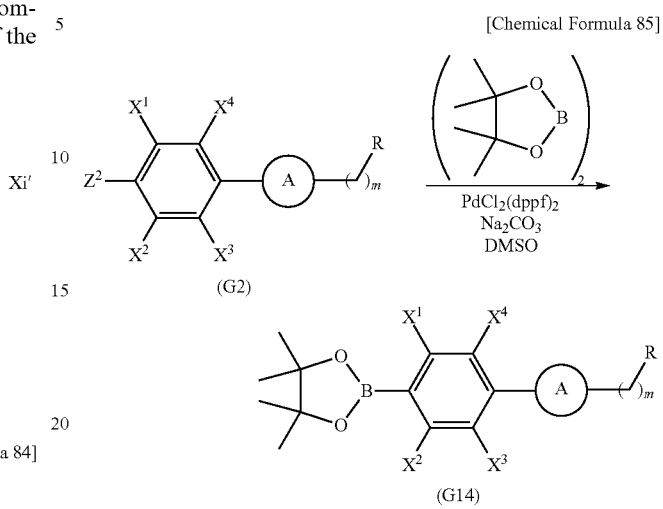

wherein each variable is as defined above.

Compound (G2) is reacted with bis(pinacolato)diborane in a solvent such as DMSO in the presence of palladium catalyst to afford boronic acid ester compound (G14).

(Method 11)
Formation of triazole side chain

[Chemical Formula 86]

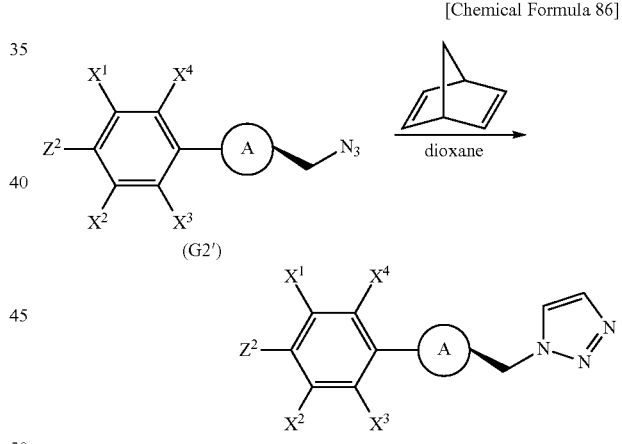

wherein each variable is as defined above.

Azido compound (G2') is dissolved in dioxane, bicyclo[2,2,1]hepta-2,5-diene is added to react to afford a triazole side chain derivative (G15).

The present invention also provides a pharmaceutical composition comprising the compound of the invention, a pharmaceutically acceptable salt or hydrate thereof as an active ingredient. Based on the antimicrobial activity of the compound, one example of such pharmaceutical composition is an antimicrobial drug. When the compound of the invention is used in a treatment, a therapeutically effective amount of the compound, a salt or solvate thereof is administered to an animal, including human, which is affected with infection. The route of administration may be oral or parenteral. For this purpose, the compound of the invention or a salt thereof is combined with a pharmaceutically acceptable carrier, diluent or excipient, and it is incorporated into a capsule or compressed into a tablet. Alternatively, the composition may be in a dosage form such as powder or granule. For parenteral administration, it is formulated into an aqueous solution or suspension suitable for subcutaneous injection, intravenous injection, intraperitoneal injection, intramuscular injection, etc. Also, the composition can be provided as suppositories, topical formulations, eye-drops and the like.

The pharmaceutically acceptable salt of the compound of the invention include salts with an inorganic base, ammonia, organic base, inorganic acid, organic acid, basic amino acid, halogen ion, etc., or intramolecular salts. Examples of the inorganic base include alkali metals (Na, K, etc.), alkaline earth metals (Ca, Mg, etc.). Examples of the organic base include trimethylamine, triethylamine, choline, procaine, ethanolamine, etc. Examples of the inorganic acid include hydrochloric acid, hydrobromic acid, sulphuric acid, nitric acid, phosphoric acid and the like. Examples of organic acid include p-toluenesulphonic acid, methanesulphonic acid, formic acid, trifluoro acetate, maleic acid and the like. Examples of basic amino acid include lysine, arginine, ornithine, histidine and the like. Also, such salt may be a solvate.

Oral administration can be practiced in a solid or liquid dosage form prepared according to a conventional method, such as tablet, powder, capsule, granule, suspension, liquid, syrup, lozenge, sublingual tablet and other dosage forms. If necessary, unit dosage form for oral administration can be microcapsulated. Also, such formulation may be coated or embedded into polymer or wax, in order to prolong the duration of activity or provide sustained release.

Parenteral administration can be practiced in a liquid dosage form prepared according to a conventional method, such as injectable formulation in the form of solution or suspension.

Among the above routes of administration, oral administration and intravenous administration by injection are preferred. Of course, administration should be practiced in a dosage form suitable for the route of administration.

For oral administration, in general, the daily dose may be about 10 mg to 4000 mg, preferably 100 mg to 2000 mg per day. For parenteral administration, the daily dose may be about 10 mg to 4000 mg, preferably 50 mg to 2000 mg per day.

EXAMPLES

The present invention is described further by way of the following Examples and Test Examples.
(Abbreviation)
AC=Acetyl
dppf=1,1'-bis(diphenylphosphino)ferrocene Reference Example 1

[Chemical Formula 87]

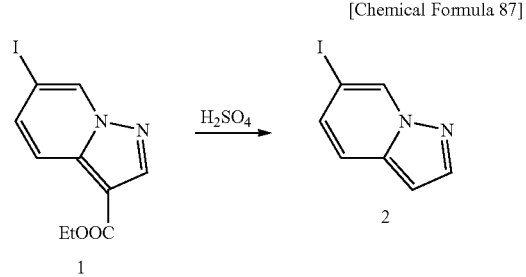 [SMILES: CCOC(=O)c1cnn2cc(I)ccc12 ; "H2SO4" ; Ic1ccc2ccnn2c1]

Compound 1 (96 mg) was suspended in 1 mL of sulfuric acid (40 wt %) and heated at reflux. Then, to this was added 2N sodium hydroxide to become basic and extracted with dichloromethane. The organic layer is washed with purified water and brine and dried over magnesium sulfate. After filtration, the solution is concentrated to afford 85 mg of compound 2 as brown oil.

Example 1

(1) Preparation of 6-bromoimidazo[1,2-a]pyridine (4)

[Chemical Formula 88]

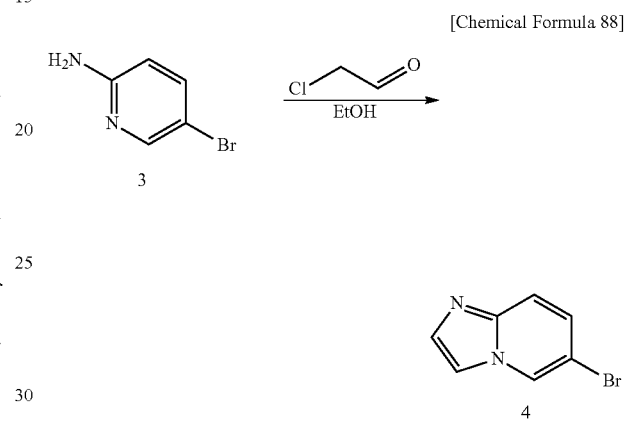

2.00 g of 2-amino-5-bromopyridine (3) is dissolved in ethanol (35 mL), and chloroacetaldehyde in water (2.52 mL, 6.1 mol/L) was added and the reaction mixture was heated at reflux for 3 hours. The reaction mixture was concentrated, and saturated aqueous $NaHCO_3$ was added to the residue, and it is extracted with ethyl acetate. After conventional workup afford 2.30 g of the titled compound as a brown powder (yield: 100%).

LCMS (ESI) m/z (M+H)+: 368.93

(2) Preparation of (S)-n-((3-(3-fluoro-4-(imidazo[1,2-a]pyridine-6-yl)phenyl)-2-oxooxazolidine-5-yl)methyl)acetamide

[Chemical Formula 89]

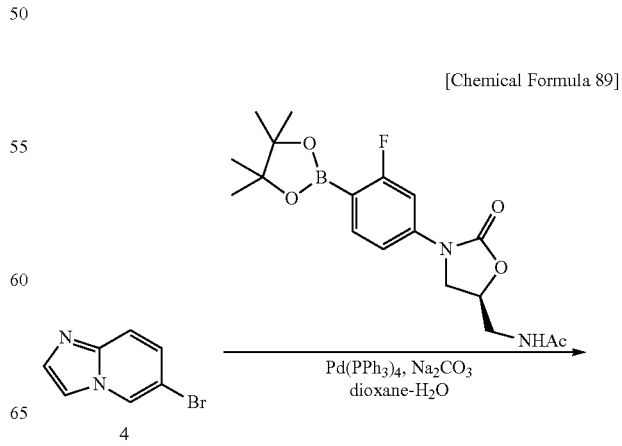

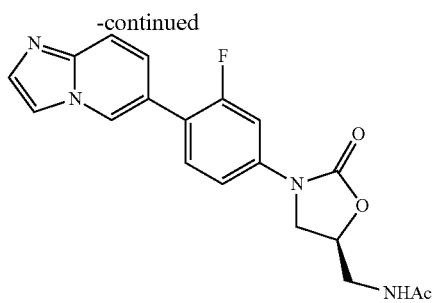

172 mg of 6-bromoimidazo[1,2-a]pyridine (4), 300 mg of (S)-n-((3-(3-fluoro-4-(4,4,5,5-tetramethyl-1,3,2-dioxaborane-2-yl)phenyl)-2-oxooxazolidine-5-yl)methyl)acetamide, 92 mg of tetrakis (triphenylphosphine)palladium (0) and 420 mg of sodium carbonate were suspended in 1,4-dioxane (3 mL) and water (0.3 mL), and the suspension was heated at reflux for 6 hours. The reaction mixture was poured into saturated aqueous $NaHCO_3$, and extracted with ethyl acetate. After conventional workup, the resulting residue was washed with ethyl acetate to afford 85 mg of the titled compound as a brown powder (yield: 29%).

LCMS (ESI) m/z (M+H)+: 368.93

$^1$H-NMR (DMSO-$d_6$) δ: 1.83 (3H, s), 3.41 (2H, t, J=5.7 Hz), 3.78 (1H, dd, J=8.7, 6.3 Hz), 4.17 (1H, t, J=8.7 Hz), 4.73-4.78 (1H, m), 7.39-7.45 (2H, m), 7.60-7.68 (3H, m), 7.99 (1H, s), 8.26 (1H, t, J=5.4 Hz), 8.79 (1H, s).

Example 2

(1) Preparation of ethyl 6-bromoimidazo[1,2-a]pyridine-2-carboxylate (5)

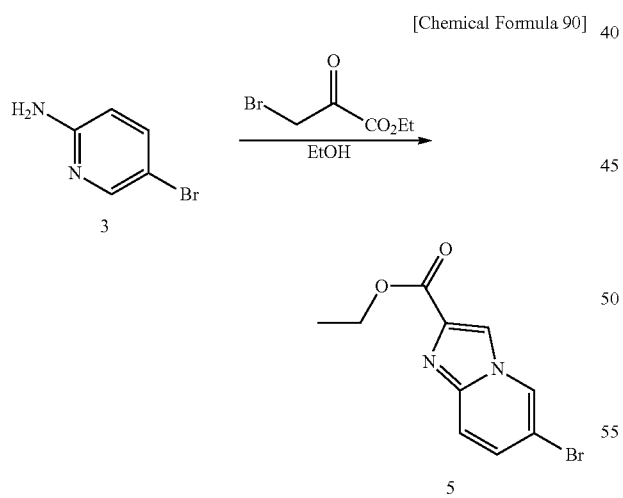

15.00 g of 2-amino-5-bromopyridine (3), 16.99 g of ethyl 3-bromo-2-oxopropanoate were dissolved in ethanol (100 mL), and the solution is heated at reflux for 8 hours. The reaction mixture was concentrated, and saturated aqueous $NaHCO_3$ was added to the residue. The resulting precipitate was isolated by filtration, and washed with water to afford 17.01 g of the titled compound as colorless powder (yield: 73%).

(2) Preparation of (S)-ethyl 6-(4-(5-(acetamidomethyl)-2-oxooxazolidine-3-yl)-2-fluorophenyl)imidazo[1,2-a]pyridine-2-carboxylate

[Chemical Formula 91]

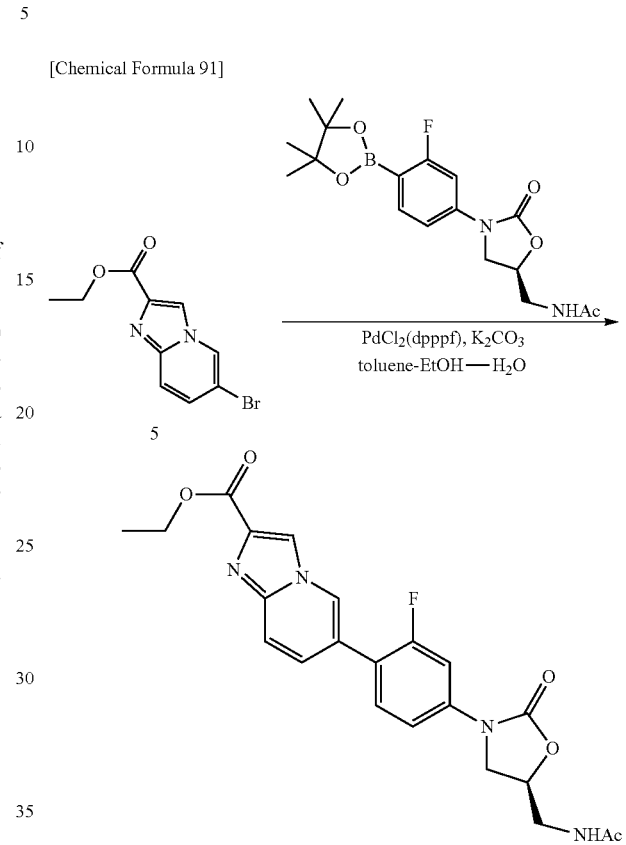

4.00 g of ethyl 6-bromoimidazo[1,2-a]pyridine-2-carboxylate (5), 2.85 g of (S)-n-((3-(3-fluoro-4-(4,4,5,5-tetramethyl-1,3,2-dioxaborane-2-yl)phenyl)-2-oxooxazolidine-5-yl)methyl)acetamide, 0.542 g of $PdCl_2$ (dppf) and 4.39 g of potassium carbonate were suspended in toluene (15 mL)-ethanol (15 mL)-water (5 mL), and the suspension was heated at reflux for 4 hours. The resulting precipitate was isolated and washed with water and ethyl acetate to afford 3.46 g of the titled compound as colorless powder (yield: 74%).

LCMS (ESI) m/z (M+H)+: 441.10

Example 3

[Chemical Formula 92]

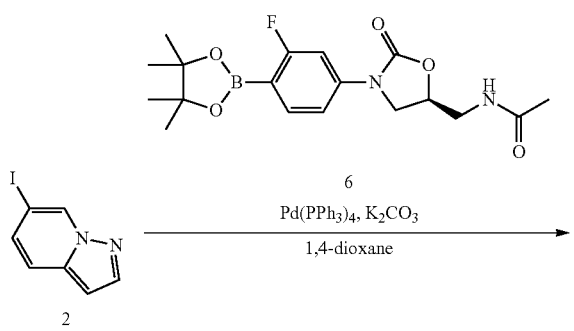

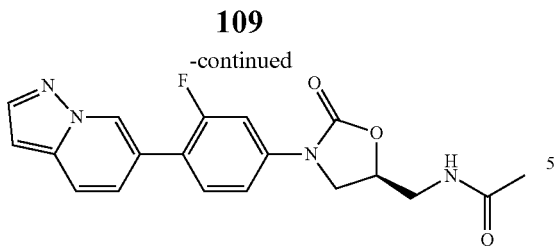

Compound 6 (158 mg) was dissolved in 1,4-dioxane (2 mL), and compound 2 (85 mg) as obtained in Reference Example 1, potassium carbonate (1443 mg), and tetrakis(triphenylphosphine)palladium (20 mg) were added, and the solution was heated at reflux to complete the reaction. After cooling, purified water was added and filtered, and the resulting residue was washed with ethyl acetate and purified water to afford the desired compound (11 mg).

LCMS (ESI) m/z (M+H)+: 368.93

$^1$H-NMR (DMSO-d$_6$) δ: 1.84 (3H, s), 3.44 (2H, t, J=5.5 Hz), 3.80 (1H, dd, J=9.1, 6.5 Hz), 4.18 (1H, t, J=9.1 Hz), 4.72-4.82 (1H, m), 6.67 (1H, d, J=2.1 Hz), 7.38-7.47 (2H, m), 7.82-7.60 (3H, m), 8.05 (1H, d, J=2.1 Hz), 8.26 (1H, t, J=5.7 Hz), 8.87 (1H, s).

Example 4

(1) Preparation of 6-bromo-2-methyl[1,2,4]triazolo[1,5-a]pyridine (14)

[Chemical Formula 93]

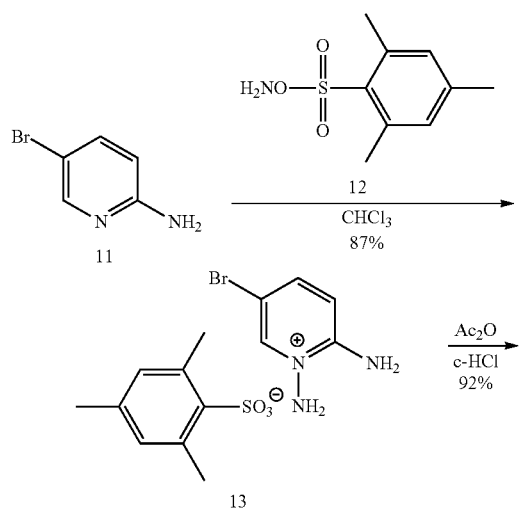

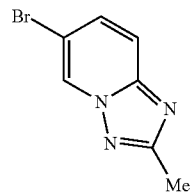

Compound 13

To 2-amino-5-bromopyridine (11, 3.05 g) in chloroform (100 mL), O-mesitylenesulfonylhydroxylamine (12, 12.91 g) was added, and the solution is heated at room temperature for 3 hours. The resulting precipitate was then filtered to afford 6.21 g of N-amino compound (13) as powder (87%). Compound 13: as colorless powder; 1H-NMR (300 MHz, CDCl$_3$-CD$_3$OD (5:1)) δ 2.23 (s, 3H), 2.61 (s, 6H), 6.83 (s, 2H), 7.05 (d, 9.5), 7.61 (dd, 9.5, 2, 1H), 8.13 (d, 2, 1H); IR (KBr) ν$_{max}$ 1666 cm$^{-1}$;

LRMS m/z 200 (45), 187, 189 (38, 37), 134 (29), 118 (100), 103 (43), 91 (56), 81 (34), 64 (50), 51 (70).

Compound 14

To compound 13 (7.01 g) in acetic anhydride (9 mL), concentrated hydrochloric acid (1 mL) was added and heated at reflux for 14 hours. The reaction mixture was neutralized with aqueous NaHCO$_3$, and extracted with methanol-chloroform (1:9). After washing with water and dryness, solvent was removed. The residue was recrystallized from ethanol to afford 2.985 g of compound 14 as colorless needle-like crystal. The mother liquid from the recrystallization was purified by column chromatography (hexane-ethyl acetate (1:1)) to afford 401 mg of compound 14. Total: 3.385 g (92%).

Compound 14: as colorless needle-like crystal mp: 154.5-155° C. (Hexane-CHCl$_3$);

1H-NMR (300 MHz, CDCl$_3$) 2.60 (s, 3H), 7.54 (d, 1, 2H), 8.64 (dd, 1, 1, 1H);

LRMS m/z 211, 213 (M$^+$, 96, 100), 170, 172 (13, 12), 156, 158 (10, 7), 143, 145 (10, 6), 64 (58), 42 (18).

(2) Preparation of Compound 16

[Chemical Formula 94]

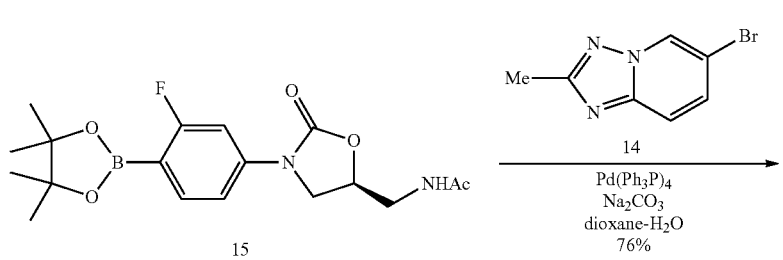

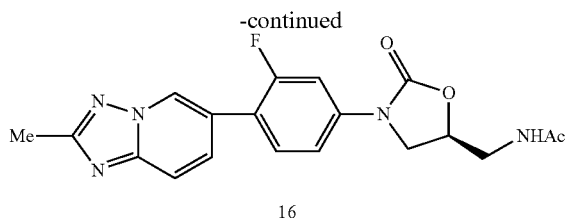

16

To boronic acid ester compound having acetamide side chain (15, 1.902 g), and 6-bromo-2-methyltriazolopyridine compound (14, 1.162 g) in dioxane (40 mL) and water (10 mL), $Na_2CO_3$ (1.85 g) and $Pd(Ph_3P)_4$ (588 mg) were added and the solution was stirred at 90 to 100° C. for 1 hour. Then, the solvent was removed under reduced pressure. The residue was dissolved in ethanol, and 1.246 g of colorless compound 16 precipitated. The mother liquid was purified by column chromatography (chloroform-methanol (9:1)). 223 mg of colorless compound 16 was precipitated from ethanol. Total: 1.469 g (76%).

Compound 16: 1H-NMR (300 MHz, $CDCl_3$-$CD_3OD$ (9:1)) 2.04 (s, 3H), 2.62 (s, 3H), 3.60-3.72 (m, 2H), 3.87 (dd, 9, 7, 1H), 4.14 (dd, 9, 9, 1H), 4.81-4.90 (m, 1H), 7.34 (dd, 8.5, 2, 1H), 7.49 (dd, 8.5, 8.5, 1H), 7.62 (dd, 13, 2, 1H), 7.66-7.75 (m, 2H), 8.69 (d, 1, 1H);

LRMS m/z 383 ($M^+$, 44), 339 (18), 311 (7), 280 (19), 255 (56), 242 (27), 158 (26), 85 (26), 73 (20), 56 (52), 43 (100).

Example 5

(1) Preparation of 7-bromo-2-methyl[1,2,4]triazolo[1,5-a]pyridine (19)

[Chemical Formula 95]

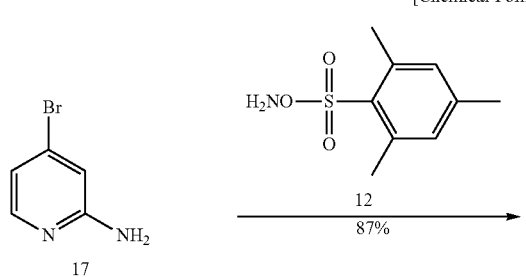

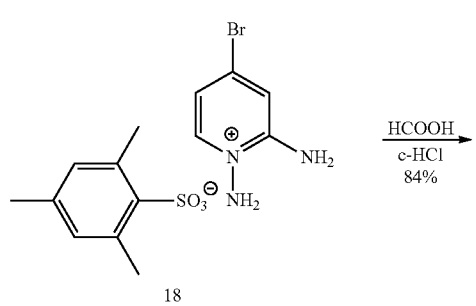

18

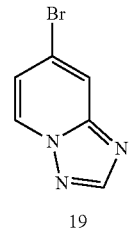

19

Compound 18

To 2-amino-4-bromopyridine (17, 5.00 g) in chloroform (150 mL), O-mesitylenesulfonyl hydroxylamine (12, 28.0 g) was added and the solution was stirred at room temperature for 2 hours. The resulting precipitate was then filtered to afford 9.80 g of compound 18 as powder (87%).

Compound 18: as colorless powder; 1H-NMR (300 MHz, $CD_3OD$) δ 2.24 (s, 3H), 2.63 (s, 6H), 6.85 (s, 2H), 6.91 (dd, 7, 2, 1H), 7.28 (d, 2), 7.85 (d, 7, 1H);

LRMS m/z 200(45), 187, 189 (29, 28), 134(27), 118(100), 103(43), 91(57), 81(62), 65(34), 51 (49).

Compound 19

To compound 18 in 98% formic acid (12 mL) and water (3 mL), concentrated hydrochloric acid (3 mL) was added and the solution was heated at reflux for 15 hours. Then, the reaction mixture was concentrated under reduced pressure to reduce the volume by half, neutralized with aqueous $NaHCO_3$ and extracted with methanol-chloroform (1:9). After washing with water and drying, the solvent was evaporated. The residue was recrystallized from hexane-chloroform to afford 3.313 g of compound 19 as colorless needle-like crystal. The recrystallization mother liquid was purified by column chromatography (methanol-chloroform (1:19)). Recrystallization from hexane-chloroform afforded 977 mg of compound 19 as colorless needle-like crystal. Total: 4.290 g (84%).

Compound 19: as colorless needle-like crystal mp: 108-108.5° C. (Hexane-$CHCl_3$);

1H-NMR (300 MHz, $CDCl_3$) 7.15 (dd, 7, 2, 1H), 7.97 (d, 2, 1H), 8.34 (s, 1H), 8.48 (d, 7, 1H);

LRMS m/z 197, 199 ($M^+$, 100, 97), 156, 158 (10, 11), 91(42), 64 (74).

(2) Preparation of Compound 20

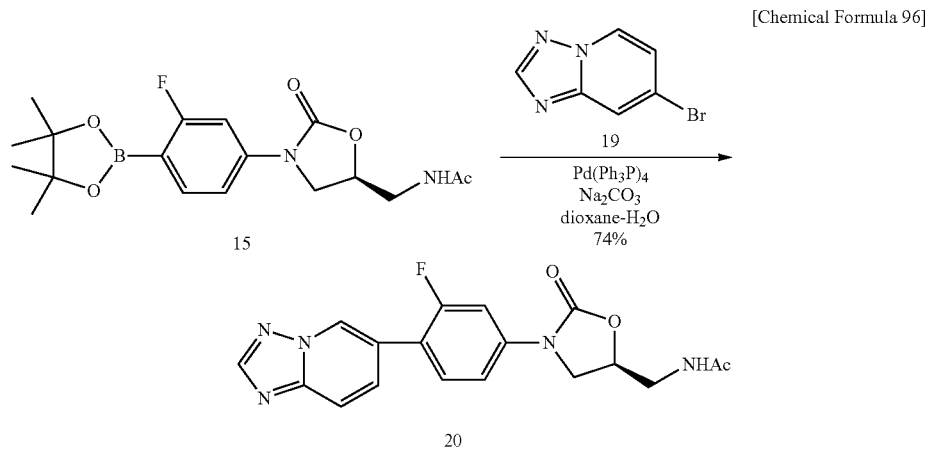

To boronic acid ester compound having acetamide side chain (15, 1.91 g) and 7-bromotriazolopyridine compound (19, 1.08 g) in dioxane (40 mL) and water (10 mL), $Na_2CO_3$ (1.89 g) and $Pd(Ph_3P)_4$ (591 mg) were added and the solution was heated at 90° C. to 100° C. for 1 hour. The solvent was then removed under reduced pressure. The residue was dissolved in ethanol-chloroform, and 1.250 g of colorless compound 20 was precipitated. The mother liquid was purified by column chromatography (chloroform-methanol (9:1)). 134 mg of colorless compound 20 was precipitated from ethanol. Total: 1.384 g (74%).

Compound 20: 1H-NMR (300 MHz, DMSO-d6) 1.83 (s, 3H), 3.80 (dd, 9, 6.5, 1H), 4.18 (dd, 9, 9, 1H), 4.72-4.82 (m, 1H), 7.40 (br d, 7.5, 1H), 7.47 (dd, 9, 2, 1H), 7.65 (dd, 14, 2, 1H), 7.78 (dd, 9, 9, 1H), 8.01 (br s, 1H), 8.26 (br t, 6, NH), 8.54 (s, 1H), 9.01 (d, 7.5, 1H);

LRMS m/z 369 (M+, 18), 325(39), 282(9), 265(13), 241 (100), 228(18), 158(24), 85(45), 73(18), 56(92), 44(36), 43 (99).

Example 6

(1) Preparation of Triazole Derivative (22)

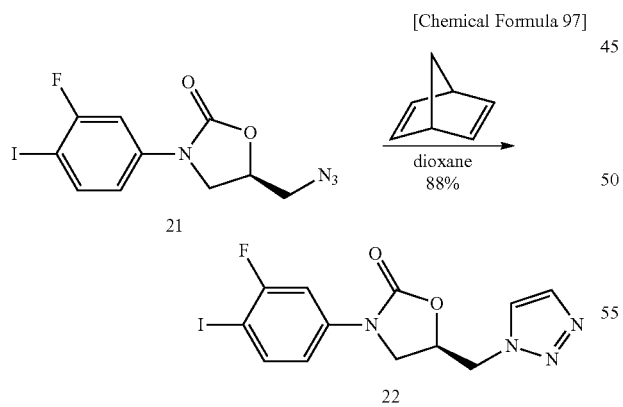

To azido compound (21, 2.11 g) in dioxane (10 mL), bicyclo[2,2,1]hepta-2,5-diene (2.0 mL) was added and the solution was heated at reflux for 15 hours. The solvent was then removed under reduced pressure, and the residue was washed with chloroform to afford 1.852 g of compound 22 as colorless powder (88%).

Compound 22: as colorless powder; 1H-NMR (300 MHz, $CDCl_3$-$CD_3OD$ (4:1)) 3.95 (dd, 9, 6, 1H), 4.21 (dd, 9, 9, 1H), 4.80 (dd, 14.5, 4.5, 1H), 4.86 (dd, 14.5, 4, 1H), 5.12 (dddd, 9, 6, 4.5, 4, 1H), 6.95 (dd, 8.5, 3, 1H), 7.38 (dd, 7, 3, 1H), 7.70 (dd, 8.5, 7, 1H), 7.74 (br s, 1H), 7.89 (d, 0.5, 1H);

LRMS m/z 388 (M+, 48), 275 (24), 263 (19), 248 (22), 221 (22), 148 (41), 135 (27), 108 (39), 96 (33), 94 (56), 83 (39), 80 (60), 55 (87), 54 (100), 41 (52).

(2) Preparation of Boronic Acid Ester Derivative (23)

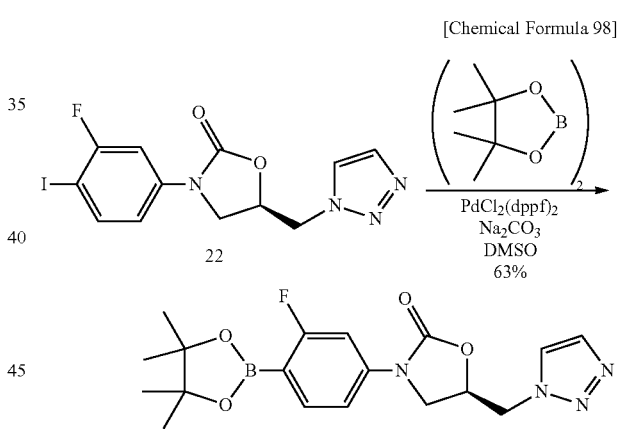

To triazole derivative (22, 6.91 g) in DMSO (160 mL), bis(pinacolato)diborane (10.34 g) and potassium acetate (5.81 g) were added and degassed with argon. Then, $PdCl_2$ (pddf).$CH_2Cl_2$ (1.53 g) was added and the reaction mixture was heated at 90° C. to 100° C. for 2 hours. To this was then added ice water, extracted with ethyl acetate, washed with water and dried under reduced pressure. The solvent was removed under reduced pressure, and the residue was purified by column chromatography (ethyl acetate) to afford 4.295 g of compound 23 as pale yellow powder (63%).

Compound 23: pale yellow powder; 1H-NMR (300 MHz, $CDCl_3$) 1.34 (s, 12H), 3.92 (dd, 9, 6, 1H), 4.19 (dd, 9, 9, 1H), 4.76 (dd, 14.5, 5, 1H), 4.82 (dd, 14.5, 4, 1H), 5.08 (dddd, 9, 6, 5, 4, 1H), 7.11 (dd, 8, 2, 1H), 7.29 (dd, 11.5, 2, 1H), 7.69 (dd, 11.5, 8, 1H), 7.71 (d, 1, 1H), 7.81 (d, 1, 1H);

LRMS m/z 388 (M+, 41), 373(7), 318(5), 289(13), 274 (23), 263(19), 175(15), 148(22), 97(35), 83(71), 80(100), 69(31), 55(88), 54(74), 41 (96).

(3) Compound 25

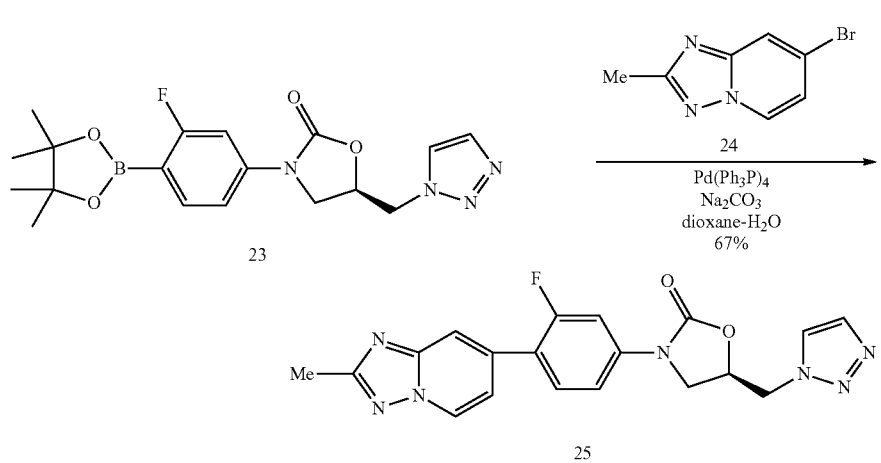

[Chemical Formula 99]

To boronic acid ester compound having triazole side chain (23, 2.63 g) and 7-bromotriazolopyridine derivative (24, 2.15 g, prepared as described in Example 4 using compound 18 of Example 5) in dioxane (50 mL) and water (12 mL), $Na_2CO_3$ (2.47 g) and $Pd(Ph_3P)_4$ (821 mg) were added and the reaction mixture was heated at 90° C. to 100° C. for 1.5 hours. The solvent was then removed under reduced pressure to reduce the volume by half, and water was added. After the resulting precipitate was filtered and dissolved in ethanol, 1.95 g of colorless compound 25 was precipitated (73%).

Compound 25: 1H-NMR (300 MHz, DMSO-d6) 2.48 (br s, 3H), 3.96 (dd, 9.5, 6, 1H), 4.30 (dd, 9.5, 9.5, 1H), 4.86 (d, 5, 2H), 5.19 (ddt, 9.5, 6, 5, 1H), 7.30 (ddd, 7, 1.5, 1.5, 1H), 7.42 (dd, 8.5, 2, 1H), 7.58 (dd, 14, 2, 1H), 7.74 (dd, 8.5, 8.5, 1H), 7.77 (d, 1, 1H), 7.86 (br s, 1H), 8.18 (d, 1, 1H), 8.88 (d, 7, 1H);

LRMS m/z 393 (M+, 7), 349 (14), 320 (6), 279 (8), 242 (10), 158 (11), 108 (21), 80 (29), 53 (100).

Example 7

Preparation of Compound 26

To boronic acid ester compound having triazole side chain (23, 3.82 g) and 7-bromotriazolopyridine compound (19, 2.32 g) in dioxane (80 mL) and water (20 mL), $Na_2CO_3$ (3.59 g) and $Pd(Ph_3P)_4$ (1.19 g) were added and heated at 90° C. to 100° C. for 1.5 hours. The solvent was removed under reduced pressure to reduce the volume by half, and water was added. After the resulting precipitation was filtered, 2.51 g of colorless compound 26 was precipitated from ethanol-chloroform (67%).

Compound 26: 1H-NMR (300 MHz, DMSO-d6) 3.97 (dd, 9.5, 5.5, 1H), 4.30 (dd, 9.5, 9.5, 1H), 4.86 (d, 5, 2H), 4.86 (ddt, 9.5, 5.5, 5, 1H), 7.37-7.46 (m, 2H), 7.60 (dd, 14, 2, 1H), 7.77 (dd, 9, 9, 1H), 7.77 (d, 1, 1H), 8.01 (br d, 1, 1H), 8.18 (d, 1, 1H), 8.54 (s, 1H), 9.02 (d, 7, 1H);

LRMS m/z 379 (M+, 11), 335 (15), 306 (7), 266 (13), 228 (13), 158 (12), 108 (30), 53 (100).

The following compounds were prepared according to the procedure as described in the above Examples.

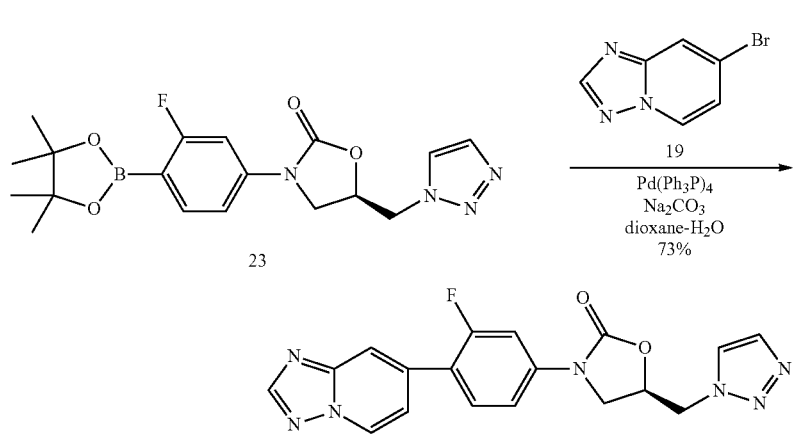

[Chemical Formula 100]

TABLE 1
| Example | Structure | LCMS (ESI) m/z (M + H)+ |
|---------|-----------|-------------------------|
| 8 | 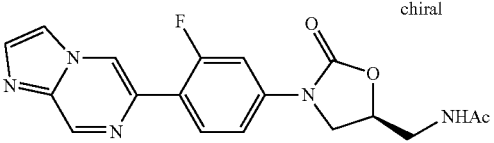 [SMILES: CC(=O)NC[C@H]1CN(c2ccc(-c3cn4ccnc4cn3)c(F)c2)C(=O)O1] chiral | 369.98 |
| 9 | 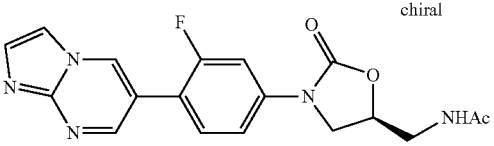 [SMILES: CC(=O)NC[C@H]1CN(c2ccc(-c3cnc4nccn4c3)c(F)c2)C(=O)O1] chiral | 369.98 |
| 10 | 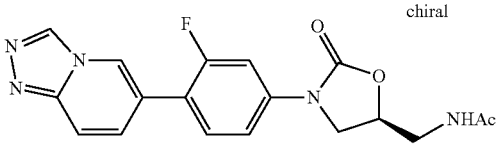 [SMILES: CC(=O)NC[C@H]1CN(c2ccc(-c3ccc4nncn4c3)c(F)c2)C(=O)O1] chiral | 370.1 |
| 11 | 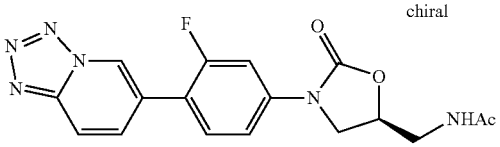 [SMILES: CC(=O)NC[C@H]1CN(c2ccc(-c3ccc4nnnn4c3)c(F)c2)C(=O)O1] chiral | 371 |
| 12 | 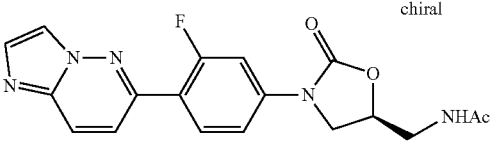 [SMILES: CC(=O)NC[C@H]1CN(c2ccc(-c3ccc4nccn4n3)c(F)c2)C(=O)O1] chiral | 369.91 |
| 13 | 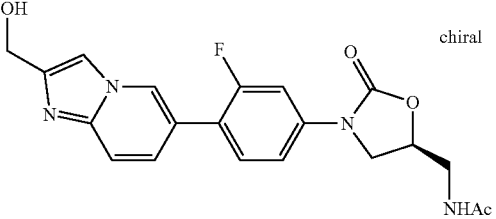 [SMILES: CC(=O)NC[C@H]1CN(c2ccc(-c3ccc4nc(CO)cn4c3)c(F)c2)C(=O)O1] chiral | 398.93 |
TABLE 2
| | | |
|---|---|---|
| 14 | 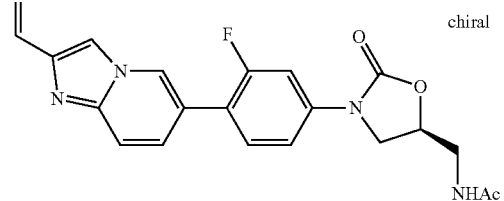 chiral | 396.9 |

TABLE 2-continued

| 15 | [structure: 2-(trifluoromethyl)imidazo[1,2-a]pyridine linked to 2-fluorophenyl-oxazolidinone-CH2NHAc], chiral | 437.55 |
| 16 | [structure: 2-tert-butyl-imidazo[1,2-a]pyridine linked to 2-fluorophenyl-oxazolidinone-CH2NHAc], chiral | 424.98 |
| 17 | [structure: 2-cyano-imidazo[1,2-a]pyridine linked to 2-fluorophenyl-oxazolidinone-CH2NHAc], chiral | 393.9 |
| 18 | [structure: imidazo[1,2-a]pyridine linked to 2-fluorophenyl-oxazolidinone-CH2NHAc], chiral | 368.93 |
| 19 | [structure: 2-carboxamido-imidazo[1,2-a]pyridine linked to 2-fluorophenyl-oxazolidinone-CH2NHAc], chiral | 411.9 |

TABLE 3

| 20 | [structure: 2-carboxylic acid-imidazo[1,2-a]pyridine linked to 2-fluorophenyl-oxazolidinone-CH2NHAc], chiral | 412.91 |
| 21 | [structure: 2-(morpholinomethyl)-imidazo[1,2-a]pyridine linked to 2-fluorophenyl-oxazolidinone-CH2NHAc], chiral | 467.99 |

TABLE 3-continued
| | | | |
|---|---|---|---|
| 22 | 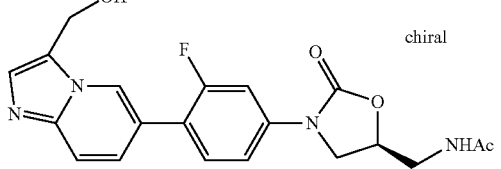 | chiral | 398.99 |
| 23 | 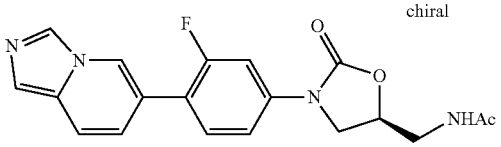 [SMILES: CC(=O)NC[C@H]1CN(c2ccc(-c3ccc4cncn4c3)c(F)c2)C(=O)O1] | chiral | 368.93 |
| 24 | 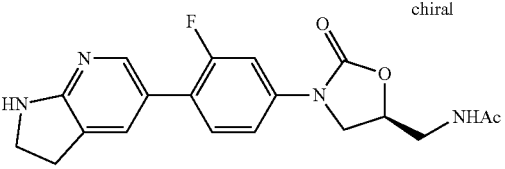
·HCl | chiral | 370.96 |
| 25 | 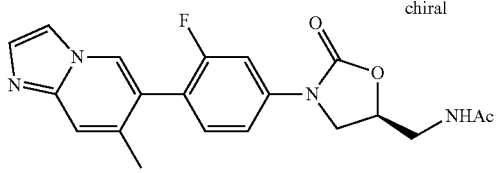 [SMILES: CC(=O)NC[C@H]1CN(c2ccc(-c3cn4ccnc4cc3C)c(F)c2)C(=O)O1] | chiral | 382.99 |
TABLE 4
| | | | |
|---|---|---|---|
| 26 | 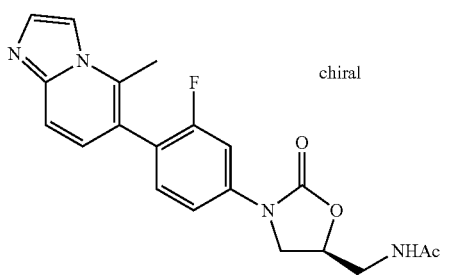 [SMILES: CC(=O)NC[C@H]1CN(c2ccc(-c3ccc4nccn4c3C)c(F)c2)C(=O)O1] | chiral | 382.96 |
| 27 | 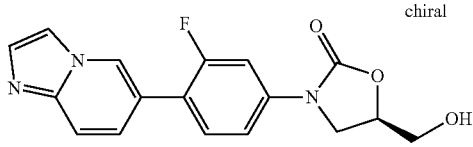 [SMILES: O=C1O[C@@H](CO)CN1c1ccc(-c2ccc3nccn3c2)c(F)c1] | chiral | 328.05 |
| 28 | 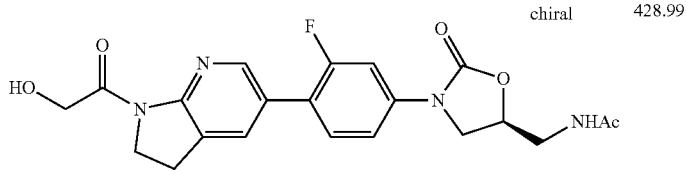 | chiral | 428.99 |

TABLE 4-continued

| # | Structure | MS |
|---|---|---|
| 29 | imidazo[1,2-a]pyridine-3-carbonitrile linked to 3-fluoro-4-phenyl-oxazolidinone-CH2-NHAc (chiral) | 393.96 |
| 30 | 7,8-dimethyl-imidazo[1,2-a]pyridine linked to 3-fluoro-4-phenyl-oxazolidinone-CH2-NHAc (chiral) | 396.98 |
| 31 | 8-methyl-imidazo[1,2-a]pyridine linked to 3-fluoro-4-phenyl-oxazolidinone-CH2-NHAc | 383.03 |

TABLE 5

| # | Structure | MS |
|---|---|---|
| 32 | imidazo[1,2-a]pyridine linked to phenyl-oxazolidinone-CH2-NHAc (chiral) | 351.00 |
| 33 | imidazo[1,2-a]pyridine-3-carboxamide linked to 3-fluoro-4-phenyl-oxazolidinone-CH2-NHAc (chiral) | 411.97 |
| 34 | imidazo[1,5-a]pyridine linked to 3-fluoro-4-phenyl-oxazolidinone-CH2-NHAc (chiral) | 369.01 |
| 35 | 3-(thiomorpholine-4-carbonyl)-imidazo[1,2-a]pyridine linked to 3-fluoro-4-phenyl-oxazolidinone-CH2-NHAc (chiral) | 498.10 |

TABLE 5-continued
| | | | |
|---|---|---|---|
| 36 | 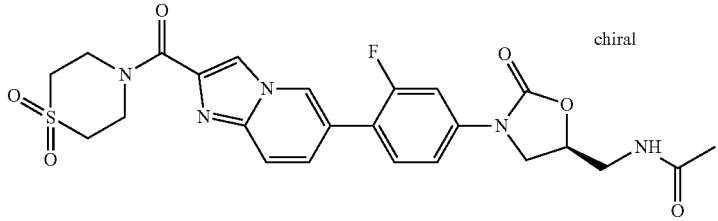 [SMILES: CC(=O)NC[C@H]1CN(c2ccc(-c3ccc4nc(C(=O)N5CCS(=O)(=O)CC5)cn4c3)c(F)c2)C(=O)O1] | chiral | 530.10 |
| 37 | 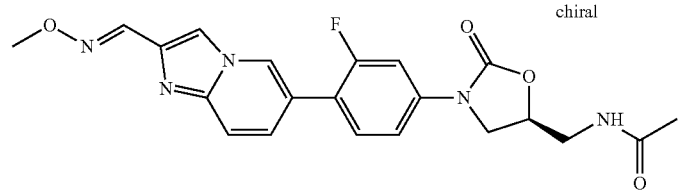 [SMILES: CO/N=C/c1cn2cc(-c3ccc(N4C[C@H](CNC(C)=O)OC4=O)cc3F)ccc2n1] | chiral | 425.99 |
TABLE 6
| | | | |
|---|---|---|---|
| 38 | 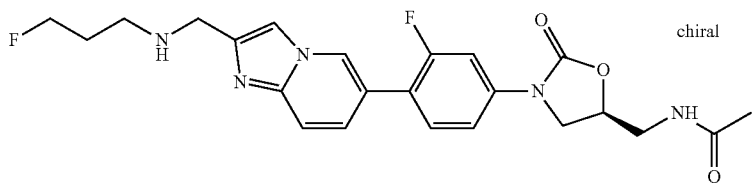 [SMILES: CC(=O)NC[C@H]1CN(c2ccc(-c3ccc4nc(CNCCCF)cn4c3)c(F)c2)C(=O)O1 ; "chiral"] | chiral | 458.20 |
| 39 | 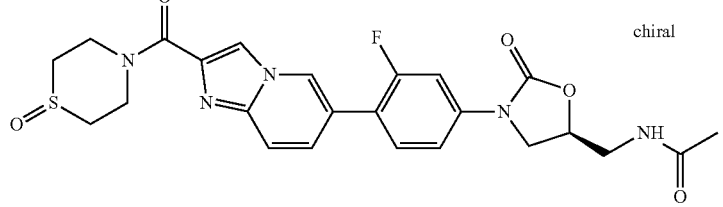 | chiral | 514.05 |
| 40 | 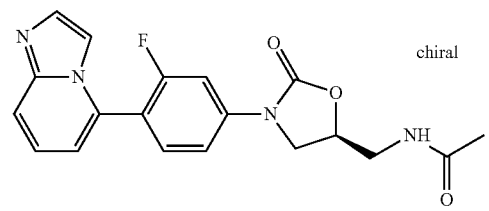 [SMILES: CC(=O)NC[C@H]1CN(c2ccc(-c3cccc4nccn34)c(F)c2)C(=O)O1 ; "chiral"] | chiral | 369.08 |
| 41 | 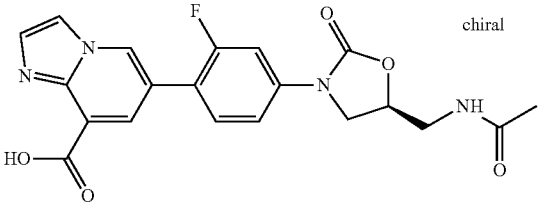 [SMILES: CC(=O)NC[C@H]1CN(c2ccc(-c3cc(C(=O)O)c4nccn4c3)c(F)c2)C(=O)O1 ; "chiral"] | chiral | 413.45 |
| 42 | 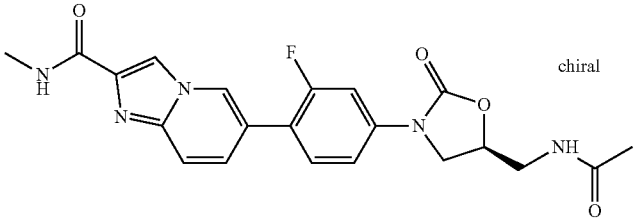 [SMILES: CNC(=O)c1cn2cc(-c3ccc(N4C[C@H](CNC(C)=O)OC4=O)cc3F)ccc2n1 ; "chiral"] | chiral | 426.07 |

TABLE 6-continued
| 43 | 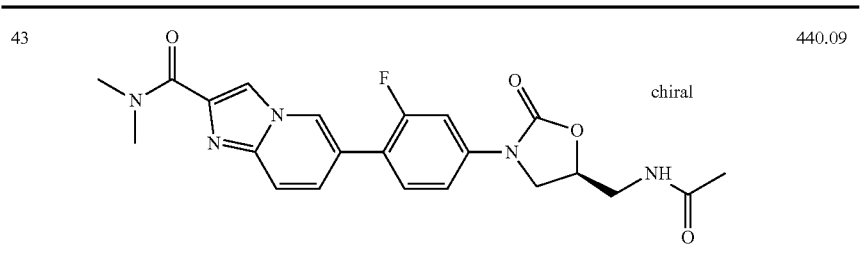 | 440.09 chiral |
TABLE 7
| 44 | 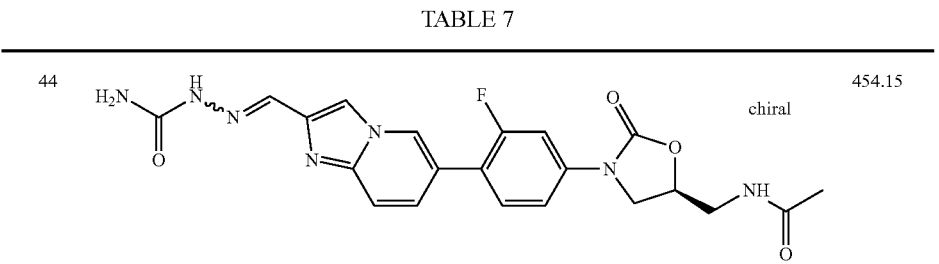 | 454.15 chiral |
| 45 | 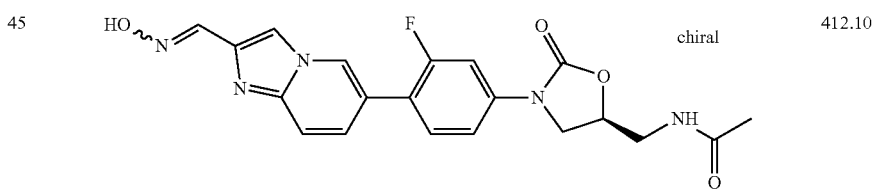 | 412.10 chiral |
| 46 | 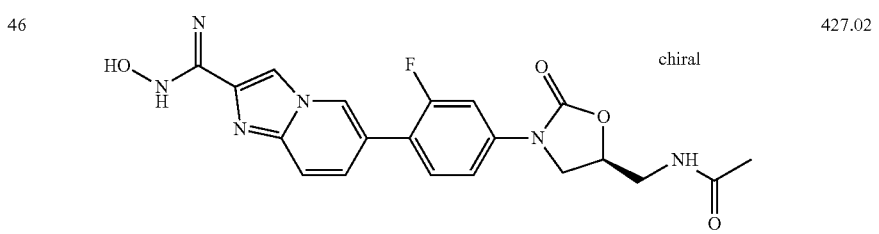 | 427.02 chiral |
| 47 | 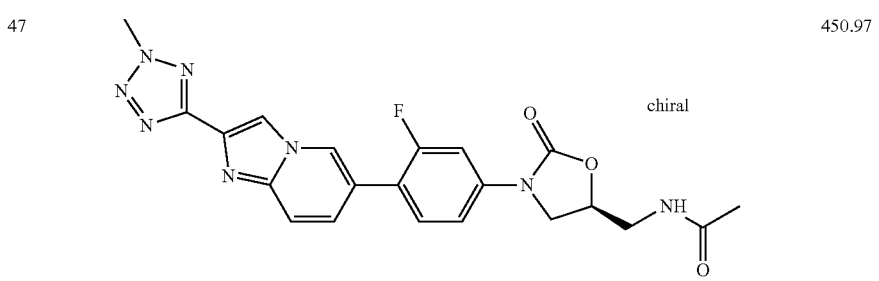 | 450.97 chiral |
| 48 | 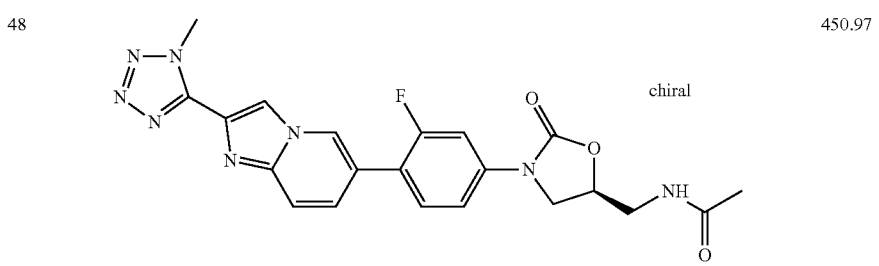 | 450.97 chiral |

TABLE 7-continued
| 49 | 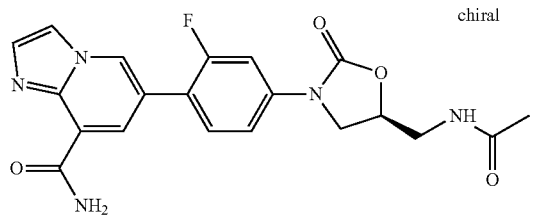 [SMILES: "chiral" ; CC(=O)NC[C@H]1CN(c2ccc(-c3cc(C(N)=O)c4nccn4c3)c(F)c2)C(=O)O1] | chiral | 411.97 |
TABLE 8
| 50 | 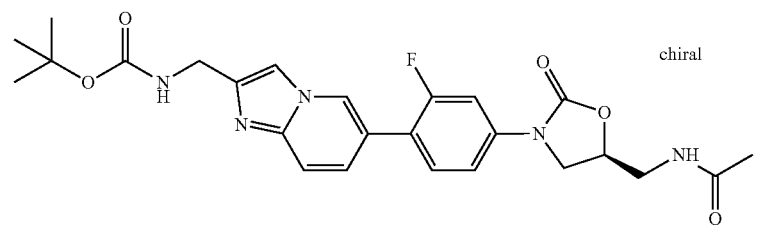 [SMILES: CC(=O)NC[C@H]1CN(c2ccc(-c3ccc4nc(CNC(=O)OC(C)(C)C)cn4c3)c(F)c2)C(=O)O1 ; "chiral"] | chiral | 498.23 |
| 51 | 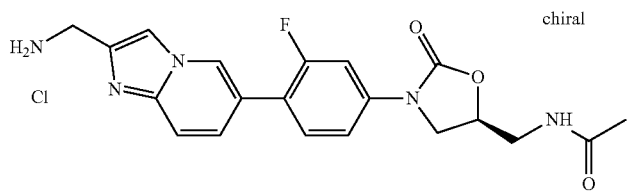 [SMILES: "chiral" ; CC(=O)NC[C@H]1CN(c2ccc(-c3ccc4nc(CN)cn4c3)c(F)c2)C(=O)O1 ; Cl] | chiral | 398.24 |
| 52 | 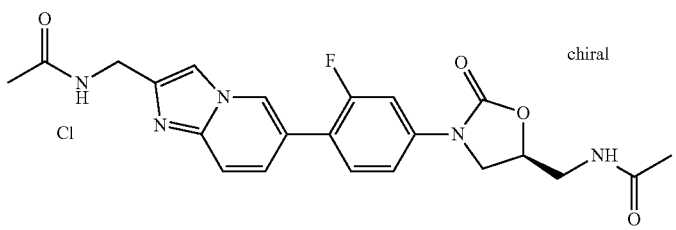 [SMILES: CC(=O)NCc1cn2cc(-c3ccc(N4C[C@H](CNC(C)=O)OC4=O)cc3F)ccc2n1 ; Cl ; "chiral"] | chiral | 440.35 |
| 53 | 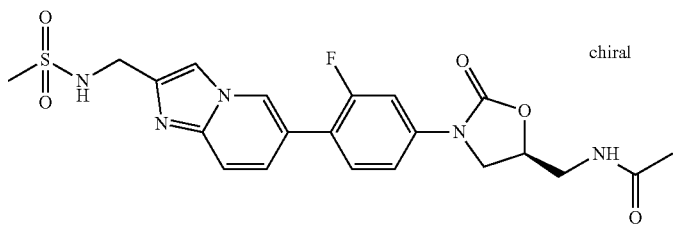 [SMILES: CC(=O)NC[C@H]1CN(c2ccc(-c3ccc4nc(CNS(C)(=O)=O)cn4c3)c(F)c2)C(=O)O1 ; "chiral"] | chiral | 476.10 |
| 54 | 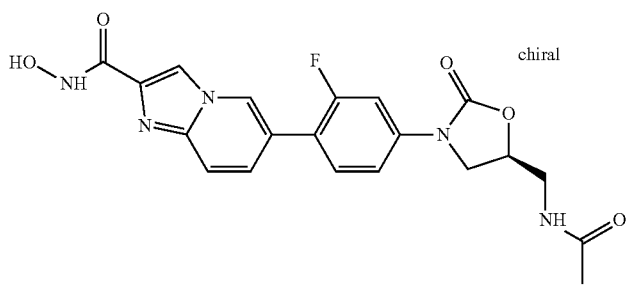 [SMILES: CC(=O)NC[C@H]1CN(c2ccc(-c3ccc4nc(C(=O)NO)cn4c3)c(F)c2)C(=O)O1 ; "chiral"] | chiral | 427.99 |

TABLE 8-continued
| 55 | 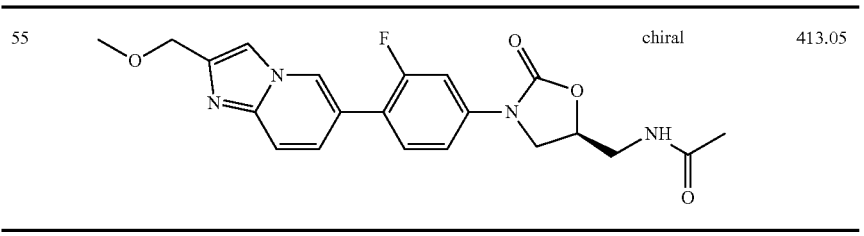 | chiral | 413.05 |
TABLE 9
| 56 | 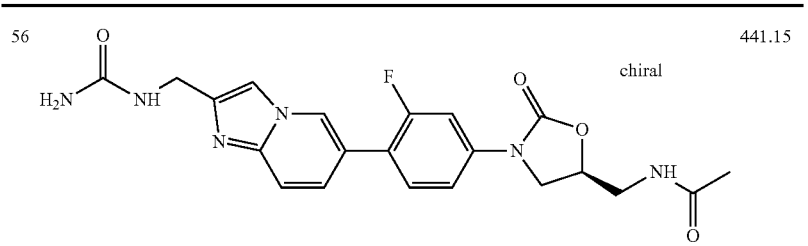 | chiral | 441.15 |
| 57 | 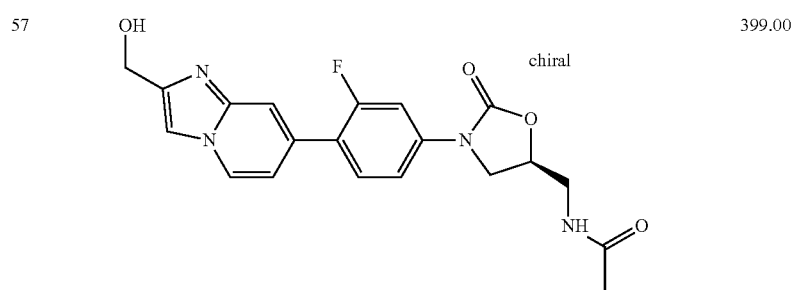 | chiral | 399.00 |
| 58 | 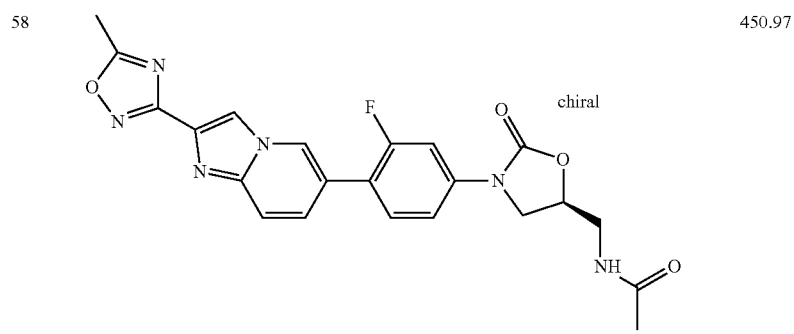 | chiral | 450.97 |
| 59 | 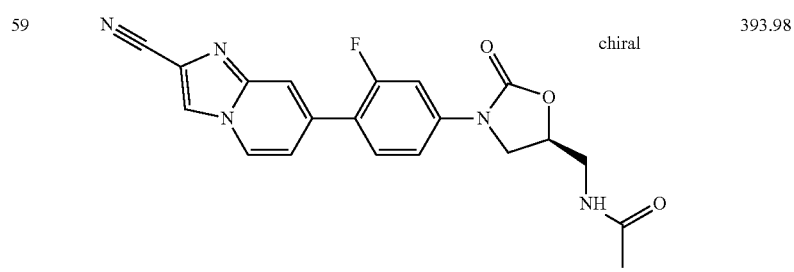 | chiral | 393.98 |

TABLE 10

| Example | Structure | | LCMS(ESI) m/z (M + H) + |
|---|---|---|---|
| 60 | (imidazo[1,2-a]pyridine with CHO, F-phenyl, oxazolidinone-CH2NHAc) | chiral | 397.34 |
| 61 | (imidazo[1,2-a]pyridine with CN, F-phenyl, oxazolidinone-CH2NHAc) | chiral | 394.44 |
| 62 | (imidazo[1,2-a]pyridine with CH2OH, F-phenyl, oxazolidinone-CH2NHAc) | chiral | 399.41 |
| 63 | (imidazo[1,2-a]pyridine with 3-CHO, F-phenyl, oxazolidinone-CH2NHAc) | chiral | 397.38 |
| 64 | (imidazo[1,2-a]pyridine with 3-CN, F-phenyl, oxazolidinone-CH2NHAc) | chiral | 394.39 |
| 65 | (imidazo[1,2-a]pyridine with 3-CH2OH, F-phenyl, oxazolidinone-CH2NHAc) | chiral | 399.44 |
| 66 | (imidazo[1,2-a]pyridine with 2-COOH, F-phenyl, oxazolidinone-CH2NHAc) | chiral | 413.47 |

TABLE 11

| # | Structure | MW |
|---|---|---|
| 67 | (imidazo[1,2-a]pyridine-2-carboxamide, 7-[2-fluoro-4-(oxazolidinone-NHAc)phenyl], chiral) | 412.00 |
| 68 | (imidazo[1,2-a]pyridine, 7-[2-fluoro-4-(oxazolidinone-CH2-triazole)phenyl], chiral) | 378.98 |
| 69 | (imidazo[1,2-a]pyridine, 7-[3-fluoro-pyridin-6-yl-(oxazolidinone-CH2-NHC(O)OCH3)], chiral) | 384.98 |
| 70 | (ethyl-NH-C(O)-NH-imidazo[1,2-a]pyridin-2-yl, 6-[2-fluoro-4-(oxazolidinone-NHAc)phenyl], chiral) | 455.06 |
| 71 | (1-methyl-tetrazol-5-yl-imidazo[1,2-a]pyridin-2-yl, 7-[2-fluoro-4-(oxazolidinone-NHAc)phenyl], chiral) | 451.04 |
| 72 | (2-methyl-tetrazol-5-yl-imidazo[1,2-a]pyridin-2-yl, 7-[2-fluoro-4-(oxazolidinone-NHAc)phenyl], chiral) | 451.10 |
| 73 | (triazol-CH2-NH-CH2-imidazo[1,2-a]pyridin-3-yl, 6-[2-fluoro-4-(oxazolidinone-NHAc)phenyl], chiral, ClH) | 479.30 |

TABLE 12

| # | Structure | MW |
|---|---|---|
| 74 | (H2N-NH-C(O)-imidazo[1,2-a]pyridine-2-yl, 6-[2-fluoro-4-(oxazolidinone-NHAc)phenyl], chiral) | 427.30 |

TABLE 12-continued
| | | |
|---|---|---|
| 75 | 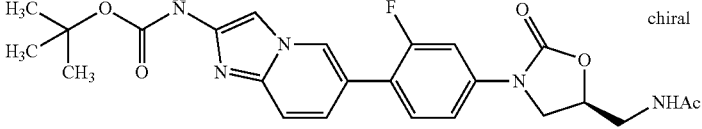 chiral | 484.14 |
| 76 | 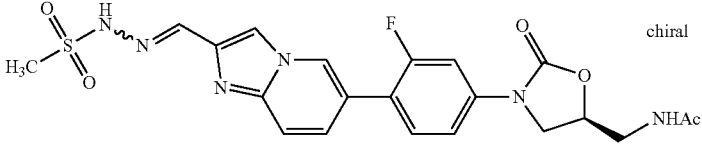 [SMILES: CC(=O)NC[C@H]1CN(c2ccc(-c3ccc4nc(C=NNS(C)(=O)=O)cn4c3)c(F)c2)C(=O)O1 ; "chiral"] chiral | 489.05 |
| 77 | 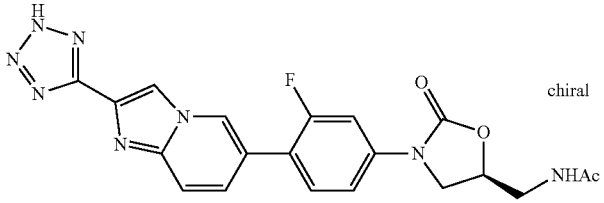 [SMILES: CC(=O)NC[C@H]1CN(c2ccc(-c3ccc4nc(-c5nn[nH]n5)cn4c3)c(F)c2)C(=O)O1 ; "chiral"] chiral | 437.00 |
| 78 | 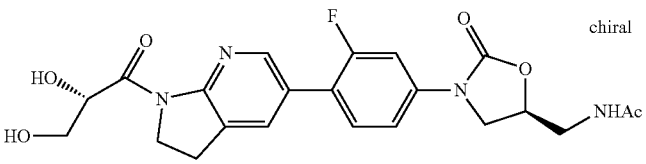 [SMILES: CC(=O)NC[C@H]1CN(c2ccc(-c3cnc4c(c3)CCN4C(=O)[C@@H](O)CO)c(F)c2)C(=O)O1 ; "chiral"] chiral | 459.22 |
| 79 | 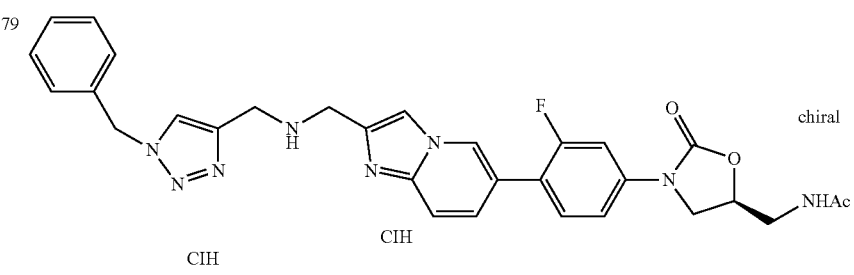 chiral | 569.20 |
| 80 | 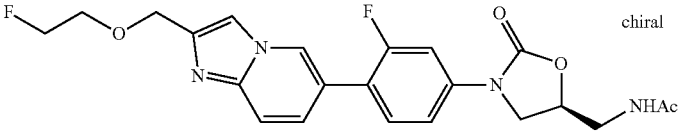 [SMILES: CC(=O)NC[C@H]1CN(c2ccc(-c3ccc4nc(COCCF)cn4c3)c(F)c2)C(=O)O1 ; "chiral"] chiral | 445.30 |
TABLE 13
| | | |
|---|---|---|
| 81 | 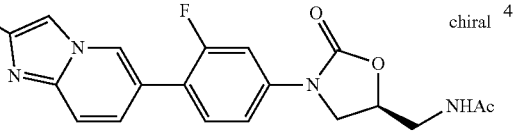 chiral | 473.15 |
| 82 | 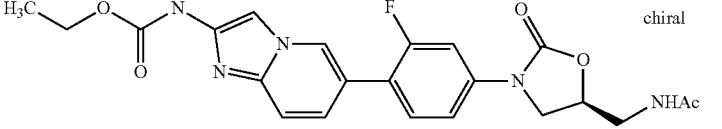 chiral | 456.19 |

TABLE 13-continued
| 83 | 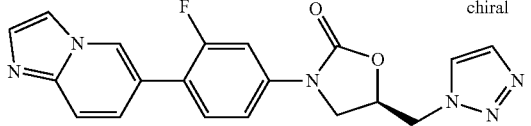 | chiral | 424.20 |
| 84 | 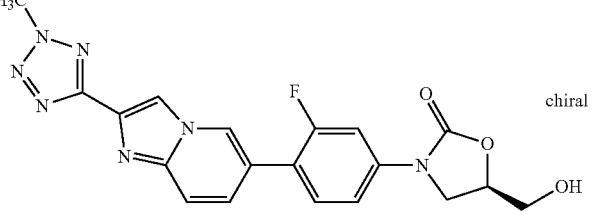 | chiral | 410.18 |
| 85 | 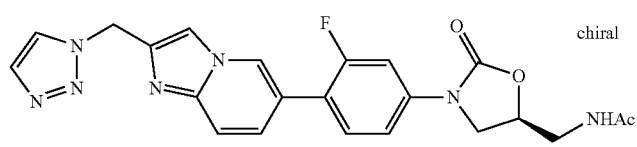 [SMILES: CC(=O)NC[C@H]1CN(c2ccc(-c3ccc4nc(Cn5ccnn5)cn4c3)c(F)c2)C(=O)O1 ; "chiral"] | chiral | 451.18 |
| 86 | 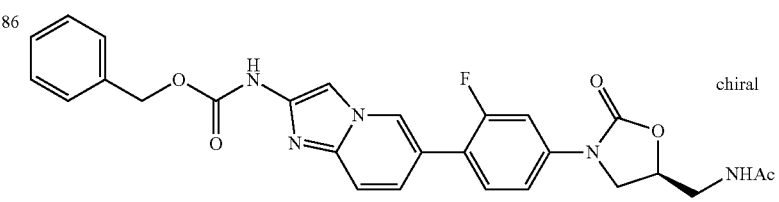 | chiral | 518.15 |
| 87 | 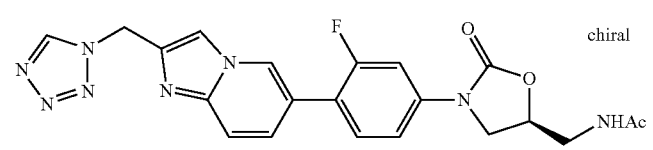 [SMILES: CC(=O)NC[C@H]1CN(c2ccc(-c3ccc4nc(Cn5cnnn5)cn4c3)c(F)c2)C(=O)O1 ; "chiral"] | chiral | 451.18 |
| 88 | 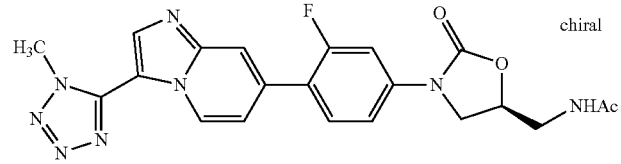 [SMILES: CC(=O)NC[C@H]1CN(c2ccc(-c3ccn4c(-c5nnnn5C)cnc4c3)c(F)c2)C(=O)O1 ; "chiral"] | chiral | 451.19 |
TABLE 14
| 89 | 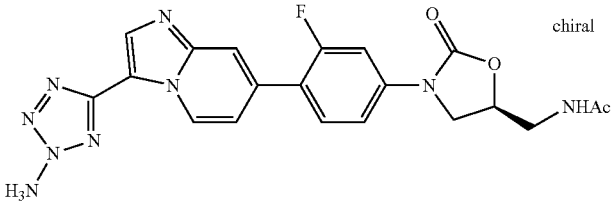 [SMILES: CC(=O)NC[C@H]1CN(c2ccc(-c3ccn4c(-c5nnn(N)n5)cnc4c3)c(F)c2)C(=O)O1 ; "chiral"] | chiral | 451.19 |
| 90 | 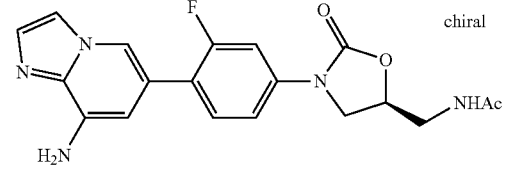 | chiral | 384.16 |

TABLE 14-continued

| | | |
|---|---|---|
| 91 | [structure] | chiral 437.17 |
| 92 | [structure] | chiral 395.11 |
| 93 | [structure] | 442.15 chiral |
| 94 | [structure] | 426.22 chiral |

TABLE 15

| | | |
|---|---|---|
| 95 | [structure] | 442.12 chiral |
| 96 | [structure] | 519.15 chiral |
| 97 | [structure] | 504.20 chiral |
| 98 | [structure] | 445.05 chiral |
| 99 | [structure] | 328.08 chiral |

TABLE 15-continued

| # | Structure | | Value |
|---|---|---|---|
| 100 | (3-fluoropropoxymethyl-imidazo[1,2-a]pyridine linked to fluorophenyl-oxazolidinone-NHAc) | chiral | 459.10 |
| 101 | (hydroxyimino-methyl imidazo[1,2-a]pyridine linked to fluorophenyl-oxazolidinone-NHAc) | chiral | 412.05 |
| 102 | (methyl carbamate-ethoxy-imino-methyl imidazo[1,2-a]pyridine linked to fluorophenyl-oxazolidinone-NHAc) | chiral | 513.05 |
| 103 | (carboxamide-imidazo[1,2-a]pyridine linked to fluorophenyl-oxazolidinone-NHAc) | chiral | 412.13 |

TABLE 16

| # | Structure | | Value |
|---|---|---|---|
| 104 | (2-hydroxyethylamino-carbonyl-imidazo[1,2-a]pyridine linked to fluorophenyl-oxazolidinone-NHAc) | chiral | 456.14 |
| 105 | (2,3-dihydroxypropylamino-carbonyl-imidazo[1,2-a]pyridine linked to fluorophenyl-oxazolidinone-NHAc) | chiral | 486.21 |
| 106 | (2,3-dihydroxypropylamino-carbonyl-imidazo[1,2-a]pyridine linked to fluorophenyl-oxazolidinone-NHAc) | chiral | 486.21 |
| 107 | (morpholino-oxoethoxy-imino-methyl imidazo[1,2-a]pyridine linked to fluorophenyl-oxazolidinone-NHAc) | chiral | 539.10 |
| 108 | (dimethylamino-ethoxy-imino-methyl imidazo[1,2-a]pyridine linked to fluorophenyl-oxazolidinone-NHAc) | chiral | 483.10 |

TABLE 16-continued
| | | |
|---|---|---|
| 109 | 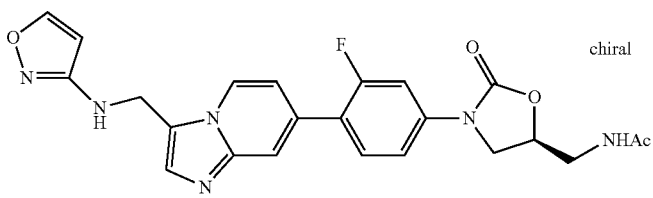 [SMILES: CC(=O)NC[C@H]1CN(c2ccc(-c3ccn4c(CNc5ccon5)cnc4c3)c(F)c2)C(=O)O1 ; "chiral"] | 465.09 chiral |
| 110 | 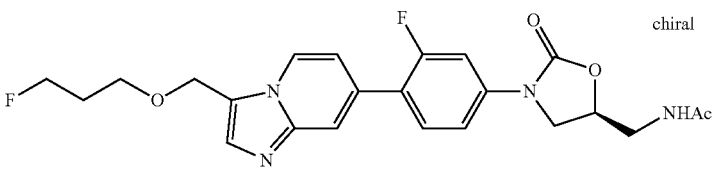 [SMILES: CC(=O)NC[C@H]1CN(c2ccc(-c3ccn4c(COCCCF)cnc4c3)c(F)c2)C(=O)O1 ; "chiral"] | 459.05 chiral |
| 111 | 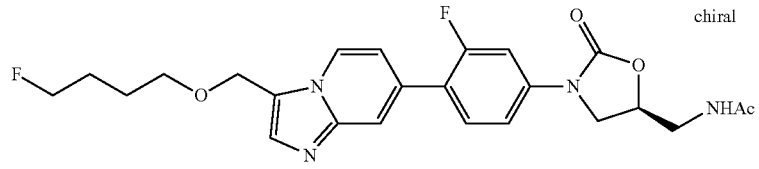 [SMILES: CC(=O)NC[C@H]1CN(c2ccc(-c3ccn4c(COCCCCF)cnc4c3)c(F)c2)C(=O)O1 ; "chiral"] | 473.10 chiral |
| 112 | 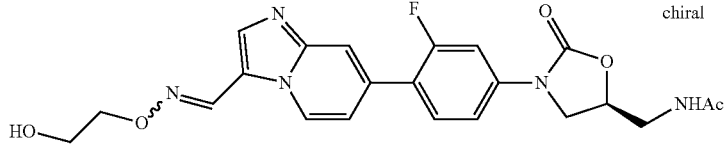 [SMILES: CC(=O)NC[C@H]1CN(c2ccc(-c3ccn4c(C=NOCCO)cnc4c3)c(F)c2)C(=O)O1 ; "chiral"] | 456.05 chiral |
TABLE 17
| | | |
|---|---|---|
| 113 | 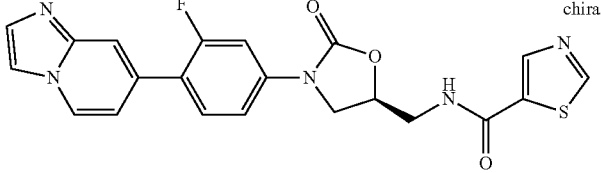 | 438.07 chiral |
| 114 | 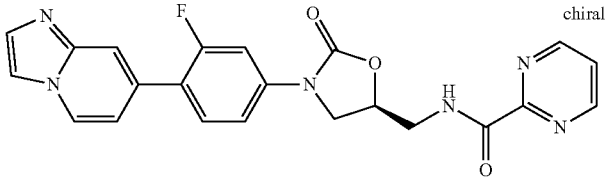 | 433.12 chiral |
| 115 | 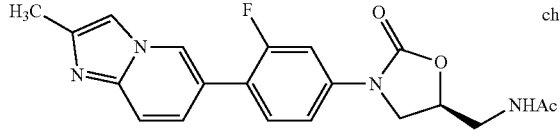 | 383.11 chiral |
| 116 | 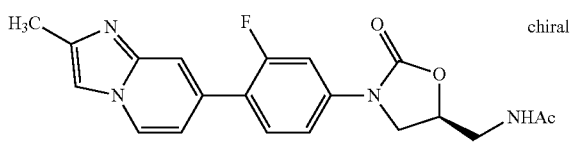 [SMILES: CC(=O)NC[C@H]1CN(c2ccc(-c3ccn4cc(C)nc4c3)c(F)c2)C(=O)O1 ; "chiral"] | 383.11 chiral |

TABLE 17-continued
| | | | |
|---|---|---|---|
| 117 | 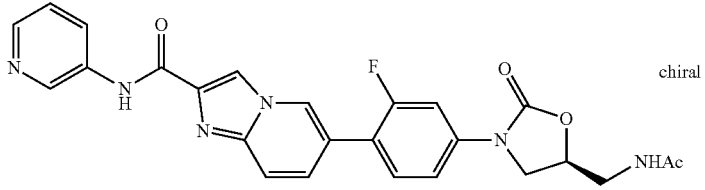 [SMILES: CC(=O)NC[C@H]1CN(c2ccc(-c3ccc4nc(C(=O)Nc5cccnc5)cn4c3)c(F)c2)C(=O)O1 ; "chiral"] | 489.14 chiral | |
| 118 | 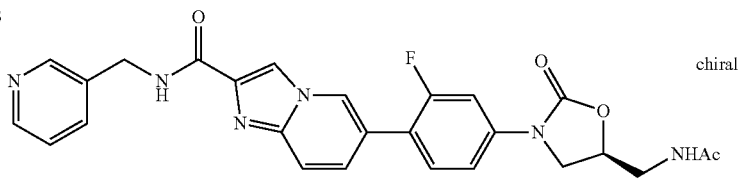 | 503.16 chiral | |
| 119 | 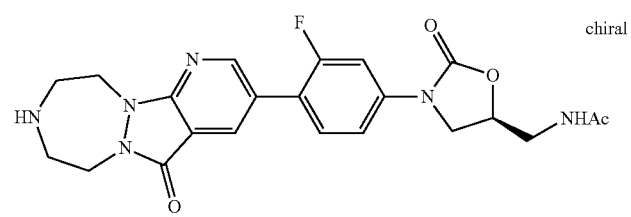 [SMILES: CC(=O)NC[C@H]1CN(c2ccc(-c3cnc4c(c3)c(=O)n3n4CCNCC3)c(F)c2)C(=O)O1 ; "chiral"] | chiral 455.16 | |
TABLE 18
| | | | |
|---|---|---|---|
| 120 | 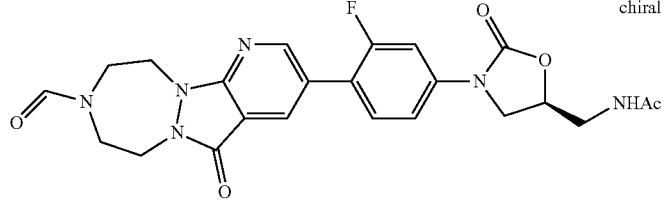 [SMILES: "chiral" ; CC(=O)NC[C@H]1CN(c2ccc(-c3cnc4c(c3)c(=O)n3n4CCN(C=O)CC3)c(F)c2)C(=O)O1] | chiral 483.16 | |
| 121 | 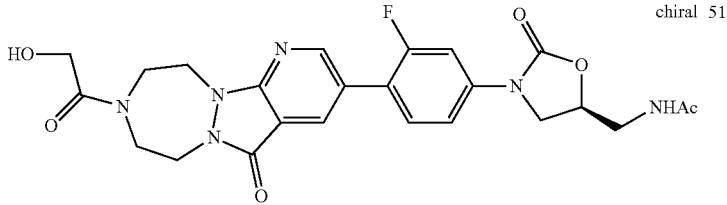 | chiral 513.20 | |
| 122 | 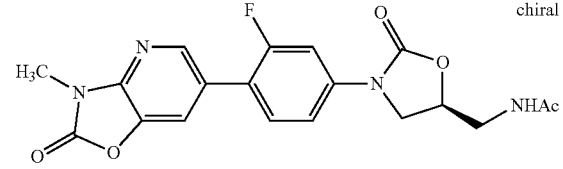 [SMILES: "chiral" ; CC(=O)NC[C@H]1CN(c2ccc(-c3cnc4c(c3)oc(=O)n4C)c(F)c2)C(=O)O1] | chiral 401.10 | |
| 123 | 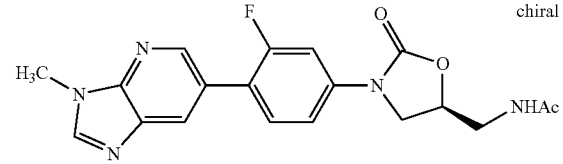 [SMILES: "chiral" ; CC(=O)NC[C@H]1CN(c2ccc(-c3cnc4c(c3)ncn4C)c(F)c2)C(=O)O1] | chiral 384.16 | |

TABLE 19

| Example | Structure | | LCMS (ESI) m/z (M + H) + |
|---|---|---|---|
| 124 | [structure] | chiral | 385.14 |
| 125 | [structure] | chiral | 370.14 |
| 126 | [structure] | chiral | 443.21 |
| 127 | [structure] | chiral | 370.14 |
| 128 | [structure] | chiral | 398.10 |
| 129 | [structure] | chiral | 413.19 |
| 130 | [structure] | chiral | 384.14 |
| 131 | [structure] | chiral | 412.12 |

TABLE 20

| | | | |
|---|---|---|---|
| 132 | [structure] | chiral | 394.13 |
| 133 | [structure] | chiral | 343.11 |
| 134 | [structure] ClH | chiral | 399.10 |
| 135 | [structure] | chiral | 402.13 |
| 136 | [structure] | chiral | 400.13 |
| 137 | [structure] | chiral | 384.16 |
| 138 | [structure] | chiral | 371.11 |
| 139 | [structure] | chiral | 409.12 |
| 140 | [structure] | chiral | 352.14 |

TABLE 21
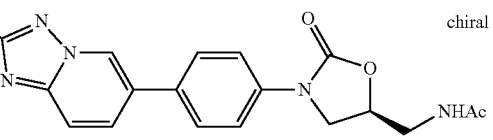
The present invention further provides the following compounds.
Example A
[Chemical Formula 101]
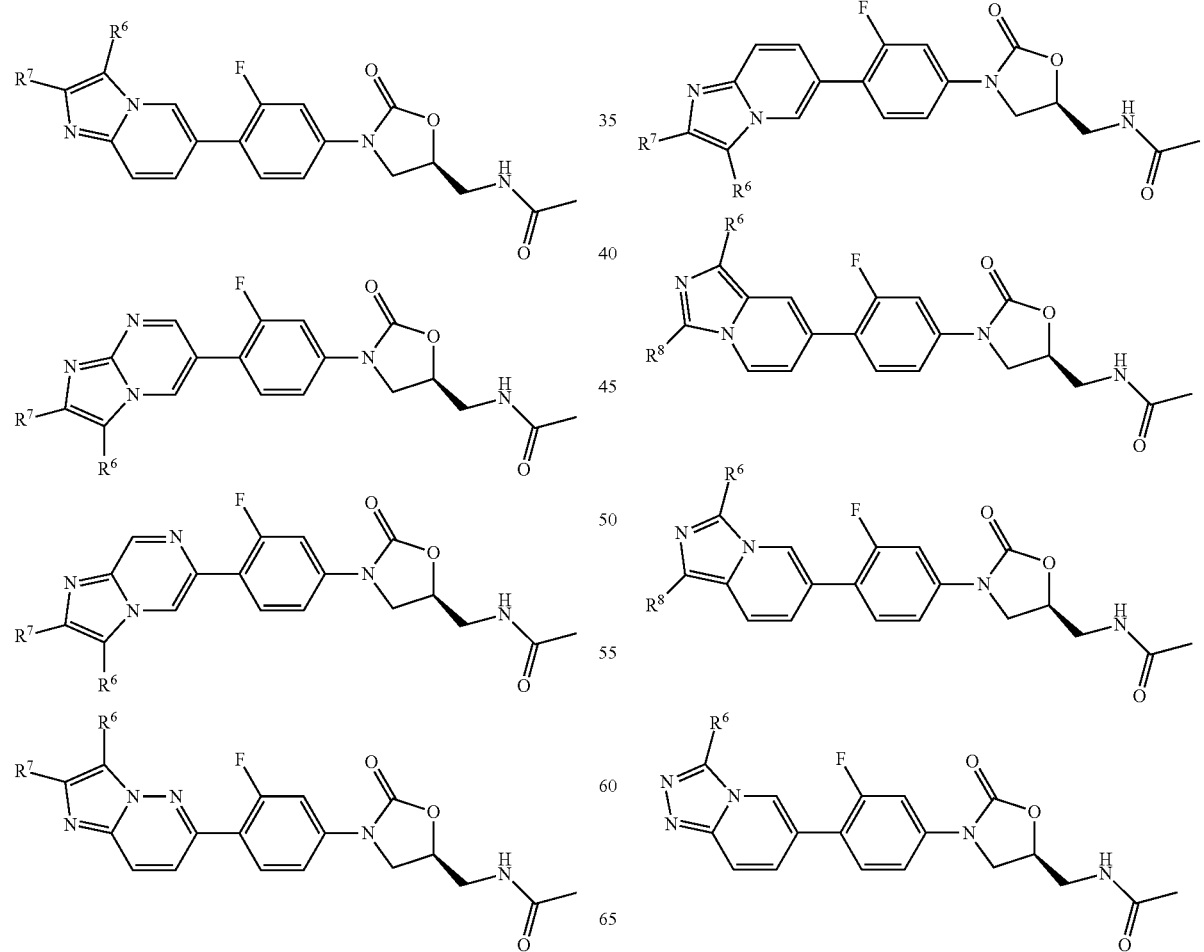

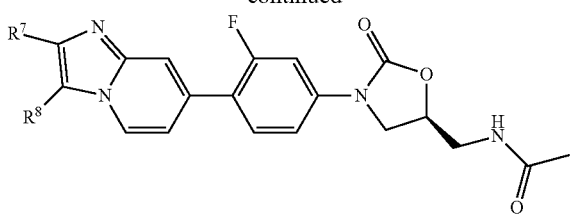
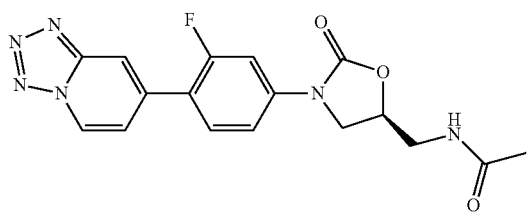
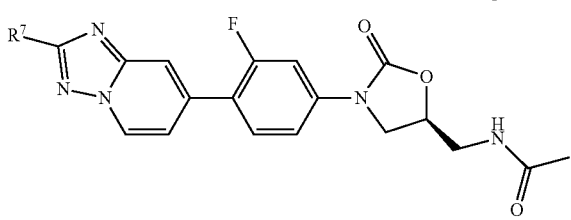
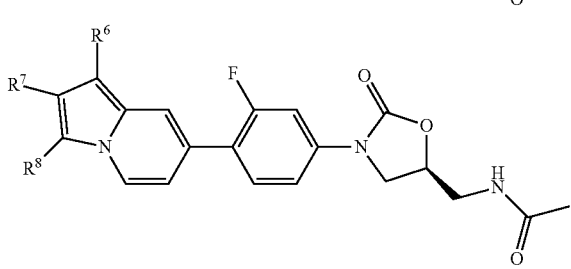
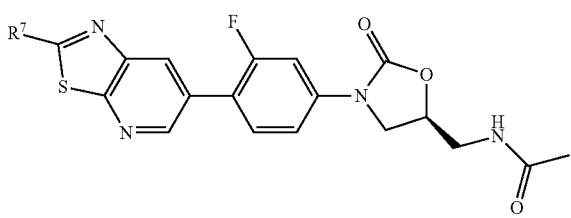
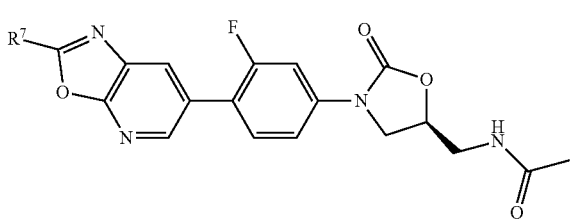
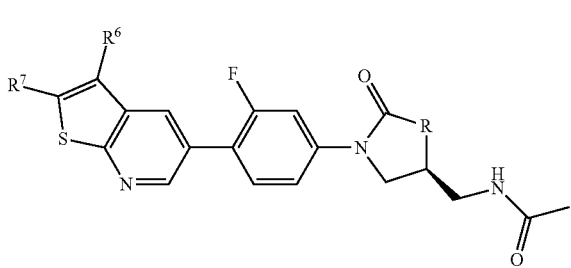
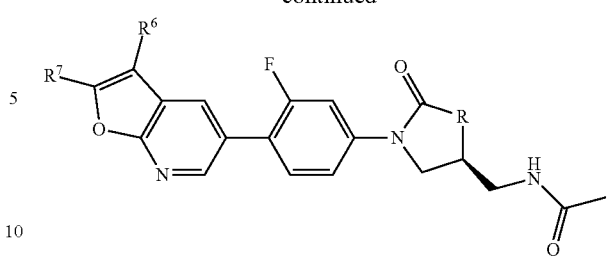
wherein $R^6$, $R^7$ and/or $R^8$ are independently selected from the substituents as listed in Example C.
Example A-1
The following preferred embodiments of the compounds of Example A are provided.
[Chemical Formula 102]
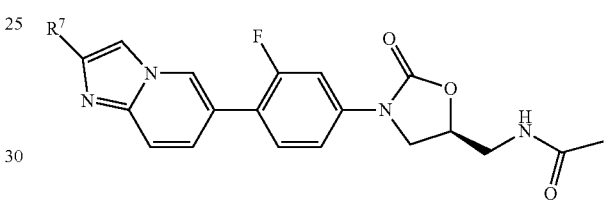
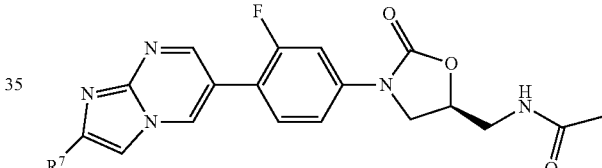
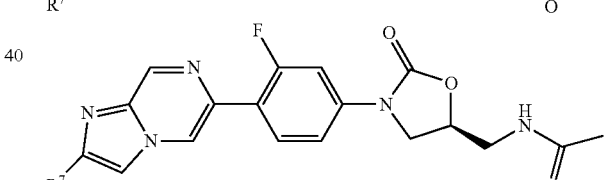
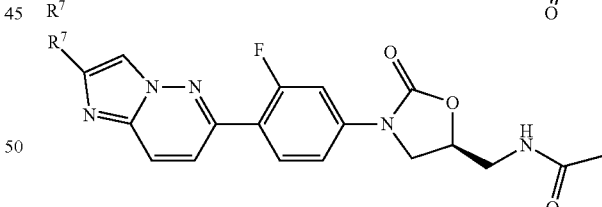
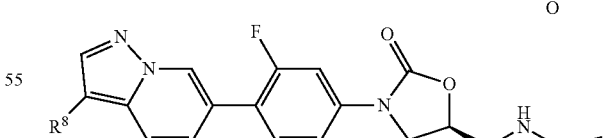
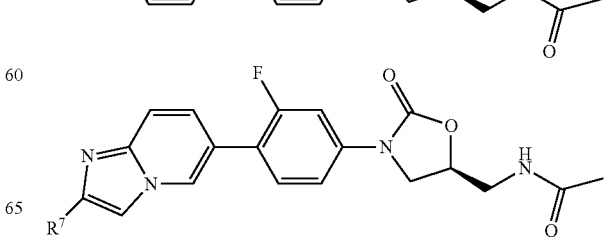

-continued
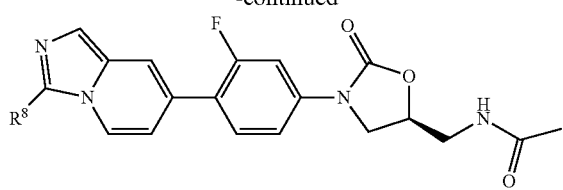
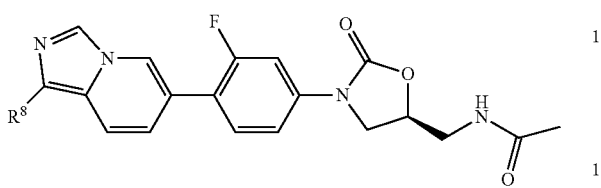
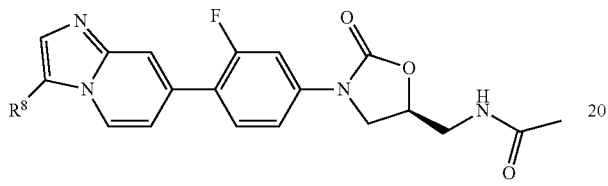
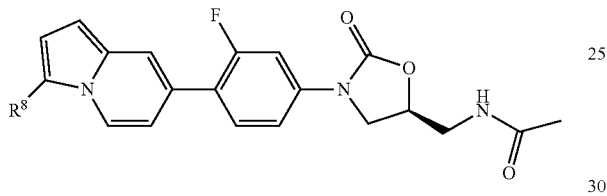
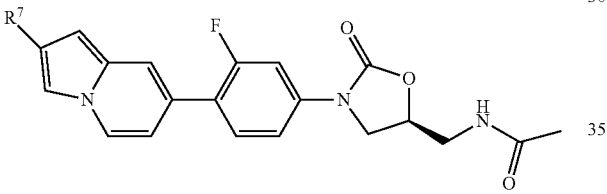
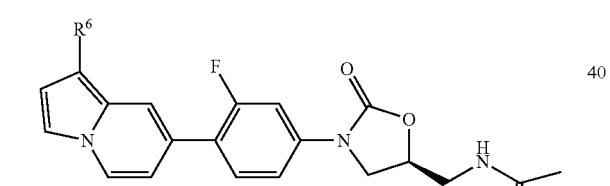
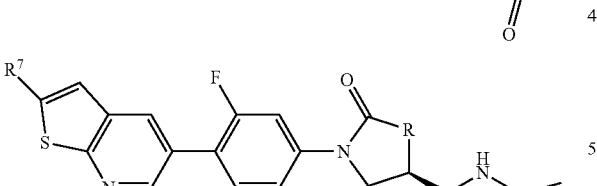
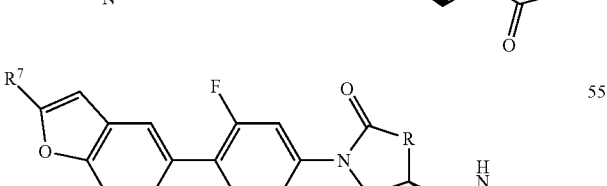
wherein $R^6$, $R^7$ or $R^8$ are independently selected from the substituents listed in Example C.
Example A-2
The following preferred embodiments of the compounds of Example A are provided.
[Chemical Formula 103]
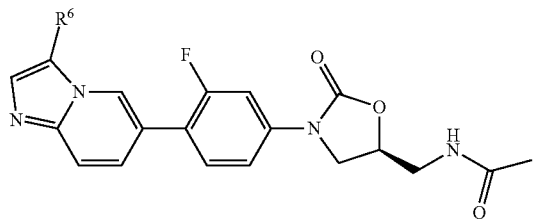
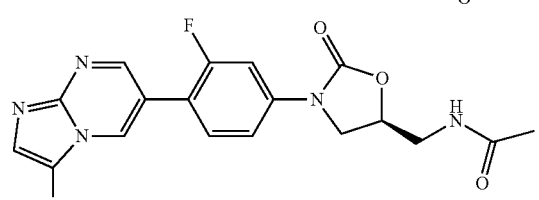
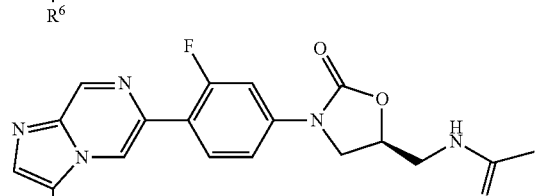
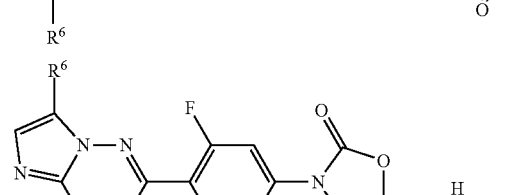
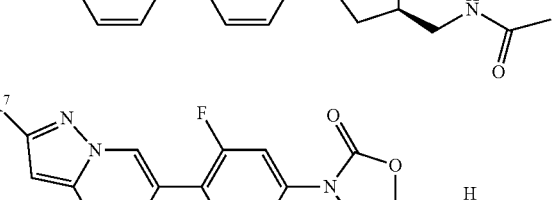
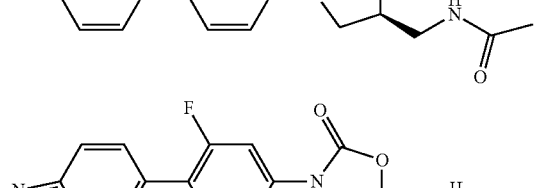
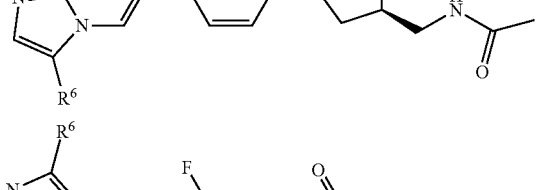

159
-continued
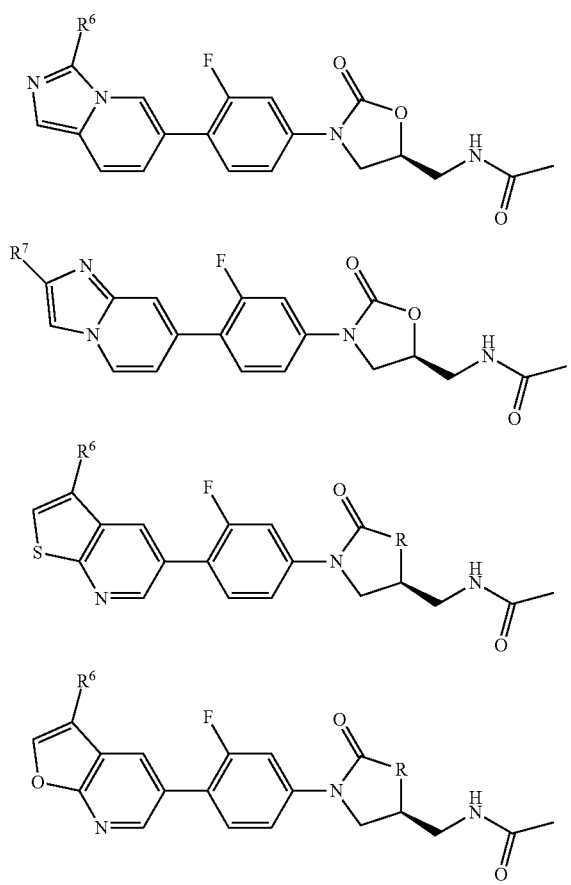
wherein R⁶ or R⁷ is independently selected from the substituents listed in Example C.
Example B
[Chemical Formula 104]
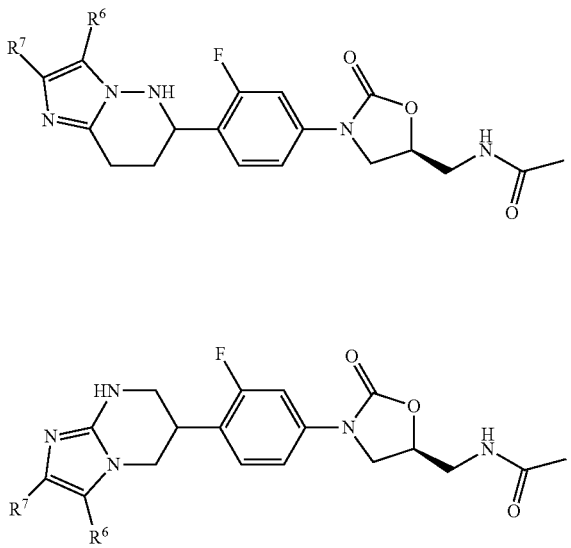
160
-continued
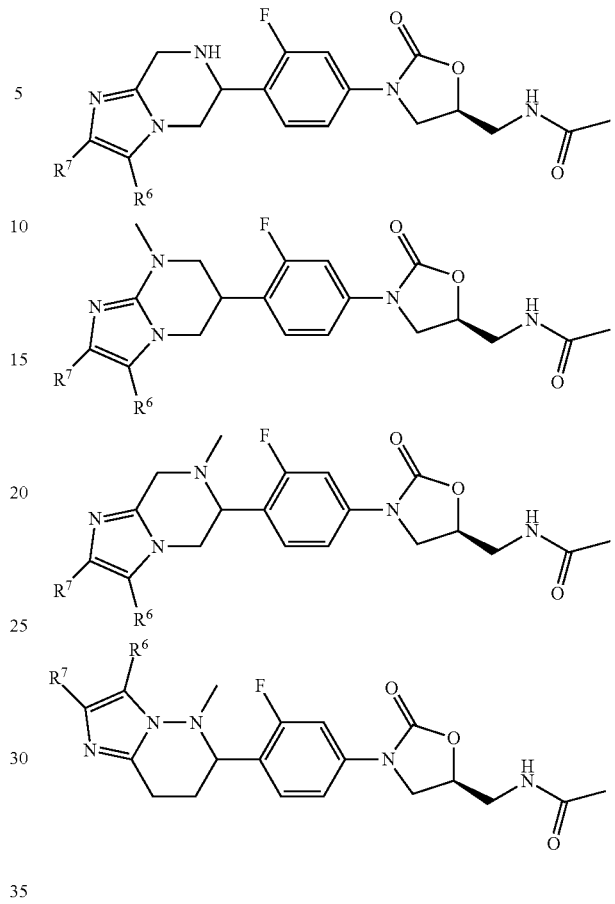
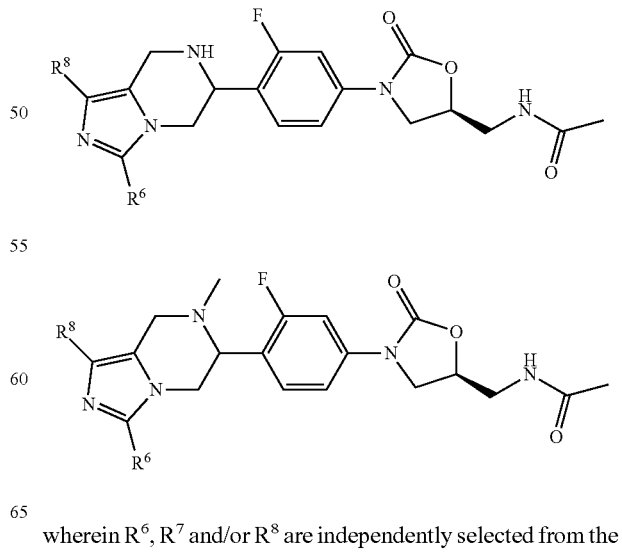
wherein R⁶, R⁷ and/or R⁸ are independently selected from the substituents listed in Example C.

Example B-1
The following preferred embodiments of the compounds of Example B are provided.
[Chemical Formula 105]
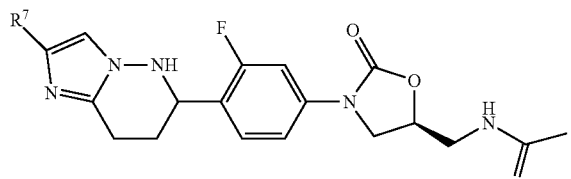
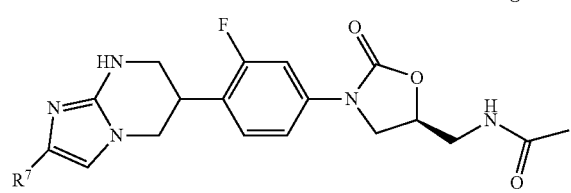
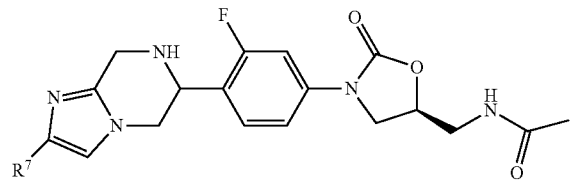
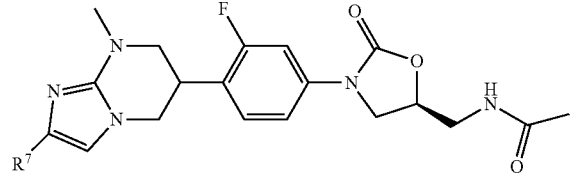
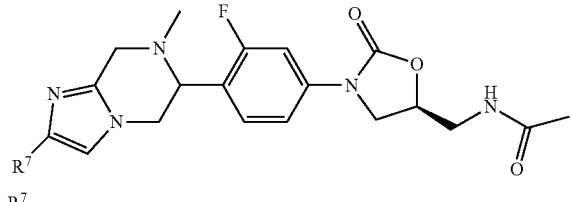
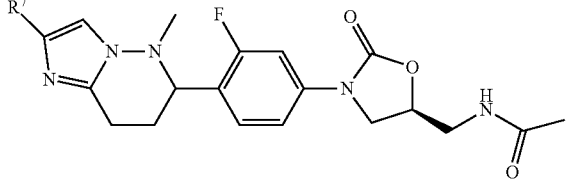
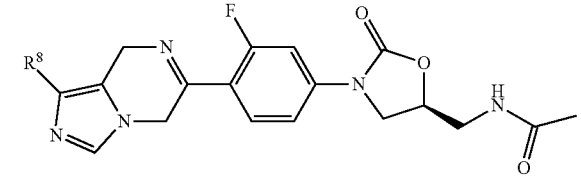
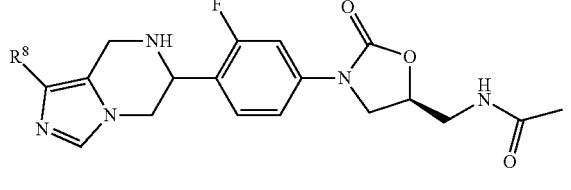
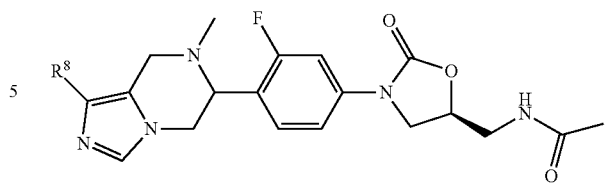
wherein $R^7$ or $R^8$ is independently selected from the substituents listed in Example C.
Example B-2
The following preferred embodiments of the compounds of Example B are provided.
[Chemical Formula 106]
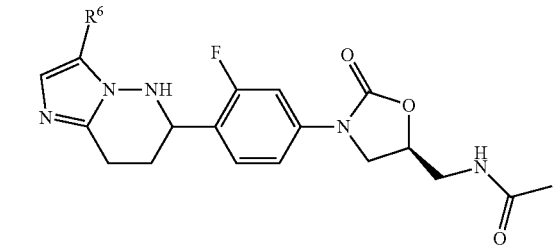
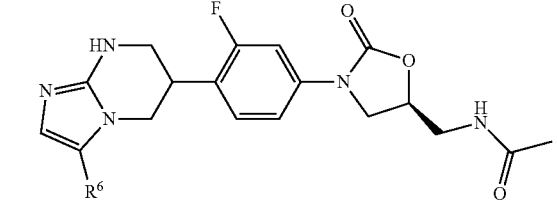
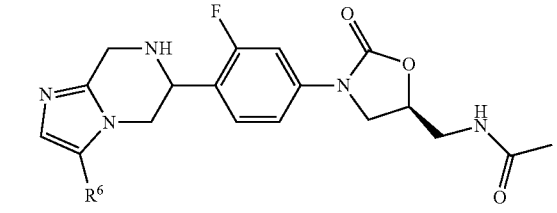
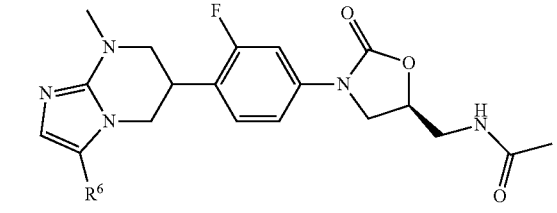
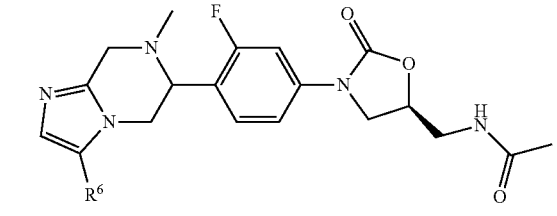

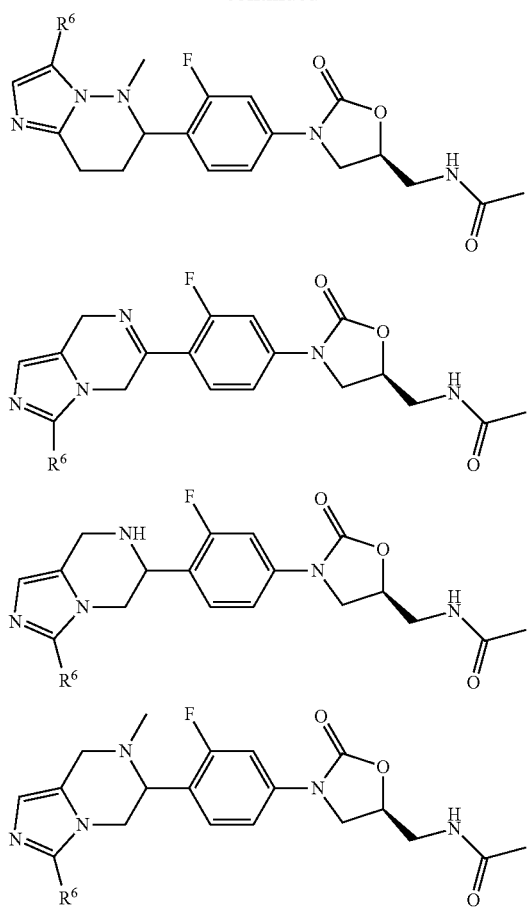
wherein $R^6$ is independently selected from the substituents listed in Example C.
Example C
The following examples of the substituents $R^6$, $R^7$ and $R^8$ on ring D of the compounds of the invention are provided.
[Chemical Formula 107]
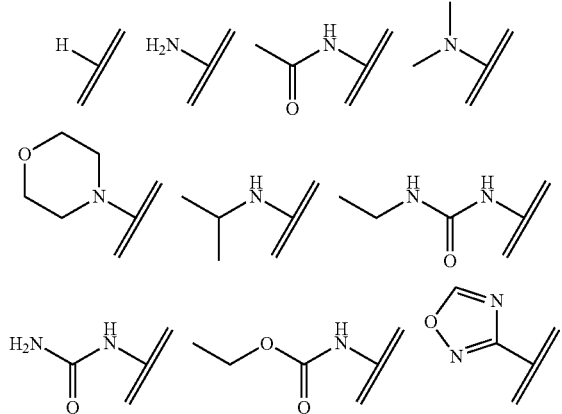
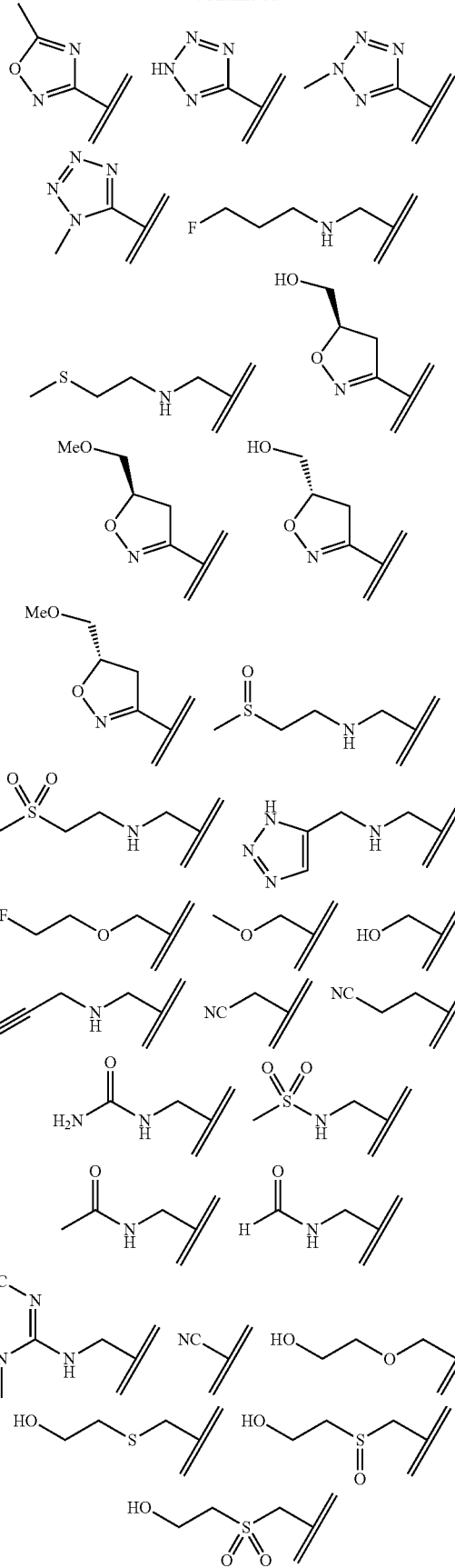

-continued
[Chemical Formula 108]
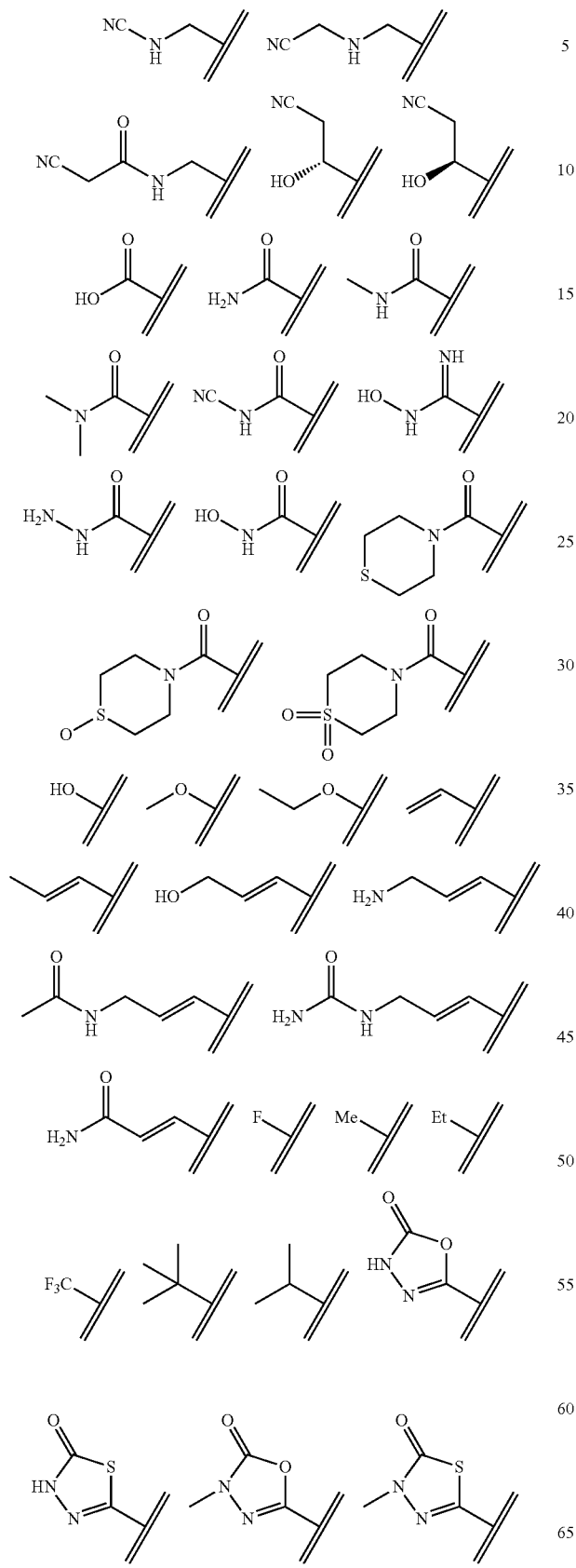
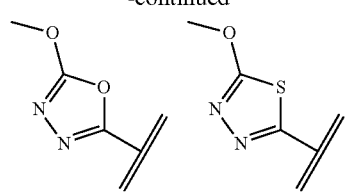
Example D
[Chemical Formula 109]
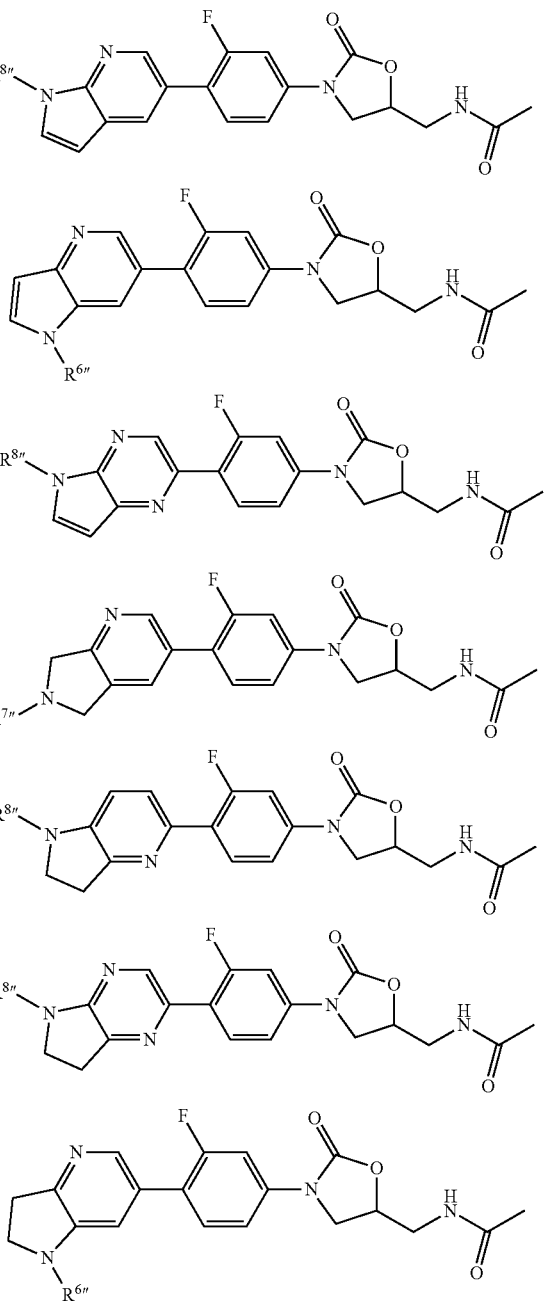

167
-continued

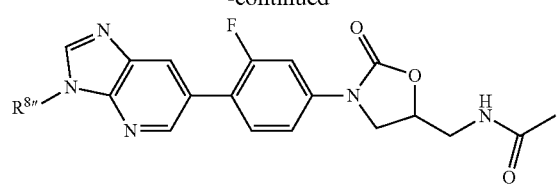

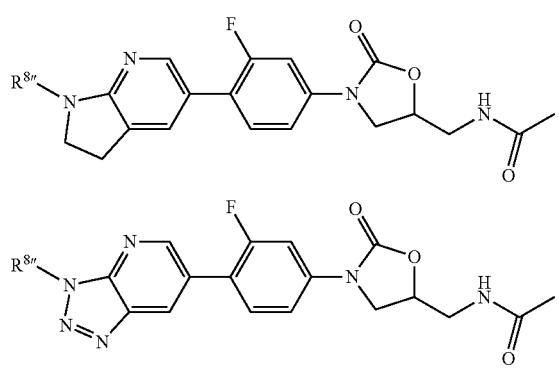

wherein R$^{6''}$, R$^{7''}$ and/or R$^{8''}$ are independently selected from the substituents listed in Example E.

Example E

The following examples of the substituents R$^{6''}$, R$^{7''}$ and R$^{8''}$ on ring D of the compounds of the invention are provided.

[Chemical Formula 110]

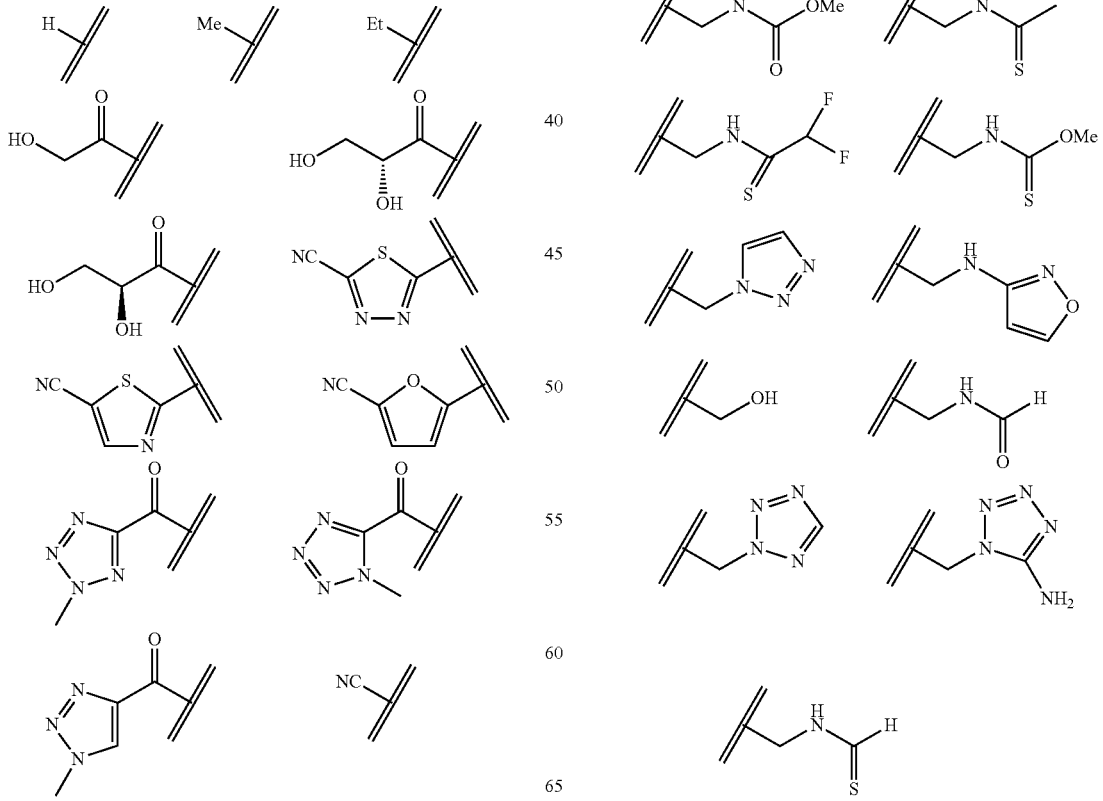

168
Example F

The present invention further provides the compounds as described in the above Examples wherein the oxazolidinone moiety is as follows.

[Chemical Formula 111]

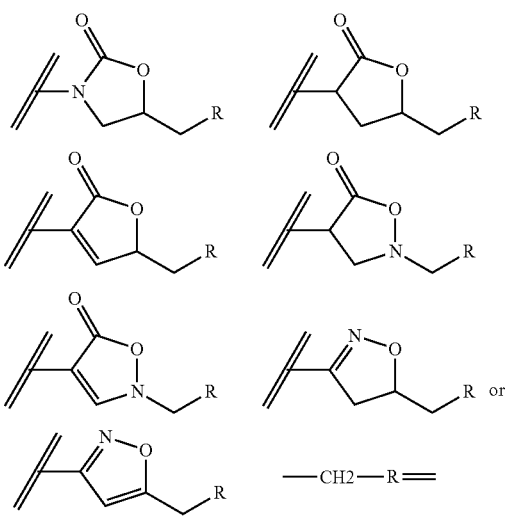

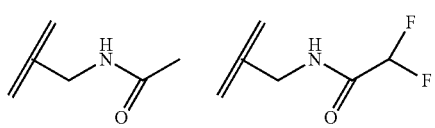

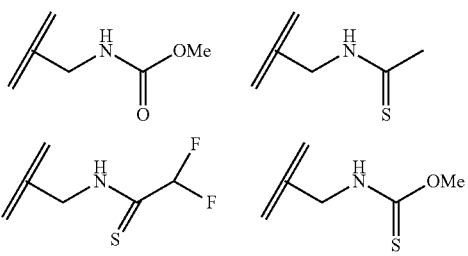

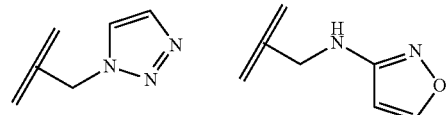

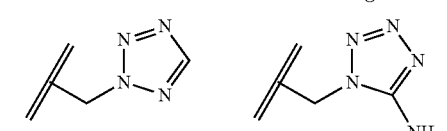

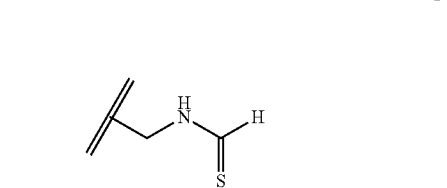

Test Example 1

The compounds of the above Examples were tested for antimicrobial activity.
(Test Method)
Minimal inhibitory concentration (MIC: μg/ml) against different strains of bacteria was determined according to the standard method recommended by CLSI (clinical and laboratory standards institute). The samples used were prepared by dissolving the compound in DMSO at the concentration 1280 μg/mL, followed by a two fold serial dilution with DMSO. The sample was added to a bacteria suspension at the concentration of 5%, and MIC was determined. Cation-adjusted Mueller Hinton Broth was used as a culture media. The inoculation concentration was about $5 \times 10^5$ CFU/mL.
(Result)
The compound of the invention showed a strong antimicrobial activity, which was equivalent or greater than that of conventional drugs, against various strains including methicillin-resistant Staphylococcus aureus (MRSA), linezolid-resistant strains (LZD-R) and vancomycin resistance enterococcus (VRE). For example, the compound of Example 18 showed a strong antimicrobial activity against these resistant strains as shown below.

TABLE 22

| | MIC (μg/mL) | |
|---|---|---|
| Strain | Example 18 | Linezolid |
| S. aureus SR3637 (MRSA) | 0.25 | 2 |
| S. aureus NRS271 (LZD-R) | 2 | 32 |
| E. faecium SR7940 (VRE) | 0.25 | 2 |

[Industrial Applicability]

The compounds of the invention are useful as a drug or as a synthetic intermediate for such drug. Particularly, the compounds of the invention are useful as an antimicrobial drug.

The invention claimed is:
1. An antimicrobial composition comprising a compound of the formula (I):

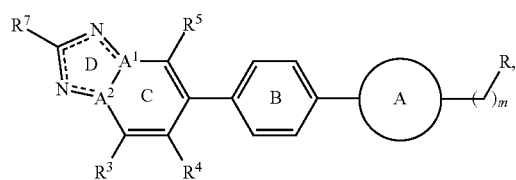
(I)

or a pharmaceutically acceptable salt thereof, and a pharmaceutically acceptable carrier, diluent or excipient; wherein:
ring A is any one of the groups:

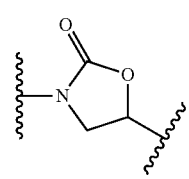
(A-1)

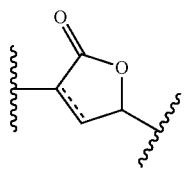
(A-2)

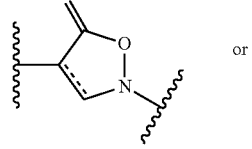
(A-3) or

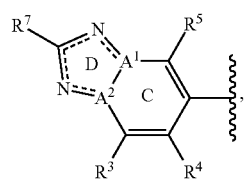
(A-4)

in which the dashed line represents the presence or absence of a bond;
m is 0 or 1;
R is H, —NHC(=O)$R^4$, —NHC(=S)$R^4$, —NH-$het^1$, —O-$het^1$, —S-$het^1$, —S(=O)-$het^1$, —S(=O)$_2$-$het^1$, $het^2$, —CONH$R^4$, —OH, lower alkyl, lower alkoxy or lower alkenyl;
$R^4$ is hydrogen, lower alkyl, halogenated lower alkyl, amino, (lower alkyl)amino, lower alkenyl, heterocycle (lower)alkyl, (lower alkyl)carbonyl, (lower alkyl)carbonyl lower alkyl, lower alkoxy, cycloalkyl, cycloalkyl (lower)alkyl, arylcarbonyl, arylcarbonyl(lower)alkyl, heterocyclecarbonyl or heterocyclecarbonyl(lower)alkyl;
$het^1$ and $het^2$ are independently a heterocyclic group;
ring B is a benzene ring optionally substituted;
$A^1$ and $A^2$ are independently a nitrogen atom or a carbon atom;
the dashed line represents the presence or absence of a bond;
the fused ring C-D,

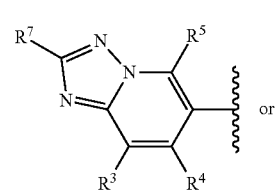

is a fused ring of the formula (II-1-14) or the formula (II-2-14),

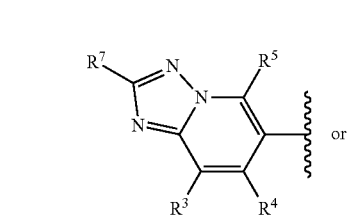
(II-1-14) or

-continued (II-2-14)

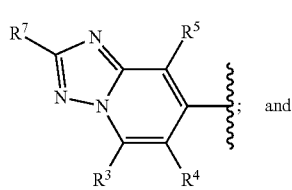

and

R³, R⁴, R⁵, and R⁷ are independently selected from Substituent Group A consisting of hydrogen, optionally substituted lower alkyl, optionally substituted lower alkenyl, optionally substituted lower alkoxy, carboxy, optionally substituted carbamoyl, cyano, formyl, optionally substituted (lower alkyl)carbonyl, optionally substituted (lower alkoxy)carbonyl, optionally substituted heterocyclic group, optionally substituted heterocyclecarbonyl, optionally substituted amino, optionally substituted aminocarbonyl, optionally substituted aryl, optionally substituted arylcarbonyl, (lower alkyl)sulfonyl, (lower alkyl)sulfinyl and halogen.

2. The antimicrobial composition according to claim 1 wherein ring A is the group of the formula (A-1).

3. The antimicrobial composition according to claim 1 wherein m is 1.

4. The antimicrobial composition according to claim 1 wherein R is —NHC(=O)R$^A$ in which R$^A$ is lower alkyl.

5. The antimicrobial composition according to claim 1 wherein R is —NH-het¹, —O-het¹, —S-het¹, —S(=O)-het¹, —S(=O)₂-het¹ or het², wherein het¹ and het² are each independently a five- or six-membered heterocyclic group containing at least one nitrogen atom.

6. The antimicrobial composition according to claim 1 wherein ring B is a benzene ring optionally substituted with the same or different one to four substituent(s) selected from the group consisting of hydrogen, halogen, amino, hydroxy and lower alkyl.

7. The antimicrobial composition according to claim 1 wherein ring B is a benzene ring optionally substituted with one or two halogen(s).

8. The antimicrobial composition according to claim 1 wherein
ring A is the group of the formula (A-1);
m is 1;
R is —NHC(=O)R$^A$, wherein R$^A$ is lower alkyl, or a five- or six-membered heterocyclic group containing at least one nitrogen atom; and
ring B is a benzene ring optionally substituted with one or two halogen(s).

9. A compound of the formula (II):

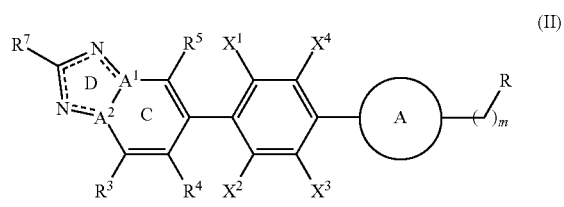

(II)

or a pharmaceutically acceptable salt thereof;

wherein:
ring A is any one of the groups:

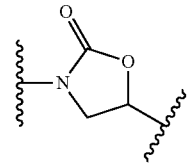

(A-1)

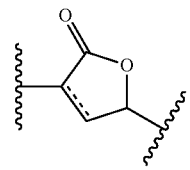

(A-2)

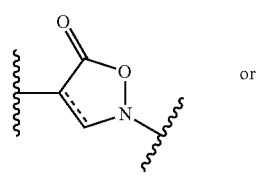

or (A-3)

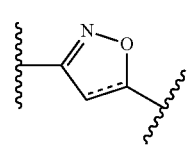

(A-4)

in which the dashed line represents the presence or absence of a bond;

m is 0 or 1;

R is H, —NHC(=O)R$^A$, —NHC(=S)R$^A$, —NH-het¹, —O-het¹, —S-het¹, —S(=O)-het¹, —S(=O)₂-het¹, het², —CONHR$^A$, —OH, lower alkyl, lower alkoxy or lower alkenyl;

R$^A$ is hydrogen, lower alkyl, halogenated lower alkyl, amino, (lower alkyl)amino, lower alkenyl, heterocycle(lower)alkyl, (lower alkyl)carbonyl, (lower alkyl)carbonyl lower alkyl, lower alkoxy, cycloalkyl, cycloalkyl(lower)alkyl, arylcarbonyl, arylcarbonyl(lower)alkyl, heterocyclecarbonyl or heterocyclecarbonyl(lower)alkyl;

het¹ and het² are independently a heterocyclic group;

X¹, X², X³, and X⁴ are independently hydrogen, halogen, amino, hydroxy or lower alkyl;

A¹ and A² are independently a nitrogen atom or a carbon atom;

the dashed line represents the presence or absence of a bond;

the fused ring C-D,

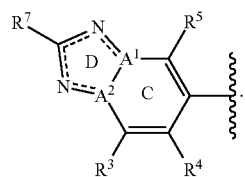

is a fused ring of the formula (II-1-14) or the formula (II-2-14),

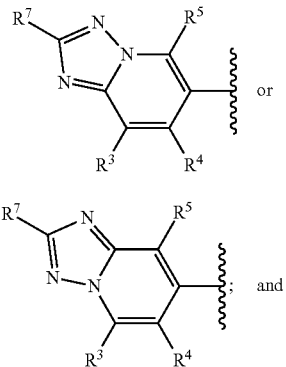

R³, R⁴, R⁵, and R⁷ are independently selected from Substituent Group A consisting of hydrogen, optionally substituted lower alkyl, optionally substituted lower alkenyl, optionally substituted lower alkoxy, carboxy, optionally substituted carbamoyl, cyano, formyl, optionally substituted (lower alkyl)carbonyl, optionally substituted (lower alkoxy)carbonyl, optionally substituted heterocyclic group, optionally substituted heterocyclecarbonyl, optionally substituted amino, optionally substituted aminocarbonyl, optionally substituted aryl, optionally substituted arylcarbonyl, (lower alkyl)sulfonyl, (lower alkyl)sulfinyl and halogen.

10. The compound according to claim 9 wherein any one or two of R³, R⁴ and R⁵ is selected from Substituent Group A, excluding hydrogen, or a pharmaceutically acceptable salt thereof.

11. The compound according to claim 9 wherein the fused ring C-D is

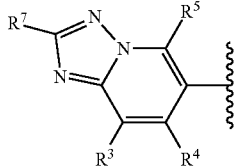

(II-1-14)

or a pharmaceutically acceptable salt thereof.

12. The compound according to claim 11 wherein R³, R⁴ and R⁵ are all hydrogen; and R⁷ is hydrogen, optionally substituted lower alkyl, optionally substituted amino, formyl, or optionally substituted (lower alkyl)carbonyl, or a pharmaceutically acceptable salt thereof.

13. The compound according to claim 9 wherein the fused ring C-D is

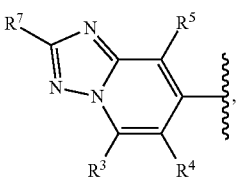

(II-2-14)

or a pharmaceutically acceptable salt thereof.

14. The compound according to claim 13 wherein R³, R⁴ and R⁵ are all hydrogen; and R⁷ is hydrogen, optionally substituted lower alkyl, optionally substituted amino, formyl, or optionally substituted (lower alkyl)carbonyl, or a pharmaceutically acceptable salt thereof.

15. The compound according to claim 9 wherein ring A is the group of the formula (A-1), or a pharmaceutically acceptable salt thereof.

16. The compound according to claim 9 wherein m is 1, or a pharmaceutically acceptable salt thereof.

17. The compound according to claim 9 wherein R is —NHC(=O)R⁴ in which R⁴ is lower alkyl, or a pharmaceutically acceptable salt thereof.

18. The compound according to claim 9 wherein R is —NH-het¹, —O-het¹, —S-het¹, —S(=O)-het¹, —S(=O)₂-het¹ or het², wherein het¹ and het² are each independently a five- or six-membered heterocyclic group containing at least one nitrogen atom, or a pharmaceutically acceptable salt thereof.

19. The compound according to claim 9 wherein R is selected from the group consisting of:

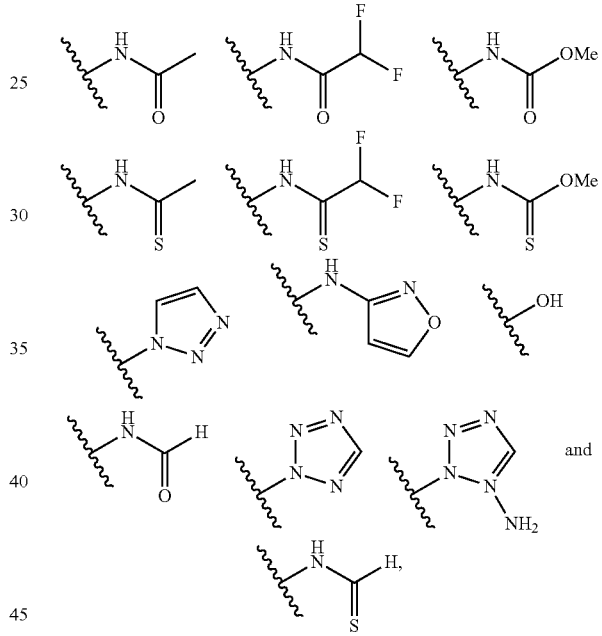

or a pharmaceutically acceptable salt thereof.

20. The compound according to claim 19 wherein R is

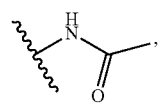 [SMILES: *NC(C)=O]

or a pharmaceutically acceptable salt thereof.

21. The compound according to claim 19 wherein R is

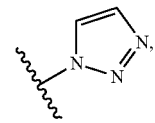

or a pharmaceutically acceptable salt thereof.

22. A method of using the antimicrobial composition according to claim 1 against bacteria, comprising contacting the antimicrobial composition with the bacteria.

23. A method of using the compound of formula (II) according to claim 9 against bacteria, comprising contacting the compound with the bacteria.

* * * * *